United States Patent
Yamano et al.

(10) Patent No.: US 9,238,667 B2
(45) Date of Patent: Jan. 19, 2016

(54) RHODIUM CATALYST AND METHOD FOR PRODUCING AMINE COMPOUND

(71) Applicant: TAKEDA PHARMACEUTICAL COMPANY LIMITED, Osaka (JP)

(72) Inventors: Mitsuhisa Yamano, Osaka (JP); Masatoshi Yamada, Osaka (JP); Hirotsugu Usutani, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/388,383

(22) PCT Filed: Mar. 28, 2013

(86) PCT No.: PCT/JP2013/059191
§ 371 (c)(1),
(2) Date: Sep. 26, 2014

(87) PCT Pub. No.: WO2013/146987
PCT Pub. Date: Oct. 3, 2013

(65) Prior Publication Data
US 2015/0051416 A1 Feb. 19, 2015

(30) Foreign Application Priority Data
Mar. 28, 2012 (JP) ................. 2012-072820

(51) Int. Cl.
| | | |
|---|---|---|
| *C07F 15/00* | (2006.01) | |
| *B01J 31/24* | (2006.01) | |
| *C07B 53/00* | (2006.01) | |
| *C07D 471/04* | (2006.01) | |
| *C07F 9/50* | (2006.01) | |
| *C07C 231/18* | (2006.01) | |
| *C07C 309/30* | (2006.01) | |
| *C07C 241/04* | (2006.01) | |
| *C07C 51/41* | (2006.01) | |

(52) U.S. Cl.
CPC ............ *C07F 15/0073* (2013.01); *B01J 31/24* (2013.01); *B01J 31/2495* (2013.01); *C07B 53/00* (2013.01); *C07C 51/412* (2013.01); *C07C 231/18* (2013.01); *C07C 241/04* (2013.01); *C07C 309/30* (2013.01); *C07D 471/04* (2013.01); *C07F 9/5027* (2013.01); *B01J 2231/645* (2013.01); *B01J 2531/822* (2013.01); *C07B 2200/07* (2013.01); *C07C 2101/14* (2013.01); *C07C 2101/16* (2013.01)

(58) Field of Classification Search
CPC C07F 15/0073; C07F 9/5027; B01J 31/2495; B01J 31/24; B01J 2331/645; B01J 2531/822; C07B 53/00; C07D 471/04; C07C 51/412; C07C 309/30; C07C 241/04; C07C 231/18; C07C 2101/16; C07C 2101/14

USPC ............................................ 556/18; 568/2, 3
See application file for complete search history.

(56) References Cited

U.S. PATENT DOCUMENTS

| | | |
|---|---|---|
| 6,169,179 B1 | 1/2001 | Alper et al. |
| 2006/0199968 A1 | 9/2006 | Yamano et al. |
| 2008/0076925 A1 | 3/2008 | Abrecht et al. |
| 2009/0216019 A1 | 8/2009 | Noyori et al. |

FOREIGN PATENT DOCUMENTS

| | | |
|---|---|---|
| CN | 1788011 | 6/2006 |
| CN | 101511830 | 8/2009 |
| JP | 2000-26407 | 1/2000 |
| JP | 2003-206295 | 7/2003 |
| WO | 2006/103756 | 10/2006 |

OTHER PUBLICATIONS

International Search Report issued Jun. 25, 2013 in International (PCT) Application No. PCT/JP2013/059191.
Burk et al., "Bis(phospholane) Ligands Containing Chiral Backbones. Matching and Mismatching Effects in Enantioselective Hydrogenation of α-Keto Esters", Organometallics, Jan. 2000, vol. 19, pp. 250-260.
Office Action issued Aug. 12, 2015, in corresponding Chinese Application No. 201380027588.3, with English translation.
Imamoto et al., "Sterospecific Reduction of Phosphine Oxides to Phosphines by the Use of a Methylation Reagent and Lithium Aluminum Hydride", Organic Letters, vol. 3, No. 1, pp. 87-90, 2001.
Partial Supplementary European Search Report issued Oct. 5, 2015 in corresponding European Application No. 13767910.6.
MacNeil et al., "Asymmetric Synthesis. Asymmetric Catalytic Hydrogenation Using Chiral Chelating Six-Membered Ring Diphosphines", J. Am. Chem. Soc., vol. 103, 1981, pp. 2273-2280.
(Continued)

*Primary Examiner* — Porfirio Nazario Gonzalez
(74) *Attorney, Agent, or Firm* — Wenderoth, Lind & Ponack, L.L.P.

(57) ABSTRACT

[Problem] Provision of a superior rhodium catalyst and a production method of amine compound.
[Solving Means] A rhodium complex coordinated with a compound represented by the formula

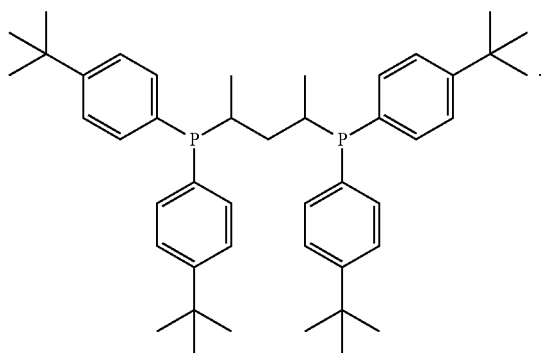

11 Claims, No Drawings

(56) References Cited

OTHER PUBLICATIONS

Herseczki et al., "Electronic and steric effects of ligands as control elements for rhodium-catalyzed asymmetric hydrogenation", Tetrahedron: Asymmetry, vol. 15, 2004, pp. 1673-1676.

McKinstry et al., "An Efficient Procedure for the Synthesis of C-Chiral Bisphosphines", Tetrahedron, vol. 51, No. 28, 1995, pp. 7655-7666.

McKinstry et al., "An Efficient Procedure for the Synthesis of Electron Rich Bisphosphines Containing Homochiral Backbones", Tetrahedron Letters, vol. 35, No. 50, 1994, pp. 9319-9322.

RHODIUM CATALYST AND METHOD FOR PRODUCING AMINE COMPOUND

TECHNICAL FIELD

The present invention relates to a rhodium complex catalyst and a production method of an amine compound. More particularly, the present invention relates to a rhodium complex catalyst effective for the production of an optically active amine compound which is used as a compound useful for a medicament, a pesticide and the like, or a starting material thereof or an intermediate thereof, and a production method of an amine compound.

BACKGROUND ART

As a method for obtaining an optically active amine compound, a method including asymmetric hydrogenation of a prochiral ketimine compound obtained from a carbonyl compound in the presence of an asymmetric metal complex catalyst is available. For example, a method including asymmetric hydrogenation of a ketimine compound in the presence of a rhodium metal complex using an optically active diphosphine compound such as SKEWPHOS and the like as a ligand (non-patent document 1), and a method including asymmetric hydrogenation of tri-substituted enamine in the presence of an iridium metal complex using an optically active phosphine compound such as JOSIPHOS and the like as a ligand, and iodine (non-patent document 2) are disclosed. However, these methods show low catalyst activity and do not show satisfactory results in the asymmetric hydrogenation of tetra-substituted enamine considered difficult to be hydrogenated.

Optically active hexahydropyrroloquinolines are optically active amines industrially useful as synthetic intermediates for optically active physiologically active compound and the like, which are utilized as medicaments and pesticides. Optically active hexahydropyrroloquinolines are used as, for example, important intermediates for NK2 receptor antagonists considered to be useful for the prophylaxis or treatment of neurokinin A-dependent pathology such as lung diseases, gastrointestinal diseases, central nervous diseases, urinary organ diseases, analgesic diseases and the like. While the synthesis of hexahydropyrroloquinolines is found in several disclosures, a further synthesis method that can be applied industrially has been desired (patent documents 1, 2, 3).

Transition metal complexes having an optically active diphosphine compound as a ligand are extremely useful as a catalyst for asymmetric reactions, and a number of catalysts have heretofore been developed. For example, axially chiral diphosphine compound represented by BINAP, diphosphine compounds having chirality on carbon such as DIOP and the like, diphosphine compounds having chirality on phosphorus such as DIPAMP and the like are known. Among the diphosphine compounds having chirality on carbon, pentane-2,4-diylbis(diphenylphosphine) (hereinafter sometimes to be abbreviated as SKEWPHOS) is widely used. Depending on the kind of substrate, reactivity, stereoselectivity, catalyst efficiency and the like are not sufficient, and therefore, various optically active phosphines have been produced and reported (non-patent documents 3, 4, patent document 4).

As a production method of SKEWPHOS and SKEWPHOS analogs, some have been disclosed heretofore (non-patent documents 5, 6, patent document 4). However, these methods are industrially unsatisfactory since they use alkyllithium, which is industrially difficult to handle, when obtaining phosphine lithium salt and phosphine borane lithium salt, they include severe reaction conditions for the synthesis of phosphine lithium salt or phosphine borane lithium salt, and synthesis steps of diphosphine compound or diphosphine diborane compound, and the like.

As for SKEWPHOS analogs, a production method including asymmetric hydrogenation in the presence of ruthenium metal complex using an optically active pentane-2,4-diylbis(bis(4-(tert-butyl)phenyl)phosphine) compound represented by

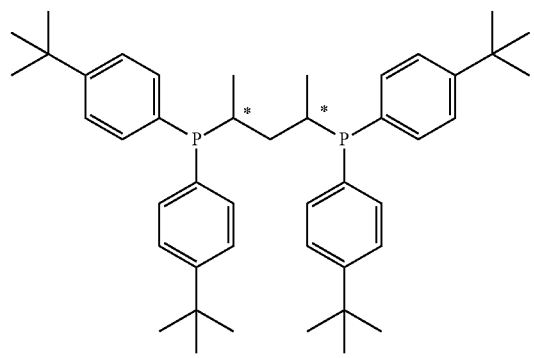 [SMILES: CC(CC(C)P(c1ccc(C(C)(C)C)cc1)c1ccc(C(C)(C)C)cc1)P(c1ccc(C(C)(C)C)cc1)c1ccc(C(C)(C)C)cc1]

(hereinafter sometimes to be abbreviated as PTBP-SKEWPHOS) as a ligand, to obtain optically active 3-quinuclidinols is disclosed (patent document 5). However, the central transition metal is limited to ruthenium, and there is still a room for consideration depending on the kind of the central metal to be used, the kind of the reaction substrate and the like.

DOCUMENT LIST

Patent Documents patent document 1: Japanese patent application No. 2006-540061
patent document 2: WO 2010-038434
patent document 3: WO 2010-038435
patent document 4: JP-A-2003-206295
patent document 5: WO 2006-103756

Non-Patent Document non-patent document 1: J. Chem. Soc., Chem. Commun. 1991. 1684
non-patent document 2: J. Am. Chem. Soc. 2009, 131, 1366-1367
non-patent document 3: Tetrahedron: Asymmetry 2004, 15, 1673-1676
non-patent document 4: J. Mol. Catal. 1997, 116, 199-207
non-patent document 5: Phosphorus Ligands in Asymmetric Catalysis, 2008, WILEY-VCH
non-patent document 6: Tetrahedron: Asymmetry 2004, 15, 1673-1676

SUMMARY OF THE INVENTION

Problems to be Solved by the Invention

The present invention aims to provide an efficient synthesis method of SKEWPHOS analogs and a rhodium complex catalyst therefor and a production method of an optically active amine compounds, particularly, optically active hexahydropyrroloquinolines which is superior to conventional transition metal complex catalysts using an optically active diphosphine compound as a ligand, and the development of an additive advantageous for asymmetric hydrogenation reactions.

Means of Solving the Problems

In view of the aforementioned problems, the present inventors have studied, as an industrial production method of an optically active diphosphine ligand SKEWPHOS and SKEWPHOS analogs, avoidance of lithium salification using alkyllithium and extremely low temperature reaction. As a result, the present inventors have found that the reaction proceeds under mild conditions by using a particular base, and completed an industrial production method of SKEWPHOS and SKEWPHOS analogs. Furthermore, rhodium complex catalyst using PTBP-SKEWPHOS as a ligand asymmetrically hydrogenates tetra-substituted enamine in the presence of a compound having a particular aromatic hydroxy group and a particular acetal to construct an optically active hexahydropyrroloquinoline ring, which resulted in the completion of the present invention.

Accordingly, the present invention relates to

[1] a rhodium complex coordinated with a compound represented by the formula

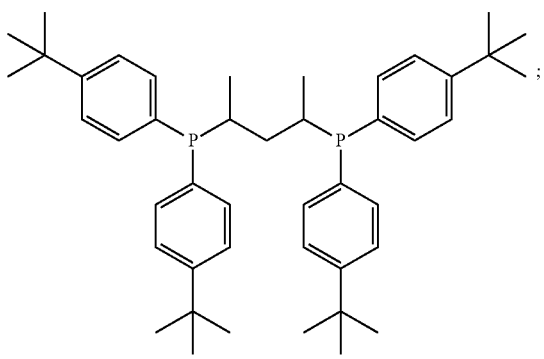 [SMILES: CC(CC(C)P(c1ccc(C(C)(C)C)cc1)c1ccc(C(C)(C)C)cc1)P(c1ccc(C(C)(C)C)cc1)c1ccc(C(C)(C)C)cc1]

[2] the complex of the aforementioned [1], which is a rhodium complex coordinated with a compound represented by the formula

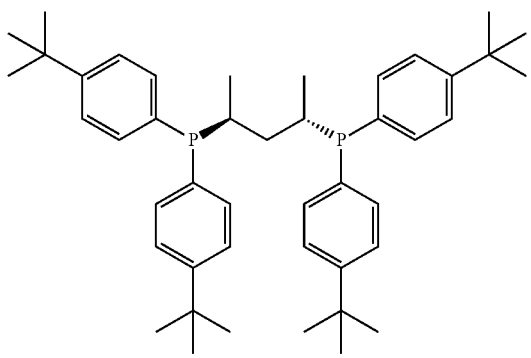 [SMILES: C[C@@H](C[C@H](C)P(c1ccc(C(C)(C)C)cc1)c1ccc(C(C)(C)C)cc1)P(c1ccc(C(C)(C)C)cc1)c1ccc(C(C)(C)C)cc1]

or the formula

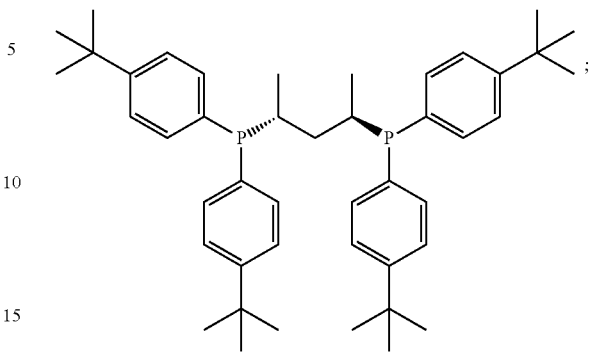

[3] a method of producing a compound represented by the formula

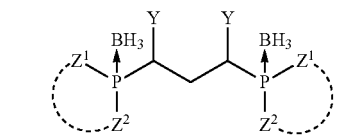

wherein $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), and Y is a hydrocarbon group optionally having substituent(s) or a heterocyclic group optionally having substituent(s), or a salt thereof, comprising reacting a compound represented by the formula

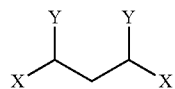

wherein X is a leaving group, and Y is as defined above, or a salt thereof, with
a compound represented by the formula

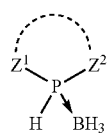

wherein each symbol is as defined above, or a salt thereof, in the presence of potassium tert-butoxide or sodium tert-butoxide;

[4] a method of producing a compound represented by the formula

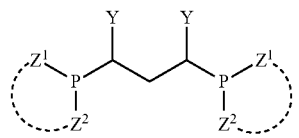

wherein Y is a hydrocarbon group optionally having substituent(s) or a heterocyclic group optionally having substituent(s), $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), or a salt thereof, comprising reacting a compound represented by the formula

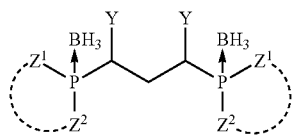

wherein each symbol is as defined above, or a salt thereof, in the presence of a base;

[5] a compound represented by the formula

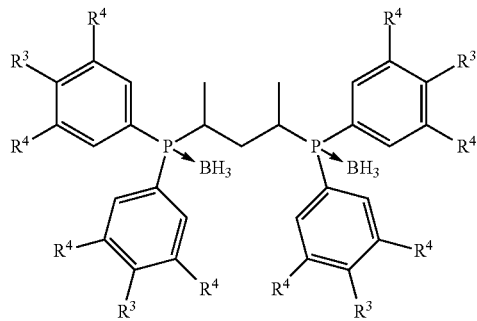

wherein $R^3$ is a hydrogen atom, a $C_{1-6}$ alkyl group, a $C_{1-6}$ alkoxy group or a di-$C_{1-6}$ alkylamino group, and $R^4$ is a hydrogen atom or a $C_{1-6}$ alkyl group, or a salt thereof;

[6] a method of producing a compound represented by the formula

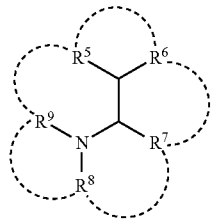

wherein $R^5$, $R^6$ and $R^7$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, an alkoxycarbonyl group optionally having substituent(s), a carboxyl group, a carbamoyl group optionally having substituent(s), a sulfonyl group optionally having substituent(s), a sulfinyl group optionally having substituent(s) or a thiol group optionally having substituent(s), $R^8$ and $R^9$ are the same or different and each is a hydrogen atom, a hydrocarbon group optionally having substituent(s), a heterocyclic group optionally having substituent(s), an acyl group, a sulfonyl group optionally having substituent(s) or a silyl group optionally having substituent(s), and $R^5$ and $R^6$, $R^6$ and $R^7$, $R^7$ and $R^8$, $R^8$ and $R^9$, and $R^9$ and $R^5$ are each optionally joined to form, together with the adjacent atom, a 4- to 8-membered ring optionally having substituent(s), or a salt thereof, comprising reacting a compound represented by the formula

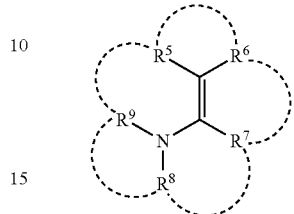

wherein each symbol is as defined above, or a salt thereof, with hydrogen in the presence of a transition metal complex as a catalyst and an aromatic compound having a hydroxy group;

[7] a method of producing a compound represented by the formula

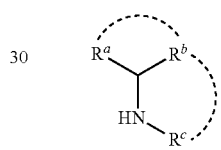

wherein $R^a$ and $R^b$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, a sulfonyl group optionally having substituent(s), a sulfinyl group optionally having substituent(s) or a thiol group optionally having substituent(s), $R^c$ is a hydrogen atom, a hydrocarbon group optionally having substituent(s), a heterocyclic group optionally having substituent(s), an acyl group, an amino group optionally having substituent(s), a sulfonyl group optionally having substituent(s) or a silyl group optionally having substituent(s), and $R^a$ and $R^b$, and $R^b$ and $R^c$ are each optionally joined to form, together with the adjacent atom, a 4- to 8-membered ring optionally having substituent(s), or a salt thereof, comprising reacting a compound represented by the formula

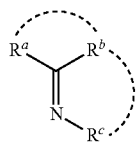

wherein each symbol is as defined above, or a salt thereof, with hydrogen in the presence of a transition metal complex as a catalyst and an aromatic compound having a hydroxy group;

[8] a method of producing a compound represented by the formula

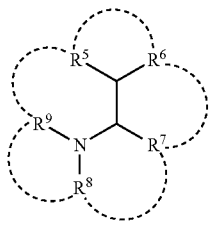

wherein $R^5$, $R^6$ and $R^7$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, an alkoxycarbonyl group optionally having substituent(s), a carboxyl group, a carbamoyl group optionally having substituent(s), a sulfonyl group optionally having substituent(s), a sulfinyl group optionally having substituent(s) or a thiol group optionally having substituent(s), $R^8$ and $R^9$ are the same or different and each is a hydrogen atom, a hydrocarbon group optionally having substituent(s), a heterocyclic group optionally having substituent(s), an acyl group, a sulfonyl group optionally having substituent(s) or a silyl group optionally having substituent(s), and $R^5$ and $R^6$, $R^6$ and $R^7$, $R^7$ and $R^8$, $R^8$ and $R^9$, and $R^9$ and $R^5$ are each optionally joined to form, together with the adjacent atom, a 4- to 8-membered ring optionally having substituent(s), or a salt thereof, comprising reacting a compound represented by the formula

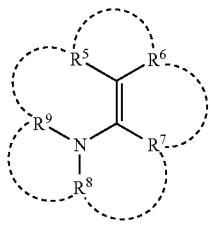

wherein each symbol is as defined above, or a salt thereof, with hydrogen in the presence of a transition metal complex as a catalyst and a compound represented by the formula

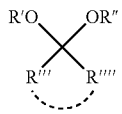

wherein R' and R" are the same or different and each is an alkyl group optionally having substituent(s), R''' and R'''' are the same or different and each is an alkyl group optionally having substituent(s), or R''' and R'''' are joined to form, together with the adjacent carbon atom, a 4- to 9-membered ring optionally having substituent(s);

[9] a method of producing a compound represented by the formula

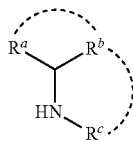

wherein $R^a$ and $R^b$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, a sulfonyl group optionally having substituent(s), a sulfinyl group optionally having substituent(s) or a thiol group optionally having substituent(s), $R^c$ is a hydrogen atom, a hydrocarbon group optionally having substituent(s), a heterocyclic group optionally having substituent(s), an acyl group, an amino group optionally having substituent(s), a sulfonyl group optionally having substituent(s) or a silyl group optionally having substituent(s), and $R^a$ and $R^b$, and $R^b$ and $R^c$ are each optionally joined to form, together with the adjacent atom, a 4- to 8-membered ring optionally having substituent(s), or a salt thereof, comprising reacting a compound represented by the formula

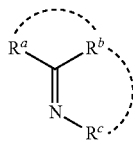

wherein each symbol is as defined above, or a salt thereof, with hydrogen in the presence of a transition metal complex as a catalyst and a compound represented by the formula

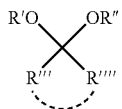

wherein R' and R" are the same or different and each is an alkyl group optionally having substituent(s), R''' and R'''' are the same or different and each is an alkyl group optionally having substituent(s), or R''' and R'''' are joined to form, together with the adjacent carbon atom, a 4- to 9-membered ring optionally having substituent(s);

[10] the method of the aforementioned [6] or [7], wherein the aromatic compound having a hydroxy group is a cyanuric acid;

[11] the method of the aforementioned [8] or [9], wherein the compound represented by the formula

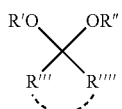

is 2,2-dimethoxypropane;

[12] the method of the aforementioned [3], wherein the reaction does not accompany racemization;

[13] the method of the aforementioned [3], wherein the compound represented by the formula

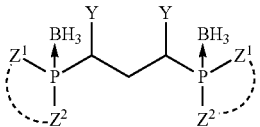

wherein Y is a hydrocarbon group optionally having substituent(s) or a heterocyclic group optionally having substituent(s), $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), or a salt thereof, is an optically active compound;

[14] the method of the aforementioned [3], wherein the compound represented by the formula

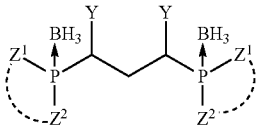

wherein Y is a hydrocarbon group optionally having substituent(s) or a heterocyclic group optionally having substituent(s), $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), or a salt thereof, is a racemate;

[15] the method of the aforementioned [4], comprising the reaction does not accompany racemization;

[16] the method of the aforementioned [4], wherein the compound represented by the formula

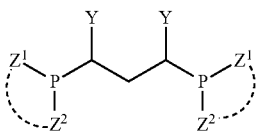

wherein Y is a hydrocarbon group optionally having substituent(s) or a heterocyclic group optionally having substituent(s), $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), or a salt thereof, is an optically active compound;

[17] the method of the aforementioned [4], wherein the compound represented by the formula

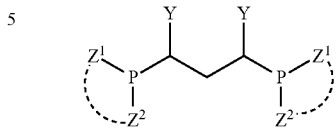

wherein Y is a hydrocarbon group optionally having substituent(s) or a heterocyclic group optionally having substituent(s), $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), or a salt thereof, is a racemate;

[18] a method of producing a compound represented by the formula

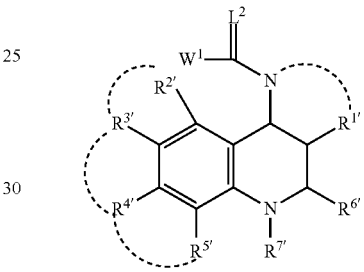

wherein $R^{1'}$ is a hydrogen atom or an alkyl group optionally having substituent(s), or $R^{1'}$ and a nitrogen atom of the formula $W^1$—C(=$L^2$)-N— group are joined to form, together with the adjacent atom, a 4- to 9-membered nitrogen-containing heterocycle optionally having substituent(s), $L^2$ is an oxygen atom, a sulfur atom or an imino group optionally having substituent(s), $W^1$ is an amino group optionally having substituent(s) or a hydroxy group optionally having substituent(s), $R^{2'}$, $R^{3'}$, $R^{4'}$ and $R^{5'}$ are the same or different and each is a hydrogen atom, a halogen atom, a nitro group, a cyano group, a hydrocarbon group optionally having substituent(s), a heterocyclic group optionally having substituent(s), an amino group optionally having substituent(s), a hydroxy group optionally having substituent(s), an alkylcarbonyl group optionally having substituent(s), an alkoxycarbonyl group optionally having substituent(s), a carboxyl group, a carbamoyl group optionally having substituent(s), or $R^{2'}$ and $R^{3'}$, $R^{3'}$ and $R^{4'}$, and $R^{4'}$ and $R^{5'}$ are each optionally joined to form, together with the adjacent atom, a 4- to 8-membered ring optionally having substituent(s), $R^{6'}$ is a hydrogen atom, a halogen atom, a hydrocarbon group optionally having substituent(s), a heterocyclic group optionally having substituent(s), a hydroxy group optionally having substituent(s), an alkylcarbonyl group optionally having substituent(s), an alkoxycarbonyl group optionally having substituent(s), a carbamoyl group optionally having substituent(s) or a carboxyl group, $R^{7'}$ is a hydrogen atom, a hydrocarbon group optionally having substituent(s), a heterocyclic group optionally having substituent(s), an acyl group, a sulfonyl group optionally having substituent(s) or a silyl group optionally having substituent(s), or a salt thereof, comprising reacting a compound represented by the formula

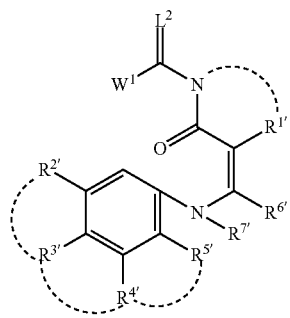

wherein each symbol is as defined above, or a salt thereof, with hydrogen;

[19] the method of the aforementioned [18], comprising reacting with hydrogen by using a transition metal complex as a catalyst in the presence of an aromatic compound having a hydroxy group;

[20] the method of the aforementioned [18], comprising reacting with hydrogen, in the presence of a transition metal complex as a catalyst and a compound represented by the formula

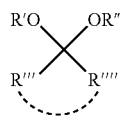

wherein R' and R'' are the same or different and each is an alkyl group optionally having substituent(s), R''' and R'''' are the same or different and each is an alkyl group optionally having substituent(s), or R''' and R'''' are optionally joined to form, together with the adjacent carbon atom, a 4- to 9-membered ring optionally having substituent(s);

[21] the method of any of the aforementioned [6], [7], [8], [9] and [18], wherein the transition metal complex is a rhodium complex;

[22] the method of any of the aforementioned [6], [7], [8], [9] and [18], comprising reacting in the presence of acetone;

[23] the method of any of the aforementioned [6], [7], [8], [9] and [18], wherein the transition metal complex is a rhodium complex obtained by coordinating with a compound represented by the formula

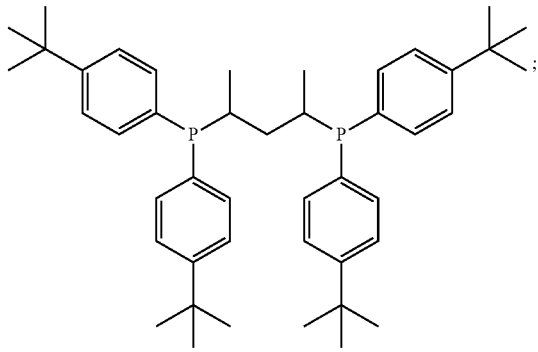 [SMILES: CC(CC(C)P(c1ccc(C(C)(C)C)cc1)c1ccc(C(C)(C)C)cc1)P(c1ccc(C(C)(C)C)cc1)c1ccc(C(C)(C)C)cc1]

[24] the method of the aforementioned [6] or [8], wherein the obtained compound is a compound represented by the formula

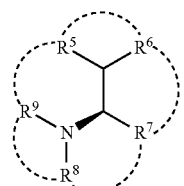

or the formula

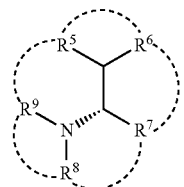

wherein $R^5$, $R^6$ and $R^7$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, an alkoxycarbonyl group optionally having substituent(s), a carboxyl group, a carbamoyl group optionally having substituent(s), a sulfonyl group optionally having substituent(s), a sulfinyl group optionally having substituent(s) or a thiol group optionally having substituent(s), $R^8$ and $R^9$ are the same or different and each is a hydrogen atom, a hydrocarbon group optionally having substituent(s), a heterocyclic group optionally having substituent(s), an acyl group, a sulfonyl group optionally having substituent(s) or a silyl group optionally having substituent(s), and $R^5$ and $R^6$, $R^6$ and $R^7$, $R^7$ and $R^8$, $R^8$ and $R^9$, and $R^9$ and $R^5$ are each optionally joined to form, together with the adjacent atom, a 4- to 8-membered ring optionally having substituent(s), or a salt thereof;

[25] the method of the aforementioned [7] or [9], wherein the obtained compound is a compound represented by the formula

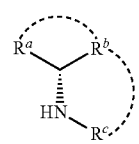

or the formula

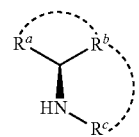

wherein $R^a$ and $R^b$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, a sulfonyl group optionally having substituent(s), a sulfinyl group optionally having substituent(s) or a thiol group optionally having substituent(s), $R^c$ is a hydrogen atom, a so hydrocarbon group optionally having substituent(s), a heterocyclic group optionally having substituent(s), an acyl group, an amino group optionally having substituent(s), a sulfonyl group optionally having substituent(s) or a silyl group optionally having substituent(s), and $R^a$ and $R^b$, and $R^b$ and $R^c$ are each optionally joined to form, together with the adjacent atom, a 4- to 8-membered ring optionally having substituent(s), or a salt thereof;

[26] a method of producing a compound represented by the formula

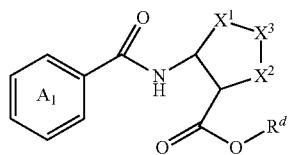

wherein ring $A_1$ is a benzene ring optionally having substituent(s), $R^d$ is a hydrogen atom, a $C_{1-6}$ alkyl group optionally having substituent(s) or a $C_{7-14}$ aralkyl group optionally having substituent(s), and $X^1$, $X^2$ and $X^3$ are each a bond or a divalent $C_{1-5}$ chain hydrocarbon group optionally having substituent(s), or a salt thereof, comprising reacting a compound represented by the formula

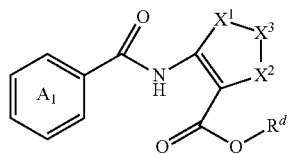

wherein each symbol is as defined above, or a salt thereof with hydrogen; and

[27] a method of producing a compound represented by the formula

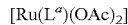
[Ru($L^a$)(OAc)$_2$]

wherein $L^a$ is a diphosphine ligand, and Ac is acetyl, comprising reacting a compound represented by the formula

[Ru($X^a$)(Ar$^a$)($L^a$)]$X^b$ wherein $X^a$ is a halogen atom, Ar$^a$ is a benzene ring optionally having substituent(s), $L^a$ is a diphosphine ligand, and $X^b$ is a counter ion, with alkali metal acetate.

Effect of the Invention

According to the present invention, a rhodium complex effective for the production of an optically active amine compound which is used as a compound useful for a medicament, a pesticide and the like, or a starting material thereof or an intermediate thereof, and a production method of an amine compound could be provided.

While the present invention is explained in detail in the following, it is not particularly limited to those exemplified. The explanation on each group for each symbol is used where necessary throughout the present application.

The "$C_{1-4}$ alkyl group" is a straight chain or branched alkyl group having a carbon number of 1 to 4, and means methyl, ethyl, propyl, isopropyl, butyl, isobutyl, sec-butyl, tert-butyl and the like.

The "$C_{1-6}$ alkyl group" is a straight chain or branched alkyl group having a carbon number of 1 to 6, and means methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

The "$C_{1-6}$ alkoxy group" is a straight chain or branched alkoxy group having a carbon number of 1 to 6, and means methoxy, ethoxy, propoxy, isopropoxy, butoxy, isobutoxy, sec-butoxy, tert-butoxy and the like.

The "halogen atom" means fluorine, chlorine, bromine, iodine and the like.

Examples of the "hydrocarbon group" of the "hydrocarbon group optionally having substituent(s)" for Y include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, and a $C_{8-13}$ arylalkenyl group.

Here, the "$C_{1-10}$ alkyl group" is a straight chain or branched alkyl group having a carbon number of 1 to 10, and examples thereof include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like. Of these, a straight chain or branched alkyl group having a carbon number of 1 to 6 is preferable.

The "$C_{2-10}$ alkenyl group" is a straight chain or branched alkenyl group having a carbon number of 2 to 10, and examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like. Of these, a straight chain or branched alkenyl group having a carbon number of 2 to 6 is preferable.

The "$C_{2-10}$ alkynyl group" is a straight chain or branched alkynyl group having a carbon number of 2 to 10, and examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like. Of these, a straight chain or branched alkynyl group having a carbon number of 2 to 10 is preferable.

The "$C_{3-10}$ cycloalkyl group" is a cyclic alkyl group having a carbon number of 3 to 10, and examples thereof include cyclopropyl, cyclobutyl, cyclopentyl, cyclohexyl, cycloheptyl, cyclooctyl and the like. Of these, a cycloalkyl group having a carbon number of 3 to 6 is preferable.

The "$C_{3-10}$ cycloalkenyl group" is a cyclic alkenyl group having a carbon number of 3 to 10, and examples thereof include 2-cyclopenten-1-yl, 3-cyclopenten-1-yl, 2-cyclohexen-1-yl, 3-cyclohexen-1-yl and the like. Of these, a cycloalkenyl group having a carbon number of 3 to 6 is preferable.

The "$C_{4-10}$ cycloalkadienyl group" is a cyclic alkadienyl group having a carbon number of 4 to 10, and examples thereof include 2,4-cyclopentadien-1-yl, 2,4-cyclohexadien-1-yl, 2,5-cyclohexadien-1-yl and the like. Of these, a cycloalkadienyl group having a carbon number of 4 to 6 is preferable.

The above-mentioned "$C_{3-10}$ cycloalkyl group", "$C_{3-10}$ cycloalkenyl group" and "$C_{4-10}$ cycloalkadienyl group" may respectively form a fused ring group by condensing with a benzene ring. Examples of said fused ring group include indanyl, dihydronaphthyl, tetrahydronaphthyl, fluorenyl and the like.

The above-mentioned "$C_{3-10}$ cycloalkyl group", "$C_{3-10}$ cycloalkenyl group" and "$C_{4-10}$ cycloalkadienyl group" may be a bridged hydrocarbon group having a carbon number of 7 to 10, and examples of such bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

Furthermore, the above-mentioned "$C_{3-10}$ cycloalkyl group", "$C_{3-10}$ cycloalkenyl group" and "$C_{4-10}$ cycloalkadienyl group" may form a spiro-ring group with "$C_{3-10}$ cycloalkane", "$C_{3-10}$ cycloalkene" and "$C_{4-10}$ cycloalkadiene", respectively. Here, examples of the "$C_{3-10}$ cycloalkane", "$C_{3-10}$ cycloalkene" and "$C_{4-10}$ cycloalkadiene" include rings corresponding to the above-mentioned "$C_{3-10}$ cycloalkyl group", "$C_{3-10}$ cycloalkenyl group" and "$C_{4-10}$ cycloalkadienyl group". Examples of such spiro-ring group include spiro[4.5]decan-8-yl and the like.

The "$C_{6-14}$ aryl group" is an aryl group having a carbon number of 6 to 14, and examples thereof include phenyl, naphthyl, anthryl, phenanthryl, acenaphthylenyl, biphenylyl and the like. Of these, an aryl group having a carbon number of 6 to 12 is preferable.

The "$C_{7-13}$ aralkyl group" is an aralkyl group having a carbon number of 7 to 13, and examples thereof include benzyl, phenethyl, naphthylmethyl, biphenylylmethyl and the like.

The "$C_{8-13}$ arylalkenyl group" is an arylalkenyl group having a carbon number of 8 to 13, and examples thereof include styryl and the like.

The "$C_{1-10}$ alkyl group", "$C_{2-10}$ alkenyl group" and "$C_{2-10}$ alkynyl group" in the "hydrocarbon group" of the "hydrocarbon group optionally having substituent(s)" for Y may have 1 to 7 (preferably, 1 to 3) substituents at substitutable position(s).

Examples of such substituent include (1) nitro, (2) nitroso, (3) cyano, (4) hydroxy, (5) a $C_{1-6}$ alkoxy group, (6) formyl, (7) a $C_{1-6}$ alkyl-carbonyl group (e.g., acetyl, propionyl, butyryl, isobutyryl, valeryl, isovaleryl, pivaloyl etc.), (8) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.), (9) carboxyl, (10) a N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl etc.), (11) a N,N-di-$C_{1-6}$ alkyl-carbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl etc.), (12) a halogen atom (fluorine, chlorine, bromine, iodine), (13) a mono-$C_{1-6}$ alkylamino group (e.g., methylamino, ethylamino, propylamino, isopropylamino, butylamino, isobutylamino, sec-butylamino, tert-butylamino, pentylamino, hexylamino etc.), (14) a di-$C_{1-6}$ alkylamino group (e.g., dimethylamino, diethylamino, dipropylamino, diisopropylamino, dibutylamino, N-ethyl-N-methylamino etc.) and the like.

The "$C_{3-10}$ cycloalkyl group", "$C_{3-10}$ cycloalkenyl group", "$C_{4-10}$ cycloalkadienyl group", "$C_{6-14}$ aryl group", "$C_{7-13}$ aralkyl group" and "$C_{8-13}$ arylalkenyl group" in the "hydrocarbon group" of the "hydrocarbon group optionally having substituent(s)" for Y may have 1 to 3 substituents at substitutable position(s).

Examples of such substituent include
(1) the groups exemplified as the substituents of the aforementioned $C_{1-10}$ alkyl group and the like;

(2) a $C_{1-6}$ alkyl group optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;

(3) a $C_{2-10}$ alkenyl group (e.g., ethenyl, 1-propenyl) optionally substituted by 1 to 3 substituents selected from
  (a) a halogen atom,
  (b) a carboxy group,
  (c) a hydroxy group,
  (d) a $C_{1-6}$ alkoxy-carbonyl group,
  (e) a $C_{1-6}$ alkoxy group, and
  (f) an amino group optionally mono- or di-substituted by a $C_{1-6}$ alkyl group;

(4) a $C_{7-13}$ aralkyl group (e.g., benzyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom;

and the like. When the number of the substituents is two or more, the respective substituents may be the same or different.

The "heterocyclic group" of the "heterocyclic group optionally having substituent(s)" for Y is an "aromatic heterocyclic group" or a "nonaromatic heterocyclic group". The "aromatic heterocyclic group" is an aromatic 5- to 8-membered (monocyclic, dicyclic or tricyclic) heterocyclic group having, besides carbon atom, 1 to 3 kinds of 1 to 5 hetero atoms selected from an oxygen atom, a nitrogen atom and an oxygen atom, and the "nonaromatic heterocyclic group" is a nonaromatic 5- to 8-membered (monocyclic, bicyclic or tricyclic) heterocyclic group having, besides carbon atom, 1 to 3 kinds of 1 to 5 hetero atoms selected from an oxygen atom, a nitrogen atom and an oxygen atom. Examples of the "heterocyclic group" include 1-pyrrolyl, 2-pyrrolyl, 3-pyrrolyl, 1-imidazolyl, 2-imidazolyl, 4-imidazolyl, 5-imidazolyl, 1-pyrrolidinyl, 2-pyrrolidinyl, 3-pyrrolidinyl, pyrrolinyl, 1-imidazolidinyl, 2-imidazolidinyl, 3-imidazolidinyl, 4-imidazolidinyl, imidazolinyl, 2-pyridyl, 3-pyridyl, 4-pyridyl, pyrazinyl, 2-pyrimidinyl, 4-pyrimidinyl, 5-pyrimidinyl, 1-piperidyl, 2-piperidyl, 3-piperidyl, 4-piperidyl, 2-oxazolyl, 4-oxazolyl, 5-oxazolyl, 2-furyl, 3-furyl, 2-pyranyl, 3-pyranyl, 4-pyranyl, 5-pyranyl, 6-pyranyl, 1,3-dioxolan-2-yl, 1,3-dioxolan-4-yl, 1,4-dioxan-2-yl, 1,4-dioxan-3-yl and the like.

Examples of the "hydrocarbon group optionally having substituent(s)" for $Z^1$ or $Z^2$ include those similar to the "hydrocarbon group optionally having substituent(s)" for Y.

Examples of the "heterocyclic group optionally having substituent(s)" for $Z^1$ or $Z^2$ include those similar to the "heterocyclic group optionally having substituent(s)" for Y.

That $Z^1$ and $Z^2$ are joined to form, together with the adjacent phosphorus atom, a 4- to 8-membered ring optionally having substituent(s), is a compound represented by the following formula

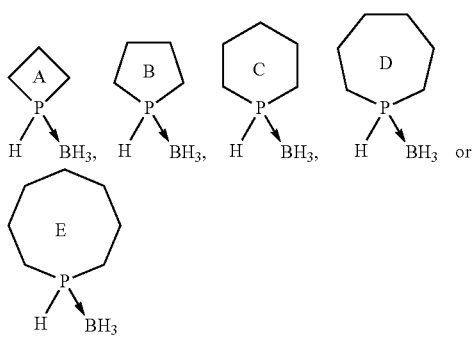

wherein ring A, ring B, ring C, ring D and ring E are optionally having substituent(s). In the above-mentioned formula, examples of the substituents which the ring may have include the aforementioned groups exemplified as the substituent of the "$C_{6-14}$ aryl group" for Y. They may have 1 to 3 substituents at substitutable position(s).

$Z^1$ and $Z^2$ is preferably a hydrocarbon group optionally having substituent(s), more preferably a $C_{6-14}$ aryl group optionally having substituent(s), further preferably a $C_{6-14}$ aryl group optionally substituted by 1 to 3 substituents selected from (1) a $C_{1-6}$ alkyl group, (2) a $C_{1-6}$ alkoxy group and (3) a di-$C_{1-6}$ alkylamino group. Furthermore, phenyl optionally substituted by 1 to 3 substituents selected from (1) a $C_{1-6}$ alkyl group and (2) a $C_{1-6}$ alkoxy group is preferable. More preferably, phenyl optionally substituted by 1 or 2 substituents selected from (1) a methyl group, (2) a tert-butyl group and (3) a methoxy group is preferable. Of these, phenyl having tert-butyl as a substituent is preferable.

$Z^1$ and $Z^2$ are most preferably p-tert-butylphenyl.

Examples of the leaving group for X include "optionally substituted alkylsulfonyloxy group" and "optionally substituted arylsulfonyloxy group".

Here, examples of the "optionally substituted alkylsulfonyloxy group" include a $C_{1-6}$ alkylsulfonyloxy group optionally substituted by 1 to 5 halogen atoms (fluorine, chlorine, bromine, iodine etc.); a methanesulfonyloxy group, an ethanesulfonyloxy group, a trifluoromethanesulfonyloxy group, a chloromethanesulfonyloxy group, a trichloromethanesulfonyloxy group, a nonafluorobutanesulfonyloxy and the like. Examples of the "optionally substituted arylsulfonyloxy group" include a $C_{6-10}$ arylsulfonyloxy group optionally substituted by 1 to 5 substituents selected from a halogen atom (fluorine, chlorine, bromine, iodine etc.), a $C_{1-6}$ alkyl group, a $C_{1-6}$ alkoxy group, a nitro group and a cyano group; a benzenesulfonyloxy group, a p-toluenesulfonyloxy group, a 1-naphthalenesulfonyloxy group, a 2-naphthalenesulfonyloxy group, a p-nitrobenzenesulfonyloxy group, a m-nitrobenzenesulfonyloxy group, a m-toluenesulfonyloxy group, a o-toluenesulfonyloxy group, a 4-chlorobenzenesulfonyloxy group, a 3-chlorobenzenesulfonyloxy group, a 4-methoxybenzenesulfonyloxy group and the like.

Preferred as X is a methanesulfonyloxy group, a trifluoromethanesulfonyloxy group, or a p-toluenesulfonyloxy group, and particularly preferred is a p-toluenesulfonyloxy group.

The "di-$C_{1-6}$ alkylamino group" for $R^3$ is a group composed of two "$C_{1-6}$ alkyl groups" and an amino group, and examples thereof include dimethylamino, diethylamino, dipropylamino, diisopropylamino, dibutylamino, N-ethyl-N-methylamino and the like.

$R^3$ is preferably a hydrogen atom or a $C_{1-6}$ alkyl group, most preferably tert-butyl.

$R^4$ is most preferably a hydrogen atom.

Examples of the "hydrocarbon group optionally having substituent(s)" for $R^5$, $R^6$ or $R^7$ include those similar to the "hydrocarbon group optionally having substituent(s)" for Y.

Examples of the "heterocyclic group optionally having substituent(s)" for $R^5$, $R^6$ or $R^7$ include those similar to the "hydrocarbon group optionally having substituent(s)" for Y.

Examples of the substituent of the "hydroxy group optionally having substituent(s)" for $R^5$, $R^6$ or $R^7$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-13}$ aralkyl group, and a $C_{8-13}$ arylalkenyl group, which have been recited as the "hydrocarbon group" of the "hydrocarbon group optionally having substituent(s)" for Y.

Examples of the substituent of the "sulfonyl group optionally having substituent(s)" for $R^5$, $R^6$ or $R^7$ include those similar to the substituents of the "hydroxy group optionally having substituent(s)".

Examples of the substituent of the "sulfinyl group optionally having substituent(s)" for $R^5$, $R^6$ or $R^7$ include those similar to the substituents of the "hydroxy group optionally having substituent(s)".

Examples of the substituent of the "thiol group optionally having substituent(s)" for $R^5$, $R^6$ or $R^7$ include those similar to the substituents of the "hydroxy group optionally having substituent(s)".

Examples of the acyl group for $R^5$, $R^6$ or $R^7$ include formyl group, acetyl group, propionyl group, butyryl group, isobutyryl group, valeryl group, isovaleryl group, pivaloyl group, cyclohexylcarbonyl group, benzoyl group, toluoyl group (o-, m-, p-), cinnamoyl group, naphthoyl group (1-, 2-) and the like.

The alkoxycarbonyl group of the "alkoxycarbonyl group optionally having substituent(s)" for $R^5$, $R^6$ or $R^7$ is a $C_{1-14}$ alkoxycarbonyl group, and examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl, phenoxycarbonyl, allyloxycarbonyl, benzyloxycarbonyl and 9-fluorenylmethyloxycarbonyl.

Examples of the "substituent" of the "alkoxycarbonyl group optionally having substituent(s)" include those similar to the substituents of the "hydroxy group optionally having substituent(s)" for $R^5$, $R^6$ or $R^7$.

Examples of the "substituent" of the "carbamoyl group optionally having substituent(s)" for $R^5$, $R^6$ or $R^7$ include (1) a $C_{1-10}$ alkyl group, (2) a $C_{2-10}$ alkenyl group, (3) a $C_{3-10}$ cycloalkyl group, (4) a $C_{3-10}$ cycloalkenyl group, (5) a $C_{4-10}$ cycloalkadienyl group, (6) a $C_{6-14}$ aryl group, (7) a $C_{7-13}$ aralkyl group, (8) a $C_{7-13}$ arylalkenyl group, (9) an acyl group, (10) a $C_{1-14}$ alkoxy-carbonyl group and the like. While the number of the substituents is 1 or 2, when the number of the substituents is 2, the respective substituents may be the same or different.

Examples of the above-mentioned "$C_{1-10}$ alkyl group", "$C_{2-10}$ alkenyl group", "$C_{3-10}$ cycloalkyl group", "$C_{3-10}$ cycloalkenyl group", "$C_{4-10}$ cycloalkadienyl group", "$C_{6-14}$ aryl group", "$C_{7-13}$ aralkyl group", and "$C_{8-13}$ arylalkenyl group" include those similar to the "$C_{1-10}$ alkyl group", "$C_{2-10}$ alkenyl group", "$C_{3-10}$ cycloalkyl group", "$C_{3-10}$ cycloalkenyl group", "$C_{4-10}$ cycloalkadienyl group", "$C_{6-14}$ aryl group", "$C_{7-13}$ aralkyl group", and "$C_{8-13}$ arylalkenyl group" exemplified as the "hydrocarbon group" of the "hydrocarbon group optionally having substituent(s)" for Y.

As the "acyl group" as the substituent of the "carbamoyl group optionally having substituent(s)", those similar to the "acyl group" for $R^5$, $R^6$ or $R^7$ can be mentioned.

As the "$C_{1-14}$ alkoxy-carbonyl group" as the substituent of the "carbamoyl group optionally having substituent(s)", those similar to the "$C_{1-14}$ alkoxy-carbonyl group" exemplified as the "alkoxycarbonyl group" of the "alkoxycarbonyl group optionally having substituent(s)" for $R^5$, $R^6$ or $R^7$ can be mentioned.

Examples of the "hydrocarbon group optionally having substituent(s)" for $R^8$ or $R^9$ include those similar to the "hydrocarbon group optionally having substituent(s)" for Y.

Examples of the "heterocyclic group optionally having substituent(s)" for $R^8$ or $R^9$ include those similar to the "heterocyclic group optionally having substituent(s)" for Y.

Examples of the "acyl group" for $R^8$ or $R^9$ include those similar to the "acyl group" for $R^5$, $R^6$ or $R^7$.

Examples of the substituent of the "sulfonyl group optionally having substituent(s)" for $R^8$ or $R^9$ include those similar to the substituents of the "hydroxy group optionally having substituent(s)". Examples of the substituent of the "silyl group optionally having substituent(s)" for $R^8$ or $R^9$ include those similar to the substituents of the "hydroxy group optionally having substituent(s)". The number of the substituents may be 1 to 3. When the number of the substituents is two or more, the respective substituents may be the same or different.

$R^5$ and $R^6$ are joined to form, together with the adjacent atom, a 4- to 8-membered ring optionally having substituent(s), which means, for example, a compound represented by the following formula

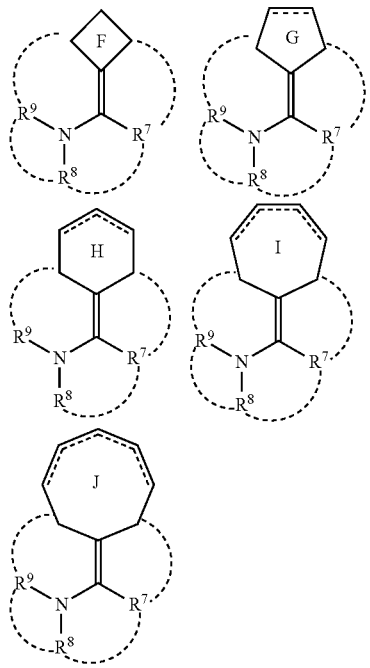

wherein ring F, ring G, ring H, ring I and ring J optionally have substituent(s), the broken line part may be a double bond (may be fused with a benzene ring via a double bond in the broken line part), and $R^7$, $R^8$, and $R^9$ are as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

$R^6$ and $R^7$ are joined to form, together with the adjacent atom, a 4- to 8-membered ring optionally having substituent(s), which means, for example, a compound represented by the following formula

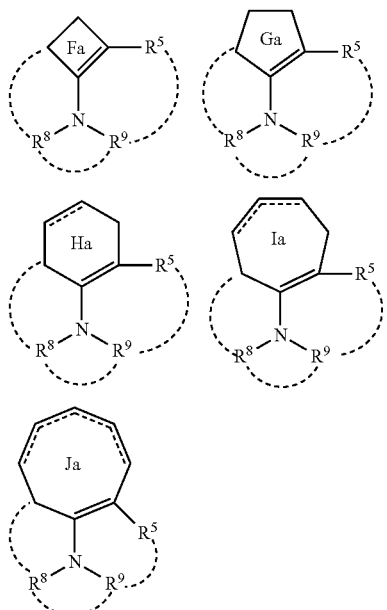

wherein ring Fa, ring Ga, ring Ha, ring Ia and ring Ja optionally have substituent(s), the broken line part may be a double bond (may be fused with a benzene ring via a double bond in the broken line part), and $R^5$, $R^8$ and $R^9$ are as defined above. In the above-mentioned formula, examples of the substituent that the ring optionally has include the groups recited as the substituent of the "$C_{6-14}$ aryl group", which optionally have 1 to 3 substituents at substitutable position(s).

In addition, $R^6$ and $R^7$ are joined to form, together with the adjacent atom, a 4- to 8-membered ring optionally having substituent(s), which means, for example, a compound represented by the following formula

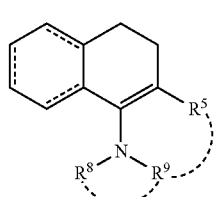 (R-1)

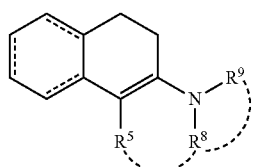 (R-2)

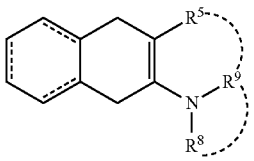

(R-3)

wherein ring R-1, ring R-2 and ring R-3 optionally have substituent(s), the broken line part may be a double bond (may be fused with a benzene ring via a double bond in the broken line part), and $R^5$, $R^8$, and $R^9$ are as defined above. In the above-mentioned formula, examples of the substituent that the ring optionally has include the groups recited as the substituent of the "$C_{6-14}$ aryl group", which optionally have 1 to 3 substituents at substitutable position(s).

$R^7$ and $R^8$ are joined to form, together with the adjacent atom, a 4- to 8-membered ring optionally having substituent(s), which means, for example, the following formula

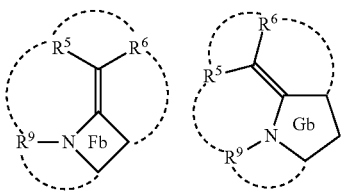

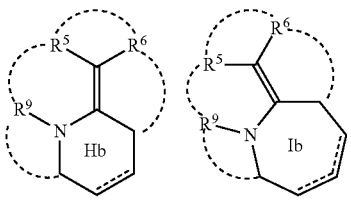

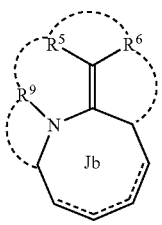

wherein ring Fb, ring Gb, ring Hb, ring Ib and ring Jb optionally have substituent(s), the broken line part may be a double bond (may be fused with a benzene ring via a double bond in the broken line part), and $R^5$, $R^6$, and $R^9$ are as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

$R^8$ and $R^9$ are joined to form, together with the adjacent atom, a 4- to 8-membered ring optionally having substituent(s), which means, for example, the following formula

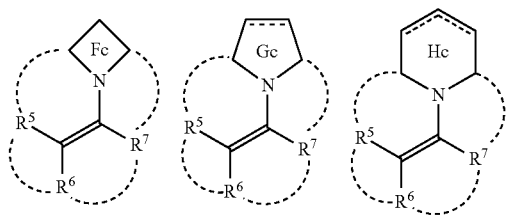

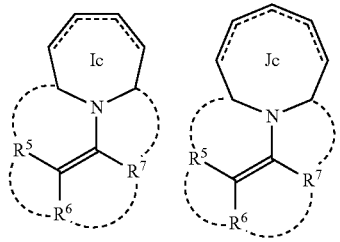

wherein ring Fc, ring Gc, ring Hc, ring Ic and ring Jc optionally have substituent(s), the broken line part may be a double bond (may be fused with a benzene ring via a double bond in the broken line part), and $R^5$, $R^6$, and $R^7$ are as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

$R^9$ and $R^5$ are joined to form, together with the adjacent atom, a 4- to 8-membered ring optionally having substituent(s), which means, for example, a compound represented by the following formula

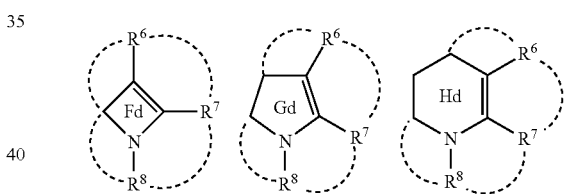

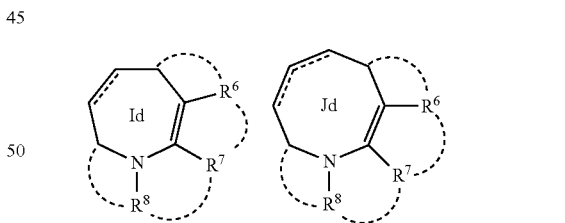

wherein ring Fd, ring Gd, ring Hd, ring Id and ring Jd optionally have substituent(s), the broken line part may be a double bond (may be fused with a benzene ring via a double bond in the broken line part), and $R^6$, $R^7$, and $R^8$ are as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

In addition, $R^9$ and $R^5$ are joined to form, together with the adjacent atom, a 4- to 8-membered ring optionally having substituent(s), which means, for example, a compound represented by the following formula (Q-1)

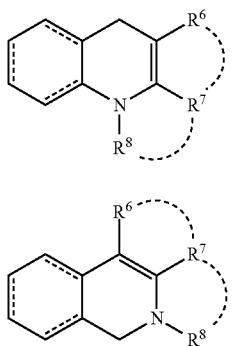

(Q-2)

wherein ring Q-1 and ring Q-2 optionally have substituent(s), the broken line part may be a double bond (may be fused with a benzene ring via a double bond in the broken line part), and $R^6$, $R^7$, and $R^8$ are as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

When $R^5$ is a carbamoyl group optionally having substituent(s), it may be joined with $R^6$ to form a 4- to 8-membered ring together with the adjacent carbon atom, which is, for example, a compound represented by the following formula

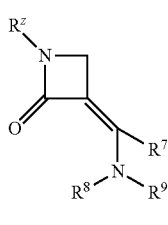

(W-1)

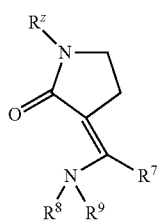

(W-2)

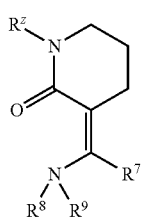

(W-3)

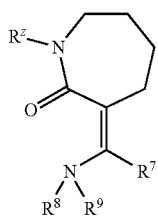

(W-4)

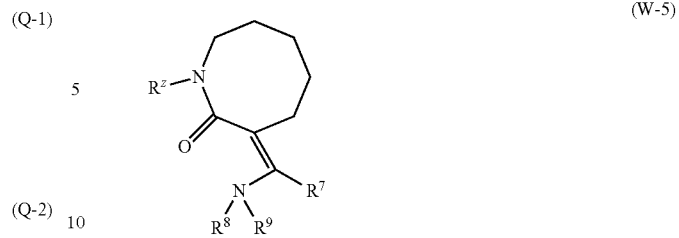

(W-5)

wherein $R^7$, $R^8$, and $R^9$ are as defined above, and $R^Z$ is (1) a $C_{1-10}$ alkyl group, (2) a $C_{2-10}$ alkenyl group, (3) a $C_{3-10}$ cycloalkyl group, (4) a $C_{3-10}$ cycloalkenyl group, (5) a $C_{4-10}$ cycloalkadienyl group, (6) a $C_{6-14}$ aryl group, (7) a $C_{7-13}$ aralkyl group, (8) a $C_{8-13}$ arylalkenyl group, (9) an acyl group, (10) a $C_{1-14}$ alkoxy-carbonyl group or (11) a hydrogen atom. As each group for $R^Z$, those similar to the substituents of the "carbamoyl group optionally having substituent(s)" for $R^5$, $R^6$ or $R^7$ can be mentioned.

$R^5$ and $R^6$ are each preferably a hydrogen atom, a hydrocarbon group optionally having substituent(s), a heterocyclic group optionally having substituent(s), an acyl group, an alkoxycarbonyl group optionally having substituent(s), a carboxyl group, or a carbamoyl group optionally having substituent(s), more preferably, a hydrogen atom, a hydrocarbon group optionally having substituent(s) or a carbamoyl group optionally having substituent(s), among others, a hydrogen atom, a $C_{1-6}$ alkyl group, phenyl, or a carbamoyl group optionally having substituent(s) is preferable, particularly, a hydrogen atom, a $C_{1-6}$ alkyl group, or a carbamoyl group optionally substituted by a $C_{1-14}$ alkoxy-carbonyl group.

$R^7$ is preferably a hydrogen atom, a hydrocarbon group optionally having substituent(s), a heterocyclic group optionally having substituent(s), an acyl group, an alkoxycarbonyl group optionally having substituent(s), a carboxyl group, or a carbamoyl group optionally having substituent(s), more preferably, a hydrogen atom, a hydrocarbon group optionally having substituent(s) or an alkoxycarbonyl group optionally having substituent(s). Among these, methyl substituted by a $C_{1-6}$ alkyl group, or a $C_{1-6}$ alkoxycarbonyl group is preferable.

$R^8$ and $R^9$ are each preferably a hydrogen atom, a hydrocarbon group optionally having substituent(s) or an acyl group. Among these, a hydrogen atom, phenyl wherein the para-position is optionally substituted by (1) a halogen atom or (2) methoxy, or acetyl is preferable.

More preferably, $R^5$ is a carbamoyl group optionally having substituent(s), and further preferably joined with $R^6$ to form a 4- to 8-membered ring together with the adjacent carbon atom, and the above-mentioned compound (W-2) is more preferable. Among these, compound (W-2) wherein $R^Z$ is selected from (1) tert-butoxycarbonyl, (2) allyloxycarbonyl, (3) benzyloxycarbonyl, and (4) 9-fluorenylmethyloxycarbonyl, $R^7$ is methoxymethyl, one of $R^8$ and $R^9$ is a hydrogen atom, and one of $R^8$ and $R^9$ is phenyl optionally substituted by (1) a halogen atom or (2) methoxy at the para-position is preferable. Most preferred is benzyl 3-(2-methoxy-1-(phenylamino)ethylidene)-2-oxopyrrolidine-1-carboxylate.

Examples of the "hydrocarbon group optionally having substituent(s)" for $R^a$ or $R^b$ include those similar to the "hydrocarbon group optionally having substituent(s)" for $R^5$, $R^6$ or $R^7$.

Examples of the "heterocyclic group optionally having substituent(s)" for $R^a$ or $R^b$ include those similar to the "heterocyclic group optionally having substituent(s)" for $R^5$, $R^6$ or $R^7$.

Examples of the "hydroxy group optionally having substituent(s)" for $R^a$ or $R^b$ include those similar to the "hydroxy group optionally having substituent(s)" for $R^5$, $R^6$ or $R^7$.

Examples of the "acyl group" for $R^a$ or $R^b$ include those similar to the "acyl group" for $R^5$, $R^6$ or $R^7$.

Examples of the "sulfonyl group optionally having substituent(s)" for $R^a$ or $R^b$ include those similar to the "sulfonyl group optionally having substituent(s)" for $R^5$, $R^6$ or $R^7$.

Examples of the "sulfinyl group optionally having substituent(s)" for $R^a$ or $R^b$ include those similar to the "sulfinyl group optionally having substituent(s)" for $R^5$, $R^6$ or $R^7$. Examples of the "thiol group optionally having substituent(s)" for $R^a$ or $R^b$ include those similar to the "thiol group optionally having substituent(s)" for $R^5$, $R^6$ or $R^7$.

Examples of the "hydrocarbon group optionally having substituent(s)" for $R^c$ include those similar to the "hydrocarbon group optionally having substituent(s)" for $R^8$ or $R^9$.

Examples of the "heterocyclic group optionally having substituent(s)" for $R^c$ include those similar to the "heterocyclic group optionally having substituent(s)" for $R^8$ or $R^9$.

Examples of the "acyl group" for $R^c$ include those similar to the "acyl group" for $R^5$, $R^6$ or $R^7$.

As the substituent of the "amino group optionally having substituent(s)" for $R^c$, those similar to the substituent of the "carbamoyl group optionally having substituent(s)" for $R^5$, $R^6$ or $R^7$ can be mentioned. While the number of the substituents is 1 or 2, when the number of the substituents is 2, the respective substituents may be the same or different.

Examples of the "sulfonyl group optionally having substituent(s)" for $R^c$ include those similar to the "sulfonyl group optionally having substituent(s)" for $R^5$, $R^6$ or $R^7$.

Examples of the "silyl group optionally having substituent(s)" for $R^c$ include those similar to the "silyl group optionally having substituent(s)" for $R^8$ or $R^9$.

$R^a$ and $R^b$ are joined to form, together with the adjacent atom, a 4- to 8-membered ring optionally having substituent(s) means, for example, a compound represented by the following formula

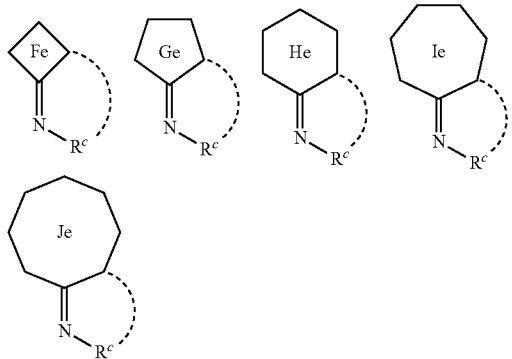

wherein $R^c$ is as defined above. In the above-mentioned formula, examples of the substituent that the ring optionally has include the groups recited as the substituent of the "$C_{6-14}$ aryl group", which optionally have 1 to 3 substituents at substitutable position(s). In addition, $R^a$ and $R^b$ are joined to form, together with the adjacent atom, a 4- to 8-membered ring optionally having substituent(s), which means, for example, a compound represented by the following formula

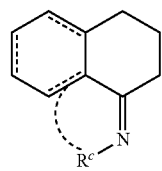 (S-1)

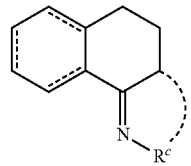 (S-2)

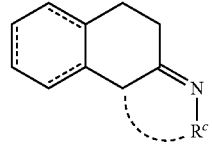 (S-3)

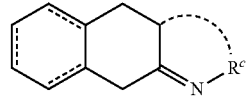 (S-4)

wherein ring S-1, ring S-2, ring S-3, and ring S-4 optionally have substituent(s), the broken line part may be a double bond (may be fused with a benzene ring via a double bond in the broken line part), and $R^c$ is as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

In addition, $R^a$ and $R^b$ are joined to form, together with the adjacent atom, a 4- to 8-membered ring optionally having substituent(s), which means, for example, a compound represented by the following formula

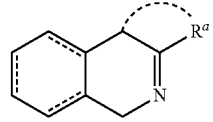 (T-1)

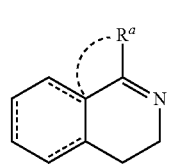 (T-2)

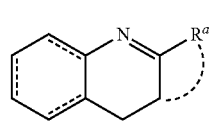 (T-3)

wherein ring T-1, ring T-2, and ring T-3 optionally have substituent(s), the broken line part may be a double bond (may be fused with a benzene ring via a double bond in the broken line part), and $R^a$ is as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

$R^b$ and $R^c$ are joined to form, together with the adjacent atom, a 4- to 8-membered ring optionally having substituent(s), which means, for example, a compound represented by the following formula

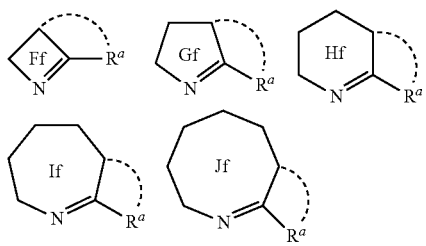

wherein $R^a$ is as defined above. As the substituent that the ring optionally has in the above-mentioned formulas, the groups recited as the substituent of the "$C_{6-14}$ aryl group" can be mentioned, which optionally have 1 to 3 substituents at substitutable position(s).

$R^a$ and $R^b$ are each preferably a hydrogen atom, a hydrocarbon group optionally having substituent(s) or an acyl group, more preferably a hydrocarbon group optionally having substituent(s), further preferably a $C_{1-6}$ alkyl group optionally having 1 to 3 substituents selected from (1) a $C_{1-6}$ alkoxy group and (2) a mono-$C_{1-6}$ alkylamino group, or a $C_{6-14}$ aryl group optionally having 1 to 3 substituents selected from (1) a $C_{1-6}$ alkoxy group, (2) a mono-$C_{1-6}$ alkylamino group, (3) a halogen atom and (4) a $C_{1-6}$ alkyl group.

$R^C$ is preferably a hydrogen atom, a hydrocarbon group optionally having substituent(s), an amino group optionally having substituent(s), or an acyl group. More preferably, $R^C$ is an amino group optionally having substituent(s). As the "substituent" of the amino group optionally having substituent(s) for $R^C$, an acyl group is preferable, and one substitution is preferable. Most preferably, the aforementioned "acyl group" is a benzoyl group.

Most preferably, $R^a$ and $R^b$ are each methyl or phenyl, and $R^C$ is an amino group substituted by one benzoyl.

In the present invention, examples of the "alkyl group" of the "alkyl group optionally having substituent(s)" for R' or R" include those similar to the "$C_{1-10}$ alkyl group" recited as the "hydrocarbon group" of the "hydrocarbon group optionally having substituent(s)" for Y, and examples of the "substituent" of the "alkyl group optionally having substituent(s)" for R' or R" include those similar to the "$C_{1-10}$ alkyl group" recited as the "substituent" of the "hydrocarbon group optionally having substituent(s)" for Y. In the present invention, examples of the "alkyl group optionally having substituent(s)" for R'" or R"" include those similar to the "hydrocarbon group" of the "hydrocarbon group optionally having substituent(s)" for R' or R". R'" and R"" are joined to form, together with the adjacent atom, a 4- to 9-membered ring optionally having substituent(s), which means, for example, a compound represented by the following formula

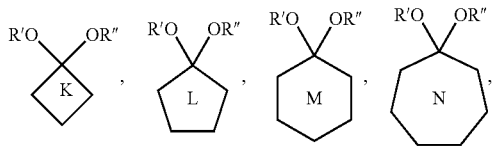

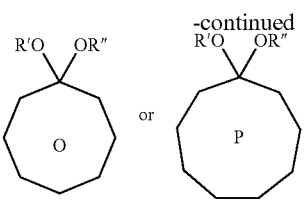

wherein ring K, ring L, ring M, ring N, ring O and ring P optionally have substituent(s), R' and R" are as defined above. In the above-mentioned formula, examples of the substituent that the ring optionally has include the groups recited as the substituent of the "$C_{6-14}$ aryl group", which optionally have 1 to 3 substituents at substitutable position(s). A preferable scope of the "substituent" includes a $C_{1-6}$ alkyl group optionally substituted by 1 to 3 halogen atoms, a hydroxy group, a $C_{1-6}$ alkoxy group, a halogen atom, more preferably a $C_{1-6}$ alkyl group optionally substituted by 1 to 3 halogen atoms.

In the present invention, a preferable scope of R' includes a $C_{1-10}$ alkyl group optionally having 1 to 3 substituents selected from (1) nitro, (2) nitroso and (3) cyano, more preferably a $C_{1-6}$ alkyl group.

In the present invention, a preferable scope of R" includes a $C_{1-10}$ alkyl group optionally having 1 to 3 substituents selected from (1) nitro, (2) nitroso and (3) cyano, more preferably a $C_{1-6}$ alkyl group.

In the present invention, a preferable scope of R'" includes a $C_{1-10}$ alkyl group optionally having 1 to 3 substituents selected from (1) nitro, (2) nitroso and (3) cyano, more preferably a $C_{1-6}$ alkyl group.

In the present invention, a preferable scope of R"" includes a $C_{1-10}$ alkyl group optionally having 1 to 3 substituents selected from (1) nitro, (2) nitroso and (3) cyano, more preferably a $C_{1-6}$ alkyl group.

Preferably, R', R", R'" and R"" are $C_{1-4}$ alkyl groups, more preferably, R', R", R'" and R"" are methyl.

In the present invention, examples of the "aromatic compound having a hydroxy group" include phenol, 4-bromophenol, 4-benzylphenol, 2-benzylphenol, 4-methoxyphenol, 3-methoxyphenol, 2-methoxyphenol, 4-ethyl-2-methoxyphenol, BINOL, para-hydroxybenzophenone, benzhydrol, salicyl alcohol, cresol, xylenol, naphthol, catechol, resorcinol, hydroquinone, pyrogallol, phloroglucinol, 1,2,4-benzenetriol, flopropione, biphenyl-4,4'-diol, 3-hydroxypyridine, and cyanuric acid. Preferably, the "aromatic compound having a hydroxy group" is "a benzene ring having 2 or 3 hydroxy groups", more preferably 4-bromophenol, 4-methoxyphenol, salicyl alcohol and cyanuric acid, most preferably cyanuric acid.

While an embodiment of the present invention is explained in detail below, the described contents do not limit the present invention.

The resultant product and intermediate obtained in the reactions can be directly used in the next reaction. Where necessary, they can also be isolated from the reaction mixture according to a conventional method, and can be easily purified by a separation means such as recrystallization, distillation, chromatography and the like.

(Production Method of Amine Compound)

An amine compound can be produced by a method including a hydrogenation reaction of enamine [Method A-1] or a method including a hydrogenation reaction of imine [Method A-2], shown below.

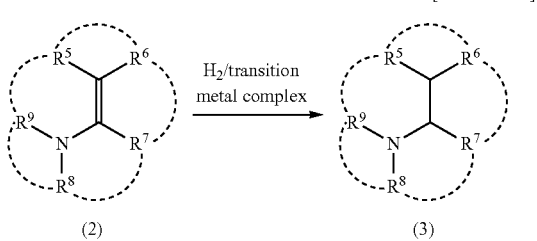

[Method A-1]

(2) → (3)

wherein each symbol is as defined above.

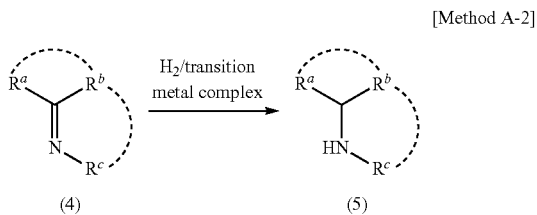

[Method A-2]

(4) → (5)

wherein each symbol is as defined above.

In the above-mentioned [Method A-1] and [Method A-2], a transition metal complex is used as a catalyst. The activity of catalyst is often low and, in a preferable embodiment of the present invention, the reaction is performed in the presence of the aforementioned "aromatic compound having a hydroxy group". The "aromatic compound having a hydroxy group" may be added in advance before starting the reaction, or added in the course of reaction. The amount to be added is preferably 0.01-100 equivalents, more preferably 0.1-10 equivalents.

In any reaction, a transition metal complex is used as a catalyst. However, since the catalyst is easily decomposed by water present in the reaction system, in a preferable embodiment of the present invention, the reaction is performed in the presence of a compound represented by the formula (6)

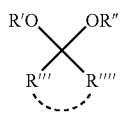

(6)

wherein each symbol is as defined above. A compound represented by the formula (6) may be added in advance before starting the reaction, or added in the course of reaction. In the compound represented by the formula (6), a preferable scope of R', R'', R''' and R'''' is as mentioned above, examples of the formula (6) include acetals such as 2,2-dimethoxypropane, 2,2-diethoxypropane and the like, preferably 2,2-dimethoxypropane.

The amount to be added is preferably 0.01-100 equivalents, more preferably 0.1-10 equivalents.

Examples of the "transition metal" of the "transition metal complex" used as a catalyst in [Method A-1] or [Method A-2] include rhodium, ruthenium, iridium, palladium, nickel, cobalt, platinum, iron, gold, silver and copper. Of these, rhodium, ruthenium, iridium, palladium, nickel and copper are preferable, rhodium, ruthenium and iridium are particularly preferable.

As the "transition metal complex", a compound wherein the aforementioned "transition metal" is coordinated with a "ligand" is used. Examples of the "ligand" include diphosphine ligand, diamine ligand and the like.

More specific examples of the "transition metal complex" include rhodium complex, ruthenium complex, iridium complex, palladium complex, nickel complex and copper complex, examples of each of which are shown below (In the following transition metal complexes, L is a diphosphine ligand, Ar is benzene optionally having substituent(s) (substituent is preferably a $C_{1-6}$ alkyl group), Cp* is pentamethylcyclopentadienyl, Cp is cyclopentadienyl, cod is 1,5-cyclooctadiene, Tf is trifluoromethanesulfonyl, nbd is norbornadiene, Ph is phenyl, Ac is acetyl, Et is ethyl, dmf is N,N-dimethylformamide, 2-methylallyl is $\eta^3$-2-methylallyl, en is ethylenediamine, dpen is 1,2-diphenylethylenediamine, daipen is 1,1-di(4-anisyl)-2-isopropyl-1,2-ethylenediamine, and n is an integer of one or more. While 1,2-diphenylethylenediamine and 1,1-di(4-anisyl)-2-isopropyl-1,2-ethylenediamine contain an (R) form, (S) form and a mixture of (R) form and (S) form (ratio of the both is not limited), an optically active form is preferable.

Rhodium complex: $[RhCl(L)]_2$, $[RhBr(L)]_2$, $[RhI(L)]_2$, $[RhCp^*(L)]_2$, $[Rh(cod)(L)]OTf$, $[Rh(cod)(L)]BF_4$, $[Rh(cod)(L)]ClO_4$, $[Rh(cod)(L)]PF_6$, $[Rh(cod)(L)]BPh_4$, $[Rh(nbd)(L)]OTf$, $[Rh(nbd)(L)]BF_4$, $[Rh(nbd)(L)]ClO_4$, $[Rh(nbd)(L)]PF_6$, $[Rh(nbd)(L)]BPh_4$, $[Rh(L)(CH_3OH)_2]OTf$, $[Rh(L)(CH_3OH)_2]BF_4$, $[Rh(L)(CH_3OH)_2]ClO_4$, $[Rh(L)(CH_3OH)_2]PF_6$, $[Rh(L)(CH_3OH)_2]BPh_4$ Ruthenium complex: $[RuCl_2(L)]_n$, $[RuBr_2(L)]_n$, $[RuI_2(L)]_n$, $[Ru(OAc)_2(L)]$, $[Ru(O_2CCF_3)_2(L)]$, $(NH_2Me_2)[\{RuCl(L)\}_2(\mu\text{-Cl})_3]$, $(NH_2Et_2)[\{RuCl(L)\}_2(\mu\text{-Cl})_3]$, $(NH_2Me_2)[\{RuBr(L)\}_2(\mu\text{-Br})_3]$, $(NH_2Et_2)[\{RuBr(L)\}_2(\mu\text{-Br})_3]$, $(NH_2Me_2)[\{RuI(L)\}_2(\mu\text{-I})_3]$, $(NH_2Et_2)[\{RuI(L)\}_2(\mu\text{-I})_3]$, $[Ru_2Cl_4(L)_2(NEt_3)]$, $[RuCl_2(L)(dmf)_n]$, $[Ru(2\text{-methylallyl})_2(L)]$, $[RuCl(Ar)(L)]Cl$, $[RuCl(Ar)(L)]Br$, $[RuCl(Ar)(L)]I$, $[RuCl(Ar)(L)]OTf$, $[RuCl(Ar)(L)]ClO_4$, $[RuCl(Ar)(L)]PF_6$, $[RuCl(Ar)(L)]BF_4$, $[RuCl(Ar)(L)]BPh_4$, $[RuBr(Ar)(L)]Cl$, $[RuBr(Ar)(L)]Br$, $[RuBr(Ar)(L)]I$, $[RuI(Ar)(L)]Cl$, $[RuI(Ar)(L)]Br$, $[RuI(Ar)(L)]I$, $[Ru(L)](OTf)_2$, $[Ru(L)](BF_4)_2$, $[Ru(L)](ClO_4)_2$, $[Ru(L)](PF_6)_2$, $[Ru(L)](BPh_4)_2$, $[RuH(L)_2]Cl$, $[RuH(L)_2]OTf$, $[RuH(L)_2]BF_4$, $[RuH(L)_2]ClO_4$, $[RuH(L)_2]PF_6$, $[RuH(L)_2]BPh_4$, $[RuH(CH_3CN)(L)]Cl$, $[RuH(CH_3CN)(L)]OTf$, $[RuH(CH_3CN)(L)]BF_4$, $[RuH(CH_3CN)(L)]ClO_4$, $[RuH(CH_3CN)(L)]PF_6$, $[RuH(CH_3CN)(L)]BPh_4$, $[RuCl(L)]OTf$, $[RuCl(L)]BF_4$, $[RuCl(L)]ClO_4$, $[RuCl(L)]PF_6$, $[RuCl(L)]BPh_4$, $[RuBr(L)]OTf$, $[RuBr(L)]BF_4$, $[RuBr(L)]ClO_4$, $[RuBr(L)]PF_6$, $[RuBr(L)]BPh_4$, $[RuI(L)]OTf$, $[RuI(L)]BF_4$, $[RuI(L)]ClO_4$, $[RuI(L)]PF_6$, $[RuI(L)]BPh_4$, $[RuCl_2(L)(en)]$, $[RuCl_2(L)(dpen)]$, $[RuCl_2(L)(daipen)]$, $[RuH(\eta^1\text{-}BH_4)(L)(en)]$, $[RuH(\eta^1\text{-}BH_4)(L)(daipen)]$, $[RuH(\eta 1\text{-}BH_4)(L)(dpen)]$ (Examples of the diamine ligand corresponding to en, dpen and daipen, which are diamine ligands in the aforementioned $[RuCl_2(L)(en)]$, $[RuCl_2(L)(dpen)]$ and $[RuCl_2(L)(daipen)]$ include, besides these, 1,2-cyclohexanediamine, 1,2-cycloheptanediamine, 2,3-dimethylbutanediamine, 1-methyl-2,2-diphenyl-1,2-ethylenediamine, 1-isobutyl-2,2-diphenyl-1,2-ethylenediamine, 1-isopropyl-2,2-diphenyl-1,2-ethylenediamine, 1,1-di(4-anisyl)-2-methyl-1,2-ethylenediamine, 1,1-di(4-anisyl)-2-isobutyl-1,2-ethylenediamine, 1,1-di(4-anisyl)-2-benzyl-1,2-ethylenediamine, 1-methyl-2,2-dinaphthyl-1,2-ethylenediamine, 1-isobutyl-2,2-dinaphthyl-1,2-ethylenediamine, 1-isopropyl-2,2-dinaphthyl-1,2-ethylenediamine, propanediamine, butanediamine, phenylenediamine and the like.)

Iridium complex: [IrCl(L)]$_2$, [IrBr(L)]$_2$, [IrI(L)]$_2$, [IrCp*(L)]$_2$, [Ir(cod)(L)]OTf, [Ir(cod)(L)]BF$_4$, [Ir(cod)(L)]ClO$_4$, [Ir(cod)(L)]PF$_6$, [Ir(cod)(L)]BPh$_4$, [Ir(nbd)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$ Palladium complex: [PdCl$_2$(L)], [PdBr$_2$(L)], [PdI$_2$(L)], [Pd(n-allyl)(L)]Cl, [Pd(n-allyl)(L)]OTf, [Pd(n-allyl)(L)]BF$_4$, [Pd(n-allyl)(L)]ClO$_4$, [Pd(n-allyl)(L)]PF$_6$, [Pd(n-allyl)(L)]BPh$_4$, [Pd(L)](OTf)$_2$, [Pd(L)](BF$_4$)$_2$, [Pd(L)](ClO$_4$)$_2$, [Pd(L)](PF$_6$)$_2$, [Pd(L)](BPh$_4$)$_2$, [Pd(L)$_2$], [Pd(L)(H$_2$O)$_2$](OTf)$_2$, [Pd(L)(H$_2$O)$_2$](BF$_4$)$_2$, [Pd(L)(H$_2$O)$_2$](ClO$_4$)$_2$, Pd(L)(H$_2$O)$_2$](PF$_6$)$_2$, [Pd(L)(H$_2$O)$_2$](BPh$_4$)$_2$, [{Pd(L)}$_2$(µ-OH)$_2$](OTf)$_2$, [{Pd(L)}$_2$(µ-OH)$_2$](BF$_4$)$_2$, [{Pd(L)}$_2$(µ-OH)$_2$](ClO$_4$)$_2$, [{Pd(L)}$_2$(—OH)$_2$](PF$_6$)$_2$, [{Pd(L)}$_2$(µ-OH)$_2$](BPh$_4$)$_2$ Nickel complex: [NiCl$_2$ (L)], [NiBr$_2$(L)], [NiI$_2$(L)], [Ni(π-allyl)(L)]Cl, [Ni(cod)(L)], [Ni(nbd)(L)]

Copper complex: [CuCl(L)], [CuBr(L)], [CuI(L)], [CuH(L)], [Cu(η$^1$-BH$_4$)(L)], [Cu(Cp)(L)], [Cu(Cp*)(L)], [Cu(L)(CH$_3$CN)$_2$]OTf, [Cu(L)(CH$_3$CN)$_2$]BF$_4$, [Cu(L)(CH$_3$CN)$_2$]ClO$_4$, [Cu(L)(CH$_3$CN)$_2$]PF$_6$, [Cu(L)(CH$_3$CN)$_2$]BPh$_4$ Examples of the above-mentioned diphosphine ligand for L include 2,2'-bis-(diphenylphosphino)-1,1'-binaphthyl (hereinafter sometimes to be abbreviated as BINAP); BINAP derivative wherein the naphthyl ring of BINAP has a substituent such as C$_{1-6}$ alkyl group, C$_{6-14}$ aryl group and the like, e.g., 2,2'-bis-(diphenylphosphino)-6,6'-dimethyl-1,1'-binaphthyl; BINAP derivative wherein the naphthyl ring of BINAP is partially hydrogenated, e.g., 2,2'-bis-(diphenylphosphino)-5,6,7,8,5',6',7',8'-octahydro-1,1'-binaphthyl (H8 BINAP); BINAP derivative wherein one benzene ring on phosphorus atom of BINAP has 1 to 5 substituents such as a C$_{1-6}$ alkyl group and the like, e.g., 2,2'-bis-(di-p-tolylphosphino)-1,1'-binaphthyl (tol-BINAP), 2,2'-bis[bis(3,5-dimethylphenyl)phosphino]-1,1'-binaphthyl (xyl-BINAP), 2,2'-bis[bis(3,5-diethylphenyl)phosphino]-1,1'-binaphthyl, 2,2'-bis[bis(3,5-diisopropylphenyl)phosphino]-1,1'-binaphthyl, 2,2'-bis(3,5-di-tert-butylphenyl)phosphino]-1,1'-binaphthyl, 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl and 2,2'-bis[bis[4-(pyrrolidin-1-yl)phenyl]phosphino]-1,1'-binaphthyl, 2,2'-bis-(di-p-methoxyphenylphosphino)-1,1'-binaphthyl, 2,2'-bis[bis(3,5-dimethyl-4-methoxyphenyl)phosphino]-1,1'-binaphthyl, 2,2'-bis[bis(3,5-di-tert-butyl-4-methoxyphenyl)phosphino]-1,1'-binaphthyl (DTBM-BINAP); 2,2'-bis(dicyclohexylphosphino)-6,6'-dimethyl-1,1'-biphenyl (BICHEP), 2,2'-bis(diphenylphosphino)-6,6'-dimethoxybiphenyl (MeO-BIPHEP), 2,3-bis(diphenylphosphino)butane (CHIRAPHOS), 1-cyclohexyl-1,2-bis(diphenylphosphino)ethane (CYCPHOS), 1,2-bis[(2-methoxyphenyl)phenylphosphino]ethane (DIPAMP), 1,2-bis(diphenylphosphino)propane (PROPHOS), 2,4-bis(diphenylphosphino)pentane (SKEWPHOS), SKEWPHOS derivative wherein one benzene ring on phosphorus atom of SKEWPHOS has 1 to 5 substituents such as a C$_{1-6}$ alkyl group and the like, e.g., 1-[1',2-bis(diphenylphosphino)ferrocenyl]ethylenediamine (BPPFA), 1-substituted-3,4-bis(diphenylphosphino)pyrrolidine (DEGPHOS), 2,3-O-isopropylidene-2,3-dihydroxy-1,4-bis(diphenylphosphino)butane (DIOP), substitution-1,2-bisphospholanobenzene (DuPHOS), substituted-1,2-bisphospholanoethane (BPE), 5,6-bis(diphenylphosphino)-2-norbornane (NORPHOS), N,N'-bis(diphenylphosphino)-N,N'-bis(1-phenylethyl)ethylenediamine (PNNP), 2,2'-diphenylphosphino-1,1'-bicyclopentyl (BICP), 4,12-bis(diphenylphosphino)-[2,2]-paracyclophane (PhanePHOS), N-substituted-N-diphenylphosphino-1-[2-(diphenylphosphino)ferrocenyl]ethylamine (BoPhoz), 1-[2-(phosphino)ferrocenyl]ethyl-disubstituted phosphine (Josiphos), 1-[2-(2'-disubstituted phosphinophenyl)ferrocenyl]ethyl-disubstituted phosphine (Walphos), 2,2'-bis(α-N,N-dimethylaminophenylmethyl)-1,1'-bis(disubstituted phosphino)ferrocene (Mandyphos), disubstituted phosphino-2-[α-(N,N-dimethylamino)-o-disubstituted phosphinophenyl-methyl]ferrocene (Taniaphos), 1,1-bis(disubstituted-phosphotano)ferrocene (FerroTANE), 7,7'-bis(diphenylphosphino)-3,3',4,4'-tetrahydro-4,4'-dimethyl-8,8'-bi(2H-1,4-benzoxazin) (Solphos) and the like.

For production of an optically active amine compound, an optically active ligand is used as a "ligand" to be used for the "transition metal complex".

The "transition metal complex" to be used as a catalyst in [Method A-1] or [Method A-2] can be produced from a ligand and other complex to be a transition metal source by a known means (production of rhodium complex; Journal of the American Chemical Society (J. Am. Chem. Soc.), vol. 94, page 6429, 1972, Organic•Synthesis (Org. Synth.), vol. 67, page 33, 1989: production of ruthenium complex; Journal•of•Organic•Chemistry (J. Org. Chem.), vol. 57, page 4053, 1992, Tetrahedron Asymmetry (Tetrahedron Asym.), vol. 2, page 43, 1991, Journal•of•Organic•Chemistry (J. Org. Chem.), vol. 59, page 3064, 1994, Angewandte Chemie•Internaational Edition (Angew. Chem. Int. Ed.), vol. 37, page 1703, 1998: production of iridium complex; Journal•of•Organometallic Chemistry (J. Organomet. Chem.), vol. 428, page 213, 1992: production of palladium complex; Organometallics, vol. 12, page 4188, 1993, Journal of the American Chemical Society (J. Am. Chem. Soc.), vol. 121, page 5450, 1999: production of nickel complex; The Chemical Society of Japan ed. (Maruzen) "Jikken Kagaku Kouza, fifth edition" vol. 21, organic transition metal compound, supramolecular complex, pages 293-294 (2004): production of copper complex; The Chemical Society of Japan ed. (Maruzen) "Jikken Kagaku Kouza, fifth edition" vol. 21, organic transition metal compound, supramolecular complex, page 357 (2004), Journal of Organic Chemistry (J. Org. Chem.), vol. 63, page 6090, 1998), and isolated or purified by a known means (e.g., concentration, solvent extraction, fractionation, crystallization, recrystallization, chromatography).

The "transition metal complex" to be used as a catalyst in [Method A-1] and [Method A-2]can also be prepared by adding diphosphine shown by the aforementioned L and other complex to be a transition metal source to the reaction system.

Preferred as the "transition metal complex" to be used as a catalyst in [Method A-1] and [Method A-2] is a rhodium complex or iridium complex, particularly preferably a rhodium complex. Of these, [Rh(cod)(L)]OTf, [Rh(cod)(L)]BF$_4$, [Rh(cod)(L)]ClO$_4$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(L)(CH$_3$OH)$_2$]OTf, [Rh(L) (CH$_3$OH)$_2$]BF$_4$, [Rh(L)(CH$_3$OH)$_2$]ClO$_4$, [Rh(L)(CH$_3$OH)$_2$]PF$_6$ or [Rh (L)(CH$_3$OH)$_2$]BPh$_4$ is preferable.

While the amount of the "transition metal complex" to be used as a catalyst also varies depending on the reaction container, form of reaction and the like, it is, for example, about 0.1-about 0.00001 mol per 1 mol of a compound represented by the formula (2) or the formula (4) as a substrate.

The "transition metal complex" itself to be used as a catalyst may be added to a reaction container, or prepared by adding the aforementioned "transition metal" and "ligand" to a container. When a "transition metal complex" is prepared by adding "transition metal" and "ligand" to a container, the "ligand" is added at a 1- to 100-fold necessary composition ratio relative to the "transition metal". For example, when [Rh(cod)(L)]OTf is used as a catalyst, it is prepared by adding Rh(cod)$_2$OTf as a "transition metal" and L as a "ligand" to a container. In this case, 1-100 mol, preferably 1-5 mol, more preferably 1.01-1.2 mol, of L is generally used relative to Rh(cod)$_2$OTf.

In the reaction of [Method A-1] or [Method A-2], a base is generally used and, as the base to be used, an inorganic base or an organic base can be used.

Examples of the inorganic base include alkali metal hydroxide such as lithium hydroxide, potassium hydroxide, sodium hydroxide, cesium hydroxide and the like; alkali metal alkoxide having 1 to 6 carbon atoms such as lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and the like; alkali metal thioalkoxide having 1 to 6 carbon atoms such as sodium thiomethoxide and the like; carbonate such as sodium carbonate, potassium carbonate, cesium carbonate and the like; hydrogen carbonate such as sodium hydrogen carbonate, potassium hydrogen carbonate and the like; acetate such as sodium acetate, potassium acetate and the like; phosphate such as tripotassium phosphate, sodium phosphate and the like; monohydrogen phosphate such as potassium monohydrogen phosphate, sodium monohydrogen phosphate and the like.

Examples of the organic base include aliphatic amines such as trimethylamine, triethylamine, N-methylmorpholine, N,N-diisopropylethylamine, diethylamine, diisopropylamine, cyclohexylamine, ethylenediamine and the like; aromatic amines such as pyridine, picoline, N,N-dimethylaniline and the like.

As the inorganic base, specifically, lithium hydroxide, potassium hydroxide, sodium hydroxide, potassium tert-butoxide, sodium methoxide, sodium carbonate, potassium carbonate, cesium carbonate, sodium monohydrogen phosphate and tripotassium phosphate are preferable. As the organic base, aliphatic amine is more preferable.

The amount of the base to be used is about 0.01-about 100 mol, preferably about 0.1-about 10 mol, per 1 mol of a compound represented by the formula (2) or the formula (4), which is the substrate.

The reaction of [Method A-1] or [Method A-2] is generally performed in a solvent. Such solvent is not particularly limited as long as it is inert to the reaction and solubilizes the starting compound and catalyst. For example, aromatic hydrocarbons such as toluene, xylene and the like; aliphatic hydrocarbons such as heptane, hexane and the like; halogenated hydrocarbons such as methylene chloride and the like; ethers such as diethyl ether, tetrahydrofuran and the like; alcohols such as methanol, ethanol, 2-propanol, butanol, benzyl alcohol and the like; nitriles such as acetonitrile and the like; amides such as N,N-dimethylformamide and the like; sulfoxides such as dimethyl sulfoxide and the like are used. These solvents can be mixed and used at an appropriate ratio.

The amount of the solvent to be used is appropriately determined according to the solubility of a compound represented by the formula (2) or the formula (4), which is the substrate and the like. For example, when alcohol (preferably methanol) is used as a solvent, the reaction can be performed in a state closer to no solvent or in a not less than 100-fold weight of a solvent relative to a compound represented by the formula (2) or the formula (4). Generally, about 2- to about 50-fold weight of a solvent is preferably used relative to a compound represented by the formula (2) or the formula (4).

Hydrogenation can be performed by any of batch type and continuous type reactions. Hydrogenation is performed in the presence of hydrogen, and the hydrogen pressure is, for example, 0.01-200 atm, preferably 1-15 atm.

The reaction temperature is generally −30° C.-100° C., preferably 0-80° C., more preferably 10-50° C. The reaction time is generally 0.1-72 hr, preferably 1-48 hr.

A compound represented by the formula (3) or the formula (5), which is obtained by a hydrogenation reaction, may be purified by a known means (e.g., fractional recrystallization, chiral column method, diastereomeric salt formation method). When an optically active amine is to be produced, purification by crystallization according to a diastereomeric salt formation method is preferable to obtain a salt of a compound represented by the formula (3) or the formula (5) having a high optical purity.

(Production Method of Optically Active Hexahydropyrroloquinolines)

By performing the reaction of [Method A-1] or [Method A-2] simultaneously with other reaction in combination, a more complicated compound can be produced. For example, a reaction example for obtaining a compound represented by the formula (8) from a compound represented by the following formula (7) can be mentioned.

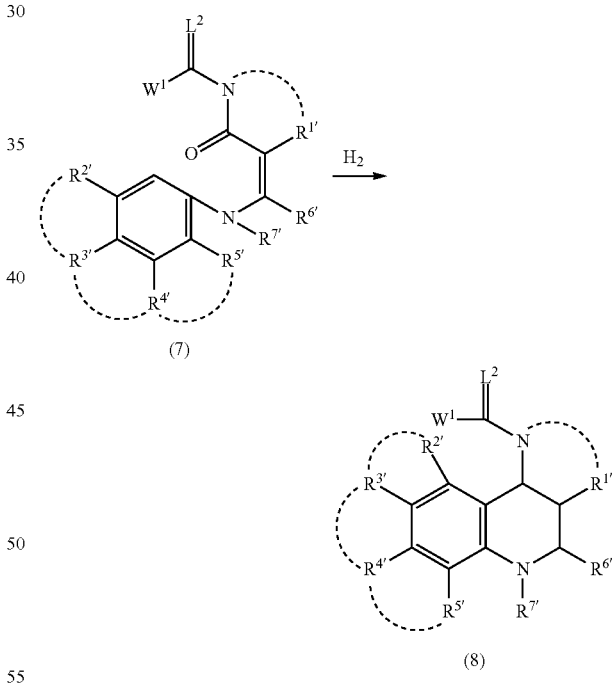

wherein $R^{1'}$ is a hydrogen atom or an alkyl group optionally having substituent(s), or $R^{1'}$ and the nitrogen atom of the formula $W^1$—C(=$L^2$)-N— group are joined to form, together with the adjacent atom, a 4- to 9-membered nitrogen-containing heterocycle optionally having substituent(s), $L^2$ is an oxygen atom, a sulfur atom or an imino group optionally having substituent(s), $W^1$ is an amino group optionally having substituent(s) or a hydroxy group optionally having substituent(s), $R^{2'}$, $R^{3'}$, $R^{4'}$ and $R^{5'}$ are the same or different and each is a hydrogen atom, a halogen atom, a nitro group, a cyano group, a hydrocarbon group optionally having substituent(s), a heterocyclic group optionally having substituent(s), an amino group optionally having substituent(s), a hydroxy group optionally having substituent(s), an alkylcarbonyl group optionally having substituent(s), an alkoxycarbonyl group optionally having substituent(s), a carboxyl group, a carbamoyl group optionally having substituent(s), or $R^{2'}$ and $R^{3'}$, $R^{3'}$ and $R^{4'}$ and $R^{4'}$ and $R^{5'}$ are each joined to form, together with the adjacent atom, a 4- to 8-membered ring optionally having substituent(s), $R^{6'}$ is a hydrogen atom, a halogen atom, a hydrocarbon group optionally having substituent(s), a heterocyclic group optionally having substituent(s), a hydroxy group optionally having substituent(s), an alkylcarbonyl group optionally having substituent(s), an alkoxycarbonyl group optionally having substituent(s), a carboxyl group or a carbamoyl group optionally having substituent(s), $R^{7'}$ is a hydrogen atom, a hydrocarbon group optionally having substituent(s), a heterocyclic group optionally having substituent(s), an acyl group, a sulfonyl group optionally having substituent(s) or a silyl group optionally having substituent(s).

Examples of the "alkyl group optionally having substituent(s)" for $R^{1'}$ include those similar to the "$C_{1-6}$ alkyl group optionally having substituent(s)" for $R^5$, $R^6$ or $R^7$.

Examples of the substituent in the "imino group optionally having substituent(s)" for $L^2$ include those similar to the substituents of the "hydroxy group optionally having substituent(s)" for $R^5$, $R^6$ or $R^7$.

Examples of the substituent in the "amino group optionally having substituent(s)" for $W^1$ include those similar to the substituents of the "hydroxy group optionally having substituent(s)" for $R^5$, $R^6$ or $R^7$.

Examples of the substituent in the "hydroxy group optionally having substituent(s)" for $W^1$ include those similar to the substituents of the "hydroxy group optionally having substituent(s)" for $R^5$, $R^6$ or $R^7$.

Examples of the "hydrocarbon group optionally having substituent (s)" for $R^{2'}$, $R^{3'}$, $R^{4'}$ or $R^{5'}$ include those similar to the "hydrocarbon group optionally having substituent(s)" for $R^5$, $R^6$ or $R^7$.

Examples of the "heterocyclic group optionally having substituent(s)" for $R^{2'}$, $R^{3'}$, $R^{4'}$ or $R^{5'}$ include those similar to the "heterocyclic group optionally having substituent(s)" for $R^5$, $R^6$ or R.

Examples of the substituent of the "amino group optionally having substituent(s)" for $R^{2'}$, $R^{3'}$, $R^{4'}$ or $R^{5'}$ include those similar to the substituents of the "hydroxy group optionally having substituent(s)" for $R^5$, $R^6$ or $R^7$.

Examples of the substituents of the "hydroxy group optionally having substituent(s)" for $R^{2'}$, $R^{3'}$, $R^{4'}$ or $R^{5'}$ include those similar to the substituents of the "hydroxy group optionally having substituent(s)" for $R^5$, $R^6$ or $R^7$.

Examples of the alkylcarbonyl group of the "alkylcarbonyl group optionally having substituent(s)" for $R^{2'}$, $R^{3'}$, $R^{4'}$ or $R^{5'}$ include $C_{1-6}$ alkylcarbonyl groups (e.g., acetyl, propionyl, butyryl, isobutyryl, valeryl, isovaleryl, pivaloyl). Examples of the substituent of the "alkylcarbonyl group optionally having substituent(s)" include those similar to the substituents of the "hydroxy group optionally having substituent(s)" for $R^5$, $R^6$ or $R^7$.

Examples of the alkoxycarbonyl group of the "alkoxycarbonyl group optionally having substituent(s)" for $R^{2'}$, $R^{3'}$, $R^{4'}$ or $R^{5'}$ include $C_{1-6}$ alkoxycarbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl). Examples of the substituent of the "alkoxycarbonyl group optionally having substituent(s)" include those similar to the substituents of the "hydroxy group optionally having substituent(s)" for $R^5$, $R^6$ or $R^7$.

Examples of the "carbamoyl group optionally having substituent(s)" for $R^{2'}$, $R^{3'}$, $R^{4'}$ or $R^{5'}$ include N-mono-$C_{1-6}$ alkylcarbamoyl groups (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), and N,N-di-$C_{1-6}$ alkylcarbamoyl groups (e.g., N,N-dimethylcarbamoyl, N,N-diethylcarbamoyl, N,N-dipropylcarbamoyl, N,N-diisopropylcarbamoyl, N-ethyl-N-methylcarbamoyl).

Examples of the "hydrocarbon group optionally having substituent(s)" for $R^{6'}$ include those similar to the "hydrocarbon group optionally having substituent(s)" for $R^5$, $R^6$ or $R^7$.

Examples of the "heterocyclic group optionally having substituent(s)" for $R^{6'}$ include those similar to the "heterocyclic group optionally having substituent(s)" for $R^5$, $R^6$ or $R^7$.

Examples of the "substituent" of the "hydroxy group optionally having substituent(s)" for $R^{6'}$ include those similar to the "substituents" of the "hydroxy group optionally having substituent(s)" for $R^5$, $R^6$ or $R^7$.

Examples of the "alkylcarbonyl group optionally having substituent(s)" for $R^{6'}$ include those similar to the "alkylcarbonyl group optionally having substituent(s)" for $R^{2'}$, $R^{3'}$, $R^{4'}$ or $R^{5'}$.

Examples of the "alkoxycarbonyl group optionally having substituent(s)" for $R^{6'}$ include those similar to the "alkoxycarbonyl group optionally having substituent(s)" for $R^{2'}$, $R^{3'}$, $R^{4'}$ or $R^{5'}$.

Examples of the "carbamoyl group optionally having substituent(s)" for $R^{6'}$ include those similar to the "carbamoyl group optionally having substituent(s)" for $R^{2'}$, $R^{3'}$, $R^{4'}$ or $R^{5'}$.

Examples of the "hydrocarbon group optionally having substituent(s)" for $R^{7'}$ include those similar to the "hydrocarbon group optionally having substituent(s)" for $R^5$, $R^6$ or $R^7$.

Examples of the "heterocyclic group optionally having substituent(s)" for $R^{7'}$ include those similar to the "heterocyclic group optionally having substituent(s)" for $R^5$, $R^6$ or $R^7$.

Examples of the "acyl group" for $R^{7'}$ include those similar to the "acyl group" for $R^5$, $R^6$ or $R^7$.

Examples of the "sulfonyl group optionally having substituent(s)" for $R^{7'}$ include those similar to the "sulfonyl group optionally having substituent(s)" for $R^5$, $R^6$ or $R^7$.

Examples of the "silyl group optionally having substituent(s)" for $R^{7'}$ include those similar to the "silyl group optionally having substituent(s)" for $R^8$ or $R^9$.

$R^{1'}$ and nitrogen atom of $W^1$—C(=$L^2$)-N— group are joined to form, together with the adjacent atom, a 4- to 9-membered nitrogen-containing heterocycle optionally having substituent(s), which is, for example, a ring structure of the following formula.

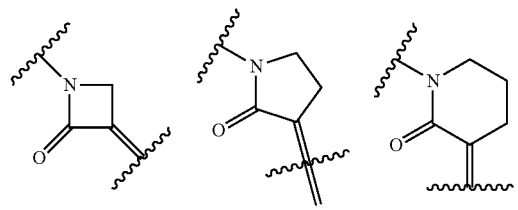

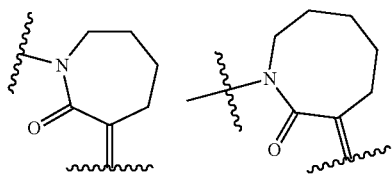

In the above-mentioned formulas, as the substituent that the ring optionally has, the groups recited as the substituent of "$C_{6-14}$ aryl group" can be mentioned, which optionally have 1 to 3 substituents at substitutable position(s).

$R^{2'}$ and $R^{3'}$ are joined to form, together with the adjacent atom, a 4- to 8-membered ring optionally having substituent(s), which is, for example, a ring structure of the following formula.

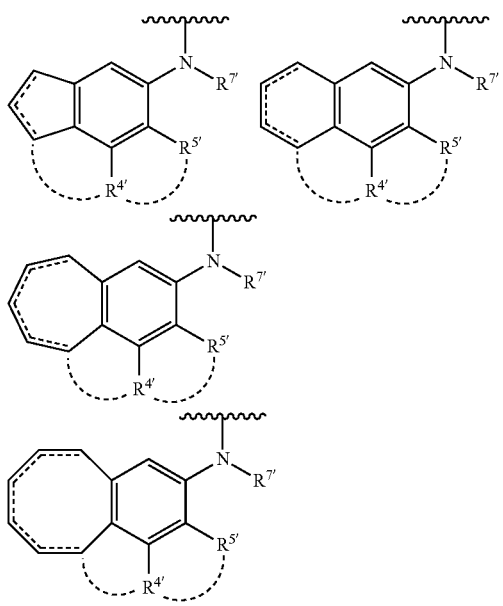

wherein the broken line part may be a double bond (may be fused with a benzene ring via a double bond in the broken line part), and $R^{4'}$, $R^{5'}$, and $R^{7'}$ are as defined above. In the above-mentioned formulas, as the substituent that the ring optionally has, the groups recited as the substituent of "$C_{6-14}$ aryl group" can be mentioned, which optionally have 1 to 3 substituents at substitutable position(s).

$R^{3'}$ and $R^{4'}$ are joined to form, together with the adjacent atom, a 4- to 8-membered ring optionally having substituent(s), which is, for example, a ring structure of the following formula.

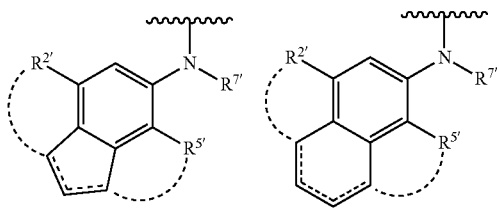

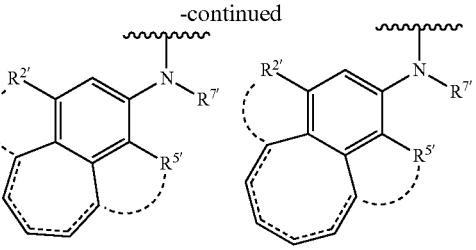

wherein the broken line part may be a double bond (may be fused with a benzene ring via a double bond in the broken line part), and $R^{2'}$, $R^{5'}$, and $R^{7'}$ are as defined above. In the above-mentioned formulas, as the substituent that the ring optionally has, the groups recited as the substituent of "$C_{6-14}$ aryl group" can be mentioned, which optionally have 1 to 3 substituents at substitutable position(s).

$R^{4'}$ and $R^{5'}$ are joined to form, together with the adjacent atom, a 4- to 8-membered ring optionally having substituent(s), which is, for example, a ring structure of the following formula.

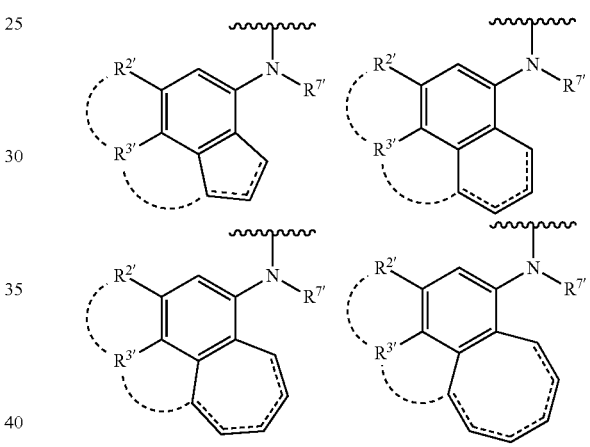

wherein the broken line part may be a double bond (may be fused with a benzene ring via a double bond in the broken line part), and $R^{2'}$, $R^{3'}$, and $R^{7'}$ are as defined above. In the above-mentioned formulas, as the substituent that the ring optionally has, the groups recited as the substituent of "$C_{6-14}$ aryl group" can be mentioned, which optionally have 1 to 3 substituents at substitutable position(s).

Now, Production Example of optically active hexahydropyrroloquinolines is shown.

Compound (8) recited as a Production Example of optically active hexahydropyrroloquinolines can be produced by reacting a compound represented by the formula (7) with hydrogen. As a catalyst to be used for this reaction, a "transition metal complex" is preferable, and the "transition metal complex" is exemplified by those similar to the "transition metal complex" used as a catalyst in [Method A-1] or [Method A-2].

Particularly in such production, a "transition metal complex" having a diphosphine ligand obtained in the present invention (hereinafter to be referred to as "the transition metal complex of the present application") is preferably used.

Particularly, a "transition metal complex of the present application" wherein the transition metal is rhodium (hereinafter to be referred to as "the rhodium complex of the present application") is preferable.

The rhodium complex of the present application or a salt thereof (hereinafter the "rhodium complex of the present application" also includes a salt thereof) can be produced according to a known method.

When the rhodium complex of diphosphine ligand of the present application is to be produced, it can be produced by reacting a diphosphine ligand and di-μ-chloro-bis[(cycloocta-1,5-diene)rhodium (I)] in a solvent according to the method described in Journal of the American Chemical Society (J. Am. Chem. Soc.), vol. 94, page 6429, 1972. It can also be produced by reacting a diphosphine ligand with di-p-chloro-bis[(cycloocta-1,5-diene)rhodium (I)] and silver perchlorate according to the method described in Organic Synthesis (Org. Synth.), vol. 67, page 33, 1989.

Among the rhodium complex of the present application, [Rh(cod)(L)]OTf, [Rh(cod)(L)]BF$_4$, [Rh(cod)(L)]ClO$_4$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(L)(CH$_3$OH)$_2$]OTf, [Rh(L)(CH$_3$OH)$_2$]BF$_4$, [Rh(L)(CH$_3$OH)$_2$]ClO$_4$, [Rh(L)(CH$_3$OH)$_2$]PF$_6$, and [Rh(L)(CH$_3$OH)$_2$]BPh$_4$ are preferable.

A diphosphine ligand (L) to be used for the rhodium complex of the present application is a compound represented by the formula (9).

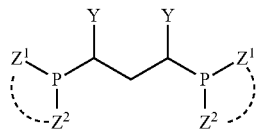

wherein each symbol is as defined above.

The production method of the compound represented by the formula (9) is shown below.

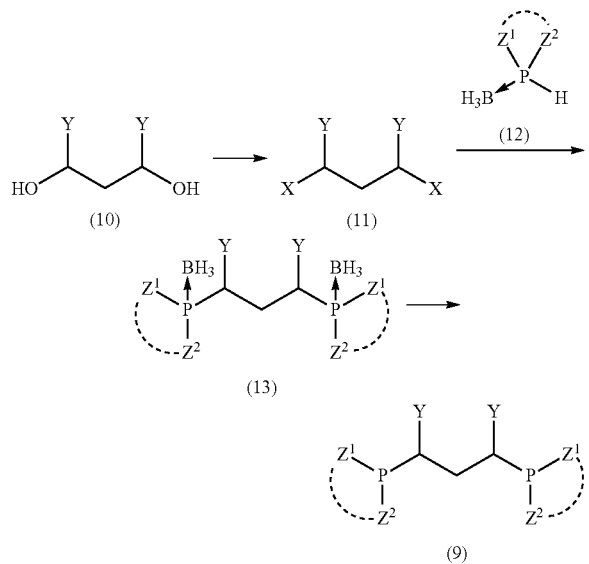

wherein each symbol is as defined above.

The method of obtaining compound (11) from compound (10) is a method for introducing a leaving group X, for which a method known per se can be selected. For example, the method described in Journal of Organometallic Chemistry, 279 (1985) 23-29 can be mentioned.

Compound (12) or a salt thereof and compound (11) are reacted in a solvent in the presence of potassium tert-butoxide or sodium tert-butoxide to give compound (13) or a salt thereof, which is reacted in the presence of a base to give compound (9) or a salt thereof.

Specific examples of compound (12) include diphenylphosphine-borane complex, bis(4-methylphenyl)phosphine-borane complex, bis(4-methoxyphenyl)phosphine-borane complex, bis(4-tert-butylphenyl)phosphine-borane complex, bis(3,5-di-methylphenyl)phosphine-borane complex and the like.

Examples of the "base" to be used for obtaining compound (9) from compound (13) include amines such as 1,4-diazabicyclo[2.2.2]octane (abbreviation: DABCO), triethylamine, diisopropylethylamine, tri(n-propyl)amine, tri(n-butyl)amine, 1,8-diazabicyclo[5.4.0]-7-undecene (abbreviation: DBU), tetramethylethylenediamine, dimethylaniline, 1,4-dimethylpiperazine, 1-methylpiperidine, 1-methylpyrrolidine, 4-dimethylaminopyridine, pyridine, diethylamine and the like. Of these, preferred is DABCO, DBU or diethylamine. Particularly preferred is diethylamine.

Of compound (9), a compound represented by the formula (14) is preferable.

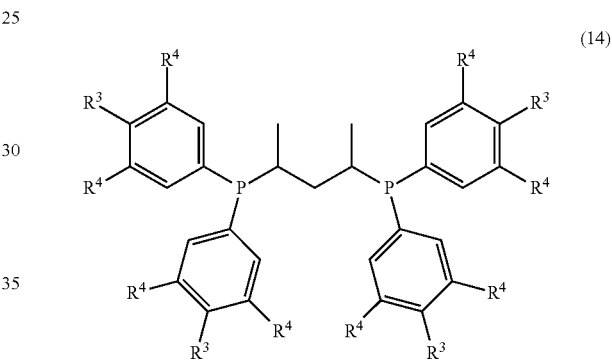

wherein each symbol is as defined above.

More preferable ligand includes 2,4-bis(diphenylphosphino)pentane (SKEWPHOS), and a SKEWPHOS derivative wherein one benzene ring on phosphorus atom of SKEWPHOS has 1 to 5 substituents such as a $C_{1-6}$ alkyl group and the like.

Specific examples of compound (14) include 2,4-bis(diphenylphosphino)pentane (abbreviation: skewphos), 2,4-bis(4-methylphenylphosphino)pentane (abbreviation: tol-skewphos), 2,4-bis(4-methoxyphenylphosphino)pentane (abbreviation: pm-skewphos), 2,4-bis(4-tert-butylphenylphosphino)pentane (abbreviation: ptbp-skewphos) and 2,4-bis(3,5-di-methylphenylphosphino)pentane (abbreviation: xylyl-skewphos) and the like. Of these, 2,4-bis(4-tert-butylphenylphosphino)pentane (abbreviation: ptbp-skewphos) is preferable. The above-mentioned compound contains (R) form, (S) form, and a mixture of (R) form and (S) form (ratio of the both is not limited).

The amount of compound (12) to be used is about 2 to 5 mol, preferably about 2 to 3 mol, per 1 mol of compound (11).

The amount of potassium tert-butoxide or sodium tert-butoxide to be used is about 2 to 5 mol, preferably about 2 to 3 mol, per 1 mol of compound (11).

The amount of the base to be used for obtaining compound (9) from compound (13) is about 10 to 100 mol, preferably about 20 to 30 mol, per 1 mol of compound (13). The reaction for obtaining compound (13) can be performed in an inert organic solvent.

Examples of the organic solvent for obtaining compound (13) from compound (11) include hydrocarbons (hexane, pentane, cyclohexane etc.), amides (N,N-dimethylformamide (DMF), N,N-dimethylacetamide, N-methylpyrrolidone, 1,3-dimethyl-2-imidazolidinone etc.), aromatic hydrocarbons (toluene, benzene, chlorobenzene etc.), ethers (diisopropyl ether, diethyl ether, tetrahydrofuran (THF), 1,4-dioxane, 1,2-dimethoxyethane etc.), halogenated hydrocarbons (chloroform, dichloromethane, 1,2-dichloroethane, carbon tetrachlorides etc.), alcohols (methanol, ethanol, isopropanol, tert-butanol etc.), ketones (acetone, ethylmethylketone etc.), sulfoxides (dimethyl sulfoxide etc.), nitriles (acetonitrile, propionitrile etc.), phosphoric acid amides (hexamethylphosphoric acid amide etc.) and the like. These solvents may be used alone or as a mixed solvent. Preferable solvents are halogenated hydrocarbons, ethers, aromatic hydrocarbons and the like. More preferred are ethers (diethyl ether, tetrahydrofuran etc.).

The reaction for obtaining compound (9) from compound (13) can be performed in an inert organic solvent. Examples of the organic solvent include hydrocarbons (hexane, pentane, cyclohexane etc.), amides (N,N-dimethylformamide (DMF), N,N-dimethylacetamide, N-methylpyrrolidone, 1,3-dimethyl-2-imidazolidinone etc.), aromatic hydrocarbons (toluene, benzene, chlorobenzene etc.), ethers (diisopropyl ether, diethyl ether, tetrahydrofuran (THF), 1,4-dioxane, 1,2-dimethoxyethane etc.), halogenated hydrocarbons (chloroform, dichloromethane, 1,2-dichloroethane, carbon tetrachlorides etc.), alcohols (methanol, ethanol, isopropanol, tert-butanol etc.), ketones (acetone, ethylmethylketone etc.), sulfoxides (dimethyl sulfoxide etc.), nitriles (acetonitrile, propionitrile etc.), phosphoric acid amides (hexamethylphosphoric acid amide etc.) and the like. These solvents may be used alone or as a mixed solvent. Preferred solvents are halogenated hydrocarbons, ethers, aromatic hydrocarbons and the like. More preferred are aromatic hydrocarbons (toluene, benzene etc.).

The reaction temperature of the reaction for obtaining compound (13) from compound (11) is about 0 to 100° C., preferably about 20 to 30° C. The reaction time of the reaction is about 1 to 120 hr, preferably about 24 to 36 hr.

The reaction temperature of the reaction for obtaining compound (9) from compound (13) is about 30 to 200° C., preferably about 50 to 100° C. The reaction time of the reaction is about 1 to 240 hr, preferably about 24 to 72 hr.

According to the aforementioned production method, compound (9) can be produced without isomerization of the structure of compound (10). That is, when any of the optical isomers of (2R,4R) form and (2S,4S) form of an optically active compound (10) is appropriately selected in the present invention, an optical isomer of the object compound (9) can be selectively obtained. For example, when a (2R,4R) form of compound (10) is used, a (2S,4S) form of compound (9) can be efficiently produced, and when a (2S,4S) form of compound (10) is used, a (2R,4R) form of compound (9) can be efficiently produced.

In the reaction from a compound represented by the formula (7) to a compound represented by the formula (8), addition of an "aromatic compound having a hydroxyl group" and/or a compound represented by the aforementioned formula (6) is preferable. As a method of addition, it may be added in advance before starting the reaction, or during the reaction.

The amount of the "aromatic compound having a hydroxyl group" to be added is preferably 0.01-100 equivalents, more preferably 0.1-10 equivalents.

The amount of a compound represented by the formula (6) to be added is preferably 0.01-100 equivalents, more preferably 0.1-10 equivalents.

Preferable scopes of the "aromatic compound having a hydroxyl group" and the compound represented by the formula (6) are as mentioned above.

A most preferable production example of the compound represented by the optically active hexahydropyrroloquinoline compound (8) is as follows.

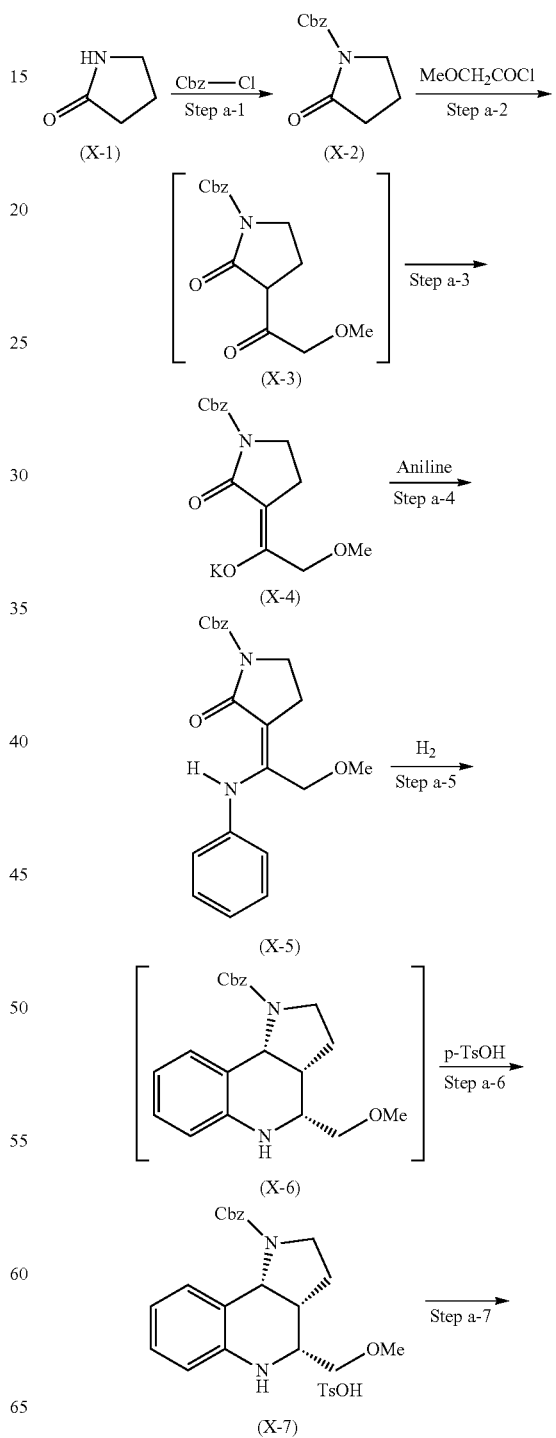

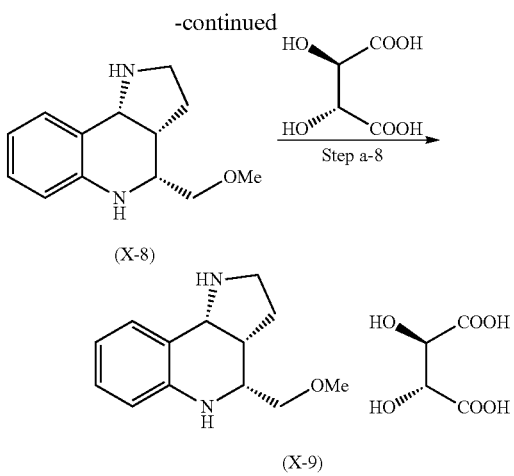

<Step a-1>

Compound (X-1) can be converted to compound (X-2) by protecting a nitrogen atom of compound (X-1). When a benzyloxycarbonyl group is used as a protecting group, a reaction with benzyl chloroformate can achieve the protection.

This reaction is desirably performed after reacting compound (X-1) with a base in advance.

Examples of the base to be used for this reaction include alkali metal hydroxide such as lithium hydroxide, sodium hydroxide, potassium hydroxide and the like; alkaline earth metal hydroxide such as barium hydroxide and the like; alkali metal carbonate such as sodium carbonate, potassium carbonate, cesium carbonate and the like; alkali metal hydrogen carbonate such as sodium hydrogen carbonate and the like; alkali metal phosphate such as tripotassium phosphate and the like; acetate such as sodium acetate, ammonium acetate and the like; aromatic amines such as pyridine, lutidine and the like; tertiary amines such as triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine, N-methylmorpholine and the like; alkali metal hydride such as sodium hydride, potassium hydride and the like; metal amides such as sodium amide, lithium diisopropylamide, lithium hexamethyldisilazide and the like; alkali metal alkoxide having 1 to 6 carbon atoms such as sodium methoxide, sodium ethoxide, sodium tert-butoxide, potassium tert-butoxide and the like; organic lithiums such as methyllithium, n-butyllithium, sec-butyllithium, tert-butyllithium and the like. Most preferable base is sodium hydroxide.

The amount of benzyl chloroformate to be used is generally about 0.2-about 10 mol, preferably about 0.5-about 3 mol, more preferably about 0.9-about 2 mol, relative to compound (X-1).

The amount of the base to be used is generally about 0.2-about 10 mol, preferably about 0.5-about 3 mol, more preferably about 1-about 2 mol, per 1 mol of compound (X-1).

The reaction is advantageously performed in a solvent inert to the reaction. While such solvent is not particularly limited as long as the reaction proceeds, for example, ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; ketones such as acetone, ethylmethylketone and the like; sulfoxides such as dimethyl sulfoxide and the like can be mentioned. Among these, the above-mentioned ethers, aromatic hydrocarbons, saturated hydrocarbons, amides and nitriles are preferable. One or more kinds of these may be mixed and used at a convenient ratio. Preferred are tetrahydrofuran, diethyl ether and toluene, and the most preferred solvent is toluene.

The amount of the solvent to be used for this reaction is 1- to 100-fold weight, preferably 2- to 50-fold weight, relative to compound (X-1).

When compound (X-1) is reacted with a base in advance, the reaction temperature is generally −70-200° C., preferably −70-150° C. When reacted with benzyl chloroformate, the reaction temperature is generally −70-100° C., preferably 0-50° C. While the reaction time varies depending on the reagents and solvents to be used, it is generally 100 min-20 hr, preferably 6 hr-10 hr.

<Step a-2>

Compound (X-2) can be converted to compound (X-3) by reacting with methoxyacetyl chloride.

This reaction is desirably performed after reacting compound (X-2) with a base in advance.

Examples of the base to be used for this reaction include bases recited in the aforementioned step for obtaining compound (X-2). Preferred are sodium hydride, lithium hexamethyldisilazide and n-butyllithium, and more preferred is lithium hexamethyldisilazide.

The amount of methoxyacetyl chloride to be used is generally about 0.2-about 10 mol, preferably about 0.5-about 3 mol, more preferably about 0.9-about 2 mol, relative to compound (X-2).

The amount of the base to be used is generally about 0.2-about 10 mol, preferably about 0.5-about 3 mol, more preferably about 1-about 2 mol, per 1 mol of compound (X-2).

The reaction is advantageously performed in a solvent inert to the reaction. While such solvent is not particularly limited as long as the reaction proceeds, for example, the solvents recited in the aforementioned step for obtaining compound (X-2) can be mentioned. Among these, the above-mentioned ethers, amides, halogenated hydrocarbons and nitriles are preferable. One or more kinds of these may be mixed and used at a convenient ratio. Preferred are tetrahydrofuran, diethyl ether, dichloromethane and acetonitrile, and more preferred is tetrahydrofuran.

The amount of the solvent to be used for this reaction is 1- to 100-fold weight, preferably 2- to 50-fold weight, relative to compound (X-2).

The reaction temperature is generally −100-30° C., preferably −80-−40° C. While the reaction time varies depending on the reagents and solvents to be used, it is generally 10 min-20 hr, preferably 30 min-10 hr.

<Step a-3>

Compound (X-3) obtained in <step a-2> can be converted to potassium of X-4 by reacting with potassium carbonate.

The amount of potassium carbonate to be used is generally about 1-about 10 mol, preferably about 1-about 5 mol, more preferably about 1-about 3 mol, relative to compound (X-3).

The reaction is advantageously performed in a solvent inert to the reaction. Such solvent is not particularly limited as long as the reaction proceeds. Examples of the solvent include water; ethers such as diethyl ether, diisopropyl ether, diphenyl ether, tetrahydrofuran, 1,4-dioxane, 1,2-dimethoxyethane and the like; alcohols such as methanol, ethanol, isopropanol and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like.

Among these, the above-mentioned ethers, water, alcohols, amides and nitriles are preferable. Preferred are water, tetrahydrofuran, ethanol and acetonitrile, and more preferred are water and ethanol. One or more kinds of these may be mixed and used at a convenient ratio.

The reaction temperature is generally 0-100° C., preferably 10-50° C., more preferably, 20-30° C. While the reaction time varies depending on the reagents and solvents to be used, it is generally 30 min-20 hr, preferably 1 hr-10 hr.

<Step a-4>

Compound (X-4) can be converted to compound (X-5) by reacting with aniline.

This reaction is desirably performed after converting compound (X-4) to (X-3) by reacting with an acid in advance. Examples of the acid to be used for this reaction include inorganic acid (hydrochloric acid, hydrobromic acid, nitric acid, sulfuric acid, phosphoric acid, tetrafluoroboric acid etc.), and organic acid (formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, trifluoromethanesulfonic acid, 10-camphorsulfonic acid, sulfanilic acid etc.). A desirable acid is hydrochloric acid.

The converted (X-3) can be converted to compound (X-5) by reacting with aniline.

This reaction is desirably performed in the presence of a catalytic amount of an acid. Examples of the acid to be used for this reaction include inorganic acid (hydrochloric acid, hydrobromic acid, nitric acid, sulfuric acid, phosphoric acid, tetrafluoroboric acid etc.), and organic acid (formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, trifluoromethanesulfonic acid, 10-camphorsulfonic acid, sulfanilic acid etc.). A desirable acid is p-toluenesulfonic acid.

The amount of p-toluenesulfonic acid to be used is generally about 0.001-about 1 mol, preferably about 0.005-0.5 mol, more preferably about 0.01 to about 0.1 mol, relative to compound (X-4).

The amount of aniline to be used is generally about 0.2-about 10 mol, preferably about 0.5-about 3 mol, more preferably about 0.9-about 2 mol, relative to compound (X-4).

The reaction is advantageously performed in a solvent inert to the reaction. Such solvent is not particularly limited as long as the reaction proceeds. The reaction is advantageously performed in a solvent inert to the reaction. While such solvent is not particularly limited as long as the reaction proceeds, for example, ethers such as diethyl ether, diisopropyl ether, diphenyl ether, tetrahydrofuran and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like and the like can be mentioned. Among these, the above-mentioned ethers, aromatic hydrocarbons, saturated hydrocarbons, amides and nitriles are preferable. More preferred are tetrahydrofuran, toluene and cyclohexane.

The reaction temperature is generally 20-200° C., preferably 50-150° C., more preferably 70-100° C. While the reaction time varies depending on the reagents and solvents to be used, it is generally 30 min-20 hr, preferably 1 hr-3 hr. For example, the solvents mentioned in the aforementioned step for obtaining compound (X-2) can be mentioned. Among these, the above-mentioned ethers, amides and nitriles are preferable. One or more kinds of these may be mixed and used at a convenient ratio.

<Step a-5>

The amount of the "transition metal complex of the present application" to be used as a catalyst in the reaction of compound (X-5) is about 0.005 mol to about 1 mol, preferably about 0.01 mol to about 0.05 mol, per 1 mol of compound (X-5).

In the reaction of compound (X-5), hydrogen gas is used as a hydrogen source. The hydrogen pressure during the reaction is about 0.1 MPa to 10 MPa, preferably about 5 MPa to 10 MPa.

Compound (X-5) is reacted in a solvent. Examples of the solvent to be used include solvents selected from alcohol solvents (methanol, ethanol, n-propanol, isopropanol etc.), hydrocarbon solvents (hexane, benzene, toluene, xylene etc.), ether solvents (diethyl ether, diisopropyl ether, tert-butyl methyl ether, dioxane, tetrahydrofuran etc.), ester solvents (ethyl acetate, isopropyl acetate etc.), ketone solvents (acetone, methylethyl ketone etc.), nitrile solvents (acetonitrile, propionitrile etc.), sulfoxide solvents (dimethyl sulfoxide etc.) and amide solvents (N,N-dimethylformamide etc.) or mixed solvents of two or more kinds thereof. Of these, ketone solvents (acetone, methylethyl ketone etc.), particularly acetone, are preferable.

The reaction temperature of the reaction of compound (X-5) is preferably about 0° C. to about 180° C., particularly about 20° C. to about 100° C.

Examples of the "aromatic compound having a hydroxyl group" to be used as an additive in the reaction of compound (X-5) include aromatic compounds such as phenol, 4-bromophenol, 4-benzylphenol, 2-benzylphenol, 4-methoxyphenol, 3-methoxyphenol, 2-methoxyphenol, 4-ethyl-2-methoxyphenol, BINOL, para-hydroxybenzophenone, hydroquinone, benzhydrol, salicyl alcohol, phloroglucinol, catechol, resorcinol, cyanuric acid and the like. Of these, preferred are 4-bromophenol, 4-methoxyphenol, salicyl alcohol and cyanuric acid. Particularly preferred is cyanuric acid.

Examples of a compound represented by the formula (6)

(6)

wherein each symbol is as defined above, to be used as an additive and dehydrating agent in the reaction of compound (X-5) include acetals such as 2,2-dimethoxypropane and 2,2-diethoxypropane and the like. Of these, preferred is 2,2-dimethoxypropane.

<Step a-6>

Compound (X-6) can be obtained as a salt of para-toluenesulfonic acid.

The amount of para-toluenesulfonic acid to be used is generally about 0.2-about 10 mol, preferably about 0.5-about 3 mol, more preferably about 0.9-about 2 mol, relative to compound (X-4).

Compound (X-6) is converted to a salt in a solvent. Examples of the solvent to be used include solvents selected from alcohol solvents (methanol, ethanol, n-propanol, isopropanol etc.), hydrocarbon solvents (hexane, benzene, toluene, xylene etc.), ether solvents (diethyl ether, diisopropyl ether, tert-butyl methyl ether, dioxane, tetrahydrofuran etc.), ester solvents (ethyl acetate, isopropyl acetate etc.), ketone solvents (acetone, methylethyl ketone etc.), nitrile solvents (acetonitrile, propionitrile etc.), sulfoxide solvents (dimethyl sulfoxide etc.) and amide solvents (N,N-dimethylformamide etc.), and mixed solvents of two or more kinds thereof.

<Step a-7>

Compound (X-8) can be obtained by deprotecting compound (X-7).

Compound (X-7) can be deprotected in an aqueous hydrochloric acid solution.

<Step a-8>

Compound (X-8) can be obtained as a salt of tartaric acid. The amount of the tartaric acid to be used is generally about 0.2-about 10 mol, preferably about 0.5-about 3 mol, more preferably about 0.9-about 2 mol, relative to compound (X-8).

Compound (X-8) is converted to a salt in a solvent. Examples of the solvent to be used include solvents selected from those mentioned in the aforementioned step for obtaining compound (X-7) or mixed solvents of two or more kinds thereof.

A compound represented by the formula (1) contains (R) form, (S) form and a mixture of (R) form and (S) form (ratio of both is not limited), and an optically active form is preferable.

(Synthesis of Hexahydropyrroloquinoline Derivative)

Compound (X-8) or (X-9) produced by the aforementioned production method can be provided as, as shown in the following formula, a starting material for the production of a compound represented by the formula (16), which is useful as an NK2 receptor antagonist described in WO 2008-153027.

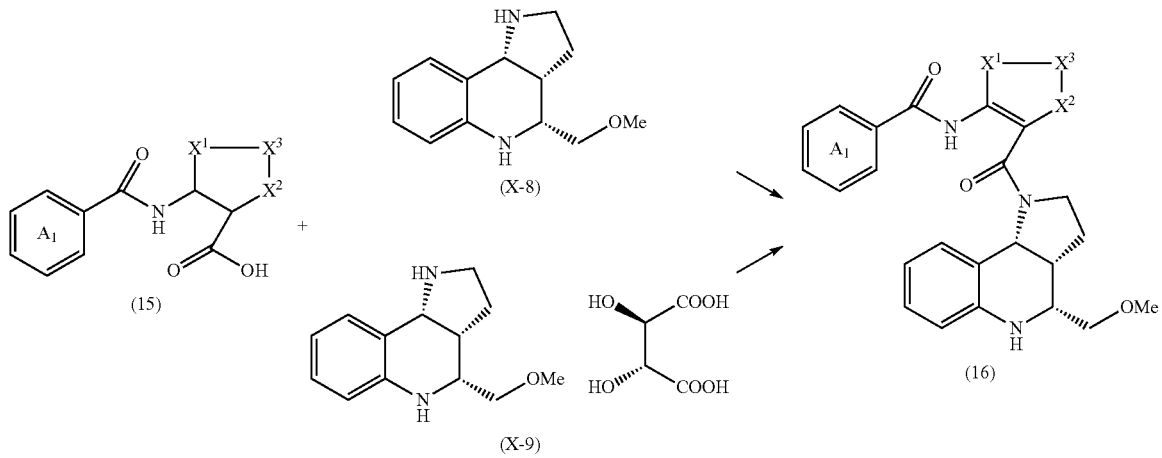

The amount of hydrochloric acid to be used is generally about 1-about 100 mol, preferably about 5-50 mol, more preferably about 10 to about 20 mol, relative to compound (X-7).

The reaction is advantageously performed in a solvent inert to the reaction. While such solvent is not particularly limited as long as the reaction proceeds, for example, water; ethers such as diethyl ether, diisopropyl ether, diphenyl ether, tetrahydrofuran and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like; halogenated hydrocarbons such as dichloromethane, chloroform, carbon tetrachloride, 1,2-dichloroethane and the like; nitriles such as acetonitrile, propionitrile and the like; sulfoxides such as dimethyl sulfoxide and the like, and the like can be mentioned. Among these, the above-mentioned water, ethers, amides and nitriles are preferable. One or more kinds of these may be mixed and used at a convenient ratio. Preferred is water.

The reaction temperature is generally 0-200° C., preferably, 50-150° C., more preferably, 60-100° C. While the reaction time varies depending on the reagents and solvents to be used, it is generally 1 hr-20 hr, preferably, 1 hr-5 hr.

wherein ring $A_1$ is a benzene ring optionally having substituent(s), and $X^1$, $X^2$ and $X^3$ are each a bond or a divalent $C_{1-5}$ chain hydrocarbon group optionally having substituent(s).

Examples of the substituent of the "benzene ring optionally having substituent(s) for ring $A_1$ include the groups recited as the substituent of the "$C_{6-14}$ aryl group", and the substituent may have 1 to 3 substituents at substitutable position(s). Examples of the "divalent $C_{1-5}$ chain hydrocarbon group" of the "divalent $C_{1-5}$ chain hydrocarbon group optionally having substituent(s)" for $X^1$, $X^2$ or $X^3$ include methylene (—$CH_2$—), ethylene (—$(CH_2)_2$—), propylene (—$(CH_2)_3$—), butylene (—$(CH_2)_4$—), a pentylene group (—$(CH_2)_5$—) and the like.

$X^1$ and $X^2$ are the same or different and each is preferably methylene (—$CH_2$—) or ethylene (—$(CH_2)_2$—). In a more preferable embodiment, one is methylene (—$CH_2$—) and the other is ethylene (—$(CH_2)_2$—). For $X^3$, methylene (—$CH_2$—) is preferable.

Examples of the substituent of the "divalent $C_{1-5}$ chain hydrocarbon group optionally having substituent(s)" for $X^1$, $X^2$ or $X^3$ include those similar to the substituents of the "$C_{1-10}$ alkyl group optionally having substituent(s)" for Y. It is preferably unsubstituted.

A known method can be used for the condensation reaction. For example, reference can be made to the aforementioned WO 2008153027.

A production method of a compound represented by the formula (15a) including a compound represented by the formula (15) is shown below.

A compound represented by the formula (15a) can be converted to a compound represented by the formula (15) by a method known per se, as mentioned below.

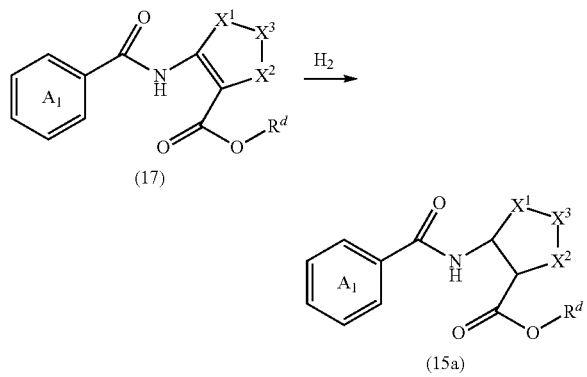

wherein $R^d$ is a hydrogen atom, a $C_{1-6}$ alkyl group optionally having substituent(s) or a $C_{7-14}$ aralkyl group optionally having substituent(s), and other symbols are as defined above.

Examples of the "$C_{1-6}$ alkyl group optionally having substituent(s)" for $R^d$ include those similar to the "$C_{1-6}$ alkyl group optionally having substituent(s)" for $R^5$, $R^6$ or $R^7$.

The "$C_{7-14}$ aralkyl group" of the "$C_{7-14}$ aralkyl group optionally having substituent(s)" for $R^d$ is an aralkyl group having 7 to 14 carbon atoms, and examples thereof include benzyl, phenethyl, naphthylmethyl, biphenylylmethyl and the like. Examples of the substituent of the "$C_{7-14}$ aralkyl group optionally having substituent(s)" include those similar to the substituents of the "$C_{1-6}$ alkyl group optionally having substituent(s)" for $R^5$, $R^6$ or $R^7$.

Compound (15a) can be produced by reacting a compound represented by the formula (17) with hydrogen. This reaction is generally performed in a solvent. Such solvent is not particularly limited as long as it is inert to the reaction and solubilizes a starting compound and a catalyst. For example, aromatic hydrocarbons such as toluene, xylene and the like; aliphatic hydrocarbons such as heptane, hexane and the like; halogenated hydrocarbons such as methylene chloride and the like; ethers such as diethyl ether, tetrahydrofuran and the like; alcohols such as methanol, ethanol, 2-propanol, butanol, benzyl alcohol and the like; nitriles such as acetonitrile and the like; amides such as N,N-dimethylformamide and the like; sulfoxides such as dimethyl sulfoxide and the like can be used. These solvents may be mixed at an appropriate ratio.

The amount of the solvent to be used is appropriately determined according to the solubility of a compound represented by the formula (17), which is a substrate, and the like. For example, when alcohol (preferably methanol) is used as a solvent, the reaction can be performed in a state closer to no solvent or in a not less than 100-fold weight of a solvent relative to a compound represented by (17). Generally, about 2- to about 50-fold weight of a solvent is preferably used relative to a compound represented by the formula (17).

Hydrogenation can be performed by any of batch type and continuous type reactions. Hydrogenation is performed in the presence of hydrogen, and the hydrogen pressure is, for example, 0.01-200 atm, preferably 1-15 atm.

The reaction temperature is generally −30° C.-100° C., preferably 0-80° C., more preferably 10-50° C. The reaction time is generally 0.1-72 hr, preferably 1-48 hr.

A compound represented by the formula (15a), which is obtained by the hydrogenation reaction, may be purified by a known means (e.g., fractional recrystallization, chiral column method, diastereomeric salt formation method).

When $R^d$ is a $C_{1-6}$ alkyl group optionally having substituent(s) or a $C_{7-14}$ aralkyl group optionally having substituent(s), it can be converted to a carboxylic acid represented by the formula (15) by subjecting to hydrolysis according to a method known per se.

When compound (15a) is obtained by reacting a compound represented by the formula (17) with hydrogen, a catalyst is preferably used. As the catalyst, the "transition metal complex" mentioned above as the catalyst in [Method A-1] or [Method A-2] is preferable.

In this production, among the "transition metal complex", a ruthenium complex wherein the transition metal is ruthenium (hereinafter to be referred to as "the ruthenium complex of the present application") is particularly preferable, which can be produced according to a known method described in relation to the aforementioned "transition metal complex".

When a compound represented by the formula (15a) including a compound represented by the formula (15) is produced by using the "ruthenium complex of the present application", an acid is preferably added as an additive. Examples of the acid to be added include inorganic acid (hydrochloric acid, hydrobromic acid, nitric acid, sulfuric acid, phosphoric acid, tetrafluoroboric acid etc.), and organic acid (formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, trifluoromethanesulfonic acid, 10-camphorsulfonic acid, sulfanilic acid etc.). Preferred inorganic acids are hydrochloric acid and tetrafluoroboric acid, and preferred organic acids are methanesulfonic acid, benzenesulfonic acid, p-toluenesulfonic acid, trifluoromethanesulfonic acid, 10-camphorsulfonic acid, sulfanilic acid and the like. Most preferred acid is tetrafluoroboric acid.

Among the "ruthenium complex of the present application", a compound represented by the formula (18) is preferable.

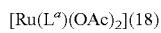

wherein $L^a$ is a diphosphine ligand, and Ac is acetyl.

Examples of the diphosphine ligand for $L^a$ include the ligands recited as diphosphine ligand in the aforementioned formula of the transition metal complex as the catalyst in [Method A-1] or [Method A-2]. These ligands contain an (R) form, (S) form and a mixture of (R) form and (S) form (ratio of the both is not limited). $L^a$ is preferably, a BINAP derivative wherein one benzene ring on phosphorus atom of BINAP, which is shown by the formula of the aforementioned transition metal complex as a catalyst in [Method A-1] or [Method A-2], has 1 to substituents such as a $C_{1-6}$ alkyl group and the like, or BINAP. Most preferred is 2,2'-bis[bis(3,5-di-tert-butyl-4-methoxyphenyl)phosphino]-1,1'-binaphthyl.

A compound represented by the formula (18) can be synthesized by a method known per se (J. Org. Chem., vol. 57, page 4053, 1992, or Inorg. Chem., vol. 27, page 566, 1988). More preferably, it can be produced by, as shown in the following, reacting a compound represented by the formula (19), which is synthesized by a method known per se (J. Chem. Soc., Perkin Trans. I, 1994, 2309), with alkali metal acetate.

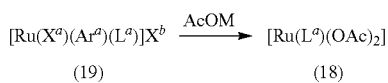

wherein $X^a$ is a halogen atom, $Ar^a$ is a benzene ring optionally having substituent(s), $X^b$ is a counter ion, M is alkali metal, and other symbols are as defined above.

Examples of the substituent of the "benzene ring optionally having substituent(s)" for Ar include the groups recited as the substituent of the "$C_{6-14}$ aryl group", and the substituent may have 1 to 3 substituents at substitutable position(s). Most preferred as Ar is p-cymene.

Examples of the counter ion for $X^b$ include $Cl^-$, $Br^-$, $I^-$, $OTf^-$, $ClO_4^-$, $PF_6^-$, $BF_4^-$ and $BPh_4^-$. Most preferred as $X^b$ is $Cl^-$. The alkali metal for M is lithium, sodium, potassium or the like. Most preferred as M is sodium. Most preferred as the halogen atom for $X^a$ is a chlorine atom. Preferable examples of the solvent to be used for synthesizing compound (18) from compound (19) include alcohols such as methanol, ethanol, 2-propanol, butanol, benzyl alcohol and the like. More preferred are methanol and ethanol, and most preferred is methanol. The amount of the solvent to be used is appropriately determined according to the solubility of a compound represented by the formula (19), which is a substrate, and the like. For example, when alcohol (preferably methanol) is used as a solvent, the reaction can be performed in a state closer to no solvent or in a not less than 100-fold weight of a solvent relative to a compound represented by (19). Generally, about 2- to about 50-fold weight of a solvent is preferably used relative to a compound represented by the formula (19).

The reaction temperature is generally −30° C.-100° C., preferably 0-80° C., more preferably 40-70° C. The reaction time is generally 0.1-72 hr, preferably 1-48 hr.

The amount of AcOM to be used is generally about 0.9-about 100 mol, preferably about 2-about 30 mol, relative to compound (19).

Compound (18) may be produced by reacting compound (19), synthesized by a method known per se, with AcOM, without isolating compound (19).

The obtained compound (18) may be purified by a known means (e.g., recrystallization method).

The transition metal complex of the present application is a useful catalyst capable of achieving even a ring closure synthesis reaction which could be complicated depending on the reaction substrate. Particularly, the rhodium complex of the present application can achieve even a ring closure synthesis reaction which could be complicated depending on the reaction substrate as mentioned above, and also achieves a selective reaction showing a high enantiomeric excess (ee %).

In addition, compound (9) preferable as a ligand of the rhodium complex of the present application, can be obtained by a production method capable of avoiding a complicated operation, since the object phosphorus compound (ligand) can be directly obtained from a reaction substrate (secondary phosphine-borane complex) under mild conditions while using tert-BuOK and tert-BuONa as a base to be used, rather than an extremely low temperature reaction using a base (butyllithium) conventionally used.

Furthermore, synthesis of $[Ru(L^a)(OAc)_2]$ from $RuCl_2(L)(dmf)_n$ (wherein each symbol is as defined above) is conventionally known. It was found that $[Ru(L^a)(OAc)_2]$ synthesized from $[Ru(X^a)(Ar^a)(L^a)]X^b$ according to the production method disclosed in the present application has high quality (high purity; when contaminated with complex assumed to be coordinated with dmf, inhibitory action is shown in the reaction using same as a catalyst) and shows high reactivity, as compared to one synthesized from $RuCl_2(L)(dmf)_n$.

EXAMPLES

The present invention is explained in more detail in the following by referring to Examples and Reference Examples, which are not to be construed as limitative. In the present specification, room temperature is 10° C. to 35° C. Each physical property in the Examples was measured using the following instruments.

$^1$H nuclear magnetic resonance spectrum ($^1$H-NMR): DPX500 (manufactured by Bruker), internal standard substance: tetramethylsilane $^{13}$C nuclear magnetic resonance spectrum ($^{13}$C-NMR): DPX500 (manufactured by Bruker), internal standard substance: $CDCl_3$, $CD_3OD$ $^{31}$P nuclear magnetic resonance spectrum ($^{31}$P-NMR): DPX500 (manufactured by Bruker), external standard substance: 85% $H_3PO_4$ aqueous solution mass spectrometry: JMS-700T (manufactured by JEOL Ltd.) elemental analysis: vario EL (manufactured by elementar) HPLC analysis: HITACHI L-7100 pump and L-7420 UV detector Example 1

Synthesis of (S,S)-PTBP-Skewphos-borane complex

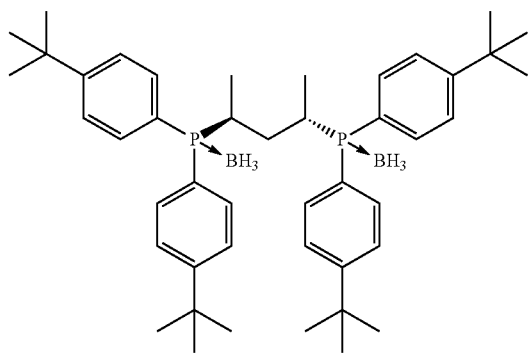

Under an argon atmosphere, into a 50 mL Schlenk flask were added di-p-tert-butylphenylphosphine-borane complex (1.64 g) [mw. 312.24, 5.25 mmol], (2R,4R)-pentanediol ditosylate (1.03 g) [mw. 412.52, 2.50 mmol], potassium tert-butoxide (0.65 g) [mw. 112.21, 5.79 mmol] and dehydrated tetrahydrofuran for organic synthesis (30 mL), and the mixture was stirred at room temperature for 68 hr. Insoluble matter was filtered off, and the filtrate was concentrated under reduced pressure. Methanol (20 mL) was added to allow for crystallization and the mixture was stirred for 1 hr at room temperature. After filtration under reduced pressure, the filtrate was washed with methanol, and dried in vacuo at 50° C. to give the object compound. White crystalline powder, 1.08 g, yield 62%, $^1$H-NMR (500 MHz, $CDCl_3$, TMS) δ 0.30-1.10 (br, 6H), 1.01 (dd, J=16.4 Hz, 6.9 Hz, 6H), 1.30 (d, J=4.7 Hz, 36H), 1.58-1.70 (m, 2H), 2.47-2.57 (m, 2H), 7.41-7.43 (m, 8H), 7.57-7.62 (m, 8H). $^{13}$C-NMR (125 MHz, $CDCl_3$, $CDCl_3$) δ13.52, 26.32-26.69 (m), 31.14, 34.90, 125.67-

125.81 (m), 131.19-134.07 (m), 154.43-154.59 (m). $^{31}$P-NMR (202 MHz, CDCl$_3$, H$_3$PO$_4$) δ 23.17 (brs).

Example 2

Synthesis of (S,S)-PTBP-Skewphos

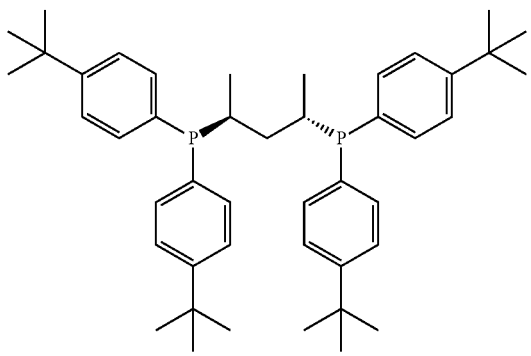 [SMILES: C[C@@H](C[C@H](C)P(c1ccc(C(C)(C)C)cc1)c1ccc(C(C)(C)C)cc1)P(c1ccc(C(C)(C)C)cc1)c1ccc(C(C)(C)C)cc1]

Under an argon atmosphere, into a 50 mL Schlenk flask were added (2S,4S)-PTBP-Skewphos-BH$_3$ (2.50 g) [mw. 692.59, 3.61 mmol], dehydrated toluene for organic synthesis (12.5 mL) and diethylamine (8 mL) [d=0.70, mw. 73.14, 76.56 mmol], and the mixture was stirred at 65° C. for 65 hr. After cooling, the mixture was concentrated under reduced pressure under an argon atmosphere, and the concentrate was purified by silica gel column. (silica gel amount: 25 g, eluent: toluene, Rf=0.95) The effective fraction was concentrated under reduced pressure, dehydrated methanol for organic synthesis (20 mL) was added, and the mixture was suspended by stirring for 1 hr. After filtration under reduced pressure, the crystals were washed with methanol, and dried in vacuo at 60° C. to give the object compound. White crystalline powder, 2.00 g, yield 83%, $^1$H-NMR (500 MHz, CDCl$_3$, TMS) δ 0.96 (dd, J=15.4 Hz, 6.6 Hz, 6H), 1.29 (d, J=9.1 Hz, 36H), 1.40-1.47 (m, 2H), 2.41-2.57 (m, 2H), 7.29-7.43 (m, 16H). $^{13}$C-NMR (125 MHz, CDCl$_3$, CDCl$_3$) δ15.70, 15.83, 27.60, 31.26, 31.28, 34.60, 34.61, 125.16, 125.22, 125.25, 125.31, 133.37, 133.41, 133.53, 133.57, 151.67, 151.71. $^{31}$P-NMR (202 MHz, CDCl$_3$, H$_3$PO$_4$) δ −3.91-(−3.74) (m).

Example 3

Synthesis of (S,S)-Tol-Skewphos-borane complex

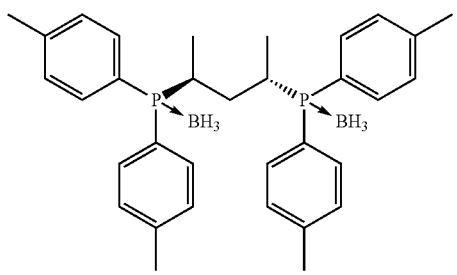

Under an argon atmosphere, into a 200 mL four-mouthed flask were added ditolylphenylphosphine-borane complex (7.12 g) [mw. 228.08, 31.22 mmol], (2R,4R)-pentanediol ditosylate (6.13 g) [mw. 412.52, 14.86 mmol], potassium tert-butoxide (3.84 g) [mw. 112.21, 34.22 mmol] and dehydrated tetrahydrofuran for organic synthesis (110 mL), and the mixture was stirred at room temperature for 24 hr. Insoluble matter was filtered off, and the filtrate was concentrated under reduced pressure and purified by silica gel column. (silica gel amount: 100 g, eluent: toluene) The effective fraction was concentrated under reduced pressure, dehydrated methanol for organic synthesis (80 mL) was added, and the mixture was suspended by stirring. After filtration under reduced pressure, the crystals were washed with methanol and dried in vacuo at 50° C. to give the object compound. White crystalline powder, 4.83 g, yield 62%, $^1$H-NMR (500 MHz, CDCl$_3$, TMS) δ 0.27-1.10 (br, 6H), 1.02 (dd, J=16.7 Hz, 6.9 Hz, 6H), 1.58 (m, 2H), 2.36 (s, 12H), 2.45-2.61 (m, 2H), 7.12-7.28 (m, 8H), 7.43-7.62 (m, 8H). $^{13}$C-NMR (125 MHz, CDCl$_3$, CDCl$_3$) δ13.12, 21.46, 25.70-26.54 (m), 31.31, 124.27, 124.70, 124.81, 125.31, 128.24, 129.05, 129.51, 129.58, 132.43, 132.50, 132.72, 132.80, 141.47. $^{31}$P-NMR (202 MHz, CDCl$_3$, H$_3$PO$_4$) δ 22.39-25.32 (brs).

Example 4

Synthesis of (S,S)-Tol-Skewphos

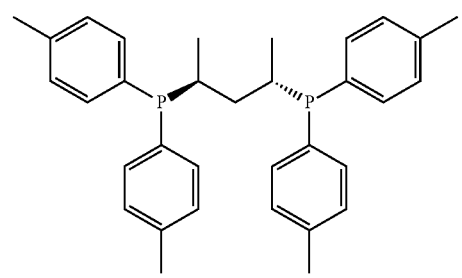

Under an argon atmosphere, into a 50 mL Schlenk flask were added (2S,4S)-Tol-Skewphos-BH$_3$ (4.76 g) [mw. 524.27, 9.08 mmol] and diethylamine (95 mL) [d=0.70, mw. 73.14, 909.21 mmol], and the mixture was stirred at 60° C. for 5 hr. After cooling, methanol (95 mL) was added, and the mixture was stirred at room temperature for 20 min. After concentration under reduced pressure, the concentrate was purified by silica gel column. (silica gel amount: 100 g, eluent:toluene/n-heptane=1/1) The effective fraction was concentrated under reduced pressure to give the object compound. Colorless oil, 4.07 g, yield 72%, $^1$H-NMR (500 MHz, CDCl$_3$, TMS) δ 0.97 (dd, J=15.4 Hz, 6.9 Hz, 6H), 1.30-1.41 (m, 2H), 2.40-2.52 (m, 2H), 7.00-7.10 (m, 8H), 7.25-7.40 (m, 8H). $^{13}$C-NMR (125 MHz, CDCl$_3$, CDCl$_3$) δ15.64, 15.78, 21.28, 27.0-28.0 (m), 36.0-37.0 (m), 129.11, 129.14, 133.50, 133.70, 133.94, 134.05, 138.51. $^{31}$P-NMR (202 MHz, CDCl$_3$, H$_3$PO$_4$) δ −2.71 (brs).

Example 5

Synthesis of (S,S)-Skewphos-borane complex

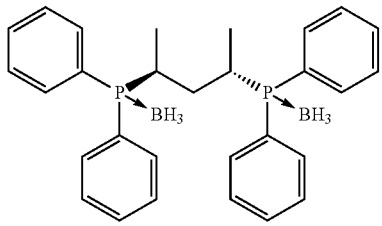

Under an argon atmosphere, into a 200 mL Schlenk flask were added diphenylphosphine-borane complex (5.00 g) [mw. 200.03, 25.0 mmol], (2R,4R)-pentanediol ditosylate (4.91 g) [mw. 412.52, 11.9 mmol], potassium tert-butoxide (3.07 g) [mw. 112.21, 27.4 mmol] and dehydrated tetrahydrofuran for organic synthesis (175 mL), and the mixture was stirred at room temperature for 28 hr. Insoluble matter was filtered off through silica gel, and the filtrate was concentrated under reduced pressure. Dehydrated methanol for organic synthesis (50 mL) was added, and the mixture was suspended by stirring in an ice bath for 1 hr. After filtration under reduced pressure, the crystals were washed with cold methanol, and dried in vacuo at 50° C. to give the object compound. White crystalline powder, 2.76 g, yield 50%, $^1$H-NMR (500 MHz, CDCl$_3$, TMS) δ 0.27-1.25 (br, 6H), 1.05 (dd, J=16.4 Hz, 6.9 Hz, 6H), 1.49-1.69 (m, 2H), 2.55-2.65 (m, 2H), 7.32-7.52 (m, 12H), 7.55-7.86 (m, 8H). $^{13}$C-NMR (125 MHz, CDCl$_3$, CDCl$_3$) δ13.06, 25.79-26.17 (m), 31.26, 128.73, 128.78, 131.24, 132.49, 132.73, 132.80. $^{31}$P-NMR (202 MHz, CDCl$_3$, H$_3$PO$_4$) δ 25.63-25.85 (brs).

Example 6

Synthesis of (S,S)-Skewphos

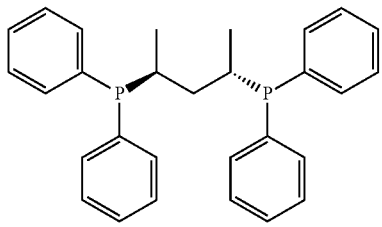 [SMILES: C[C@@H](C[C@H](C)P(c1ccccc1)c1ccccc1)P(c1ccccc1)c1ccccc1]

Under an argon atmosphere, into a 50 mL Schlenk flask were added (2S,4S)-Skewphos-BH$_3$ (1.00 g) [mw. 468.17, 2.14 mmol] and diethylamine (23 mL) [d=0.70, mw. 73.14, 220.1 mmol], and the mixture was stirred at 60° C. for 5 hr. After cooling in an ice bath, methanol (23 mL) was added, and the mixture was stirred in an ice bath for 20 min. The mixture was concentrated under reduced pressure, dehydrated methanol for organic synthesis (23 mL) was added, and the mixture was suspended by stirring in an ice bath for 1 hr. After filtration under reduced pressure, the crystals were washed with cold methanol and dried at room temperature under normal pressure to give the object compound. White crystalline powder, 506.5 mg, yield 54%, $^1$H-NMR (500 MHz, CDCl$_3$, TMS) δ 0.99 (dd, J=15.3 Hz, 6.8 Hz, 6H), 1.30-1.41 (m, 2H), 2.43-2.56 (m, 2H), 7.24-7.34 (m, 8H), 7.37-7.50 (m, 8H). $^{13}$C-NMR (125 MHz, CDCl$_3$, CDCl$_3$) δ15.61-15.74 (m), 27.17-27.34 (m), 36.31-36.61 (m), 128.25-128.35 (m), 128.50-128.90 (m), 133.18-133.92 (m), 136.38-137.57 (m). $^{31}$P-NMR (202 MHz, CDCl$_3$, H$_3$PO$_4$) δ-0.36 (s).

Example 7

Synthesis of (S,S)-Xylyl-Skewphos-borane complex

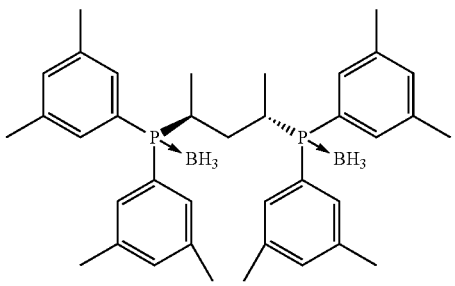

Under an argon atmosphere, into a 200 mL Schlenk flask were added 3,5-dixylylphosphine-borane complex (5.00 g) [mw. 256.13, 19.5 mmol], (2R,4R)-pentanediol ditosylate (3.83 g) [mw. 412.52, 9.3 mmol], potassium tert-butoxide (2.40 g) [mw. 112.21, 21.4 mmol] and dehydrated tetrahydrofuran for organic synthesis (135 mL), and the mixture was stirred at room temperature for 29 hr. Insoluble matter was filtered off through silica gel, and the filtrate was concentrated under reduced pressure. Dehydrated methanol for organic synthesis (120 mL) was added, and the mixture was suspended by stirring at room temperature for 1.5 hr. After filtration under reduced pressure, the crystals were washed with methanol and dried in vacuo at 50° C. to give the object compound. White crystalline powder, 3.52 g, yield 65%, $^1$H-NMR (500 MHz, CDCl$_3$, TMS) δ 0.27-1.25 (br, 6H), 1.04 (dd, J=16.4 Hz, 6.9 Hz, 6H), 1.57-1.70 (m, 2H), 2.29 (d, J=9.8 Hz, 24H), 2.41-2.56 (m, 2H), 7.07 (s, 4H), 7.19-7.23 (m, 8H). $^{13}$C-NMR (125 MHz, CDCl$_3$, CDCl$_3$) δ13.41, 21.31, 25.65-26.38 (m), 31.65, 127.18-128.59 (m), 129.73-130.66 (m), 132.93, 138.02-138.60 (m). $^{31}$P-NMR (202 MHz, CDCl$_3$, H$_3$PO$_4$) δ 24.65 (brs).

Example 8

Synthesis of (S,S)-Xylyl-Skewphos

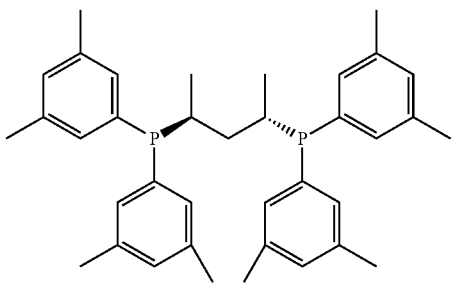

Under an argon atmosphere, into a 50 mL Schlenk flask were added (2S,4S)-Xylyl-Skewphos-BH$_3$ (1.00 g) [mw.

580.38, 1.72 mmol] and diethylamine (18 mL) [d=0.70, mw. 73.14, 220.1 mmol], and the mixture was stirred at 60° C. for 5 hr. After cooling in an ice bath, methanol (18 mL) was added, and the mixture was stirred in an ice bath for 30 min. The mixture was concentrated under reduced pressure, dehydrated methanol for organic synthesis (18 mL) was added, and the mixture was suspended by stirring at room temperature for 1 hr. After filtration under reduced pressure, the crystals were washed with methanol and dried at room temperature under normal pressure to give the object compound. White crystalline powder, 844.0 mg, yield 89%, $^1$H-NMR (500 MHz, CDCl$_3$, TMS) δ 0.98 (dd, J=15.3 Hz, 6.8 Hz, 6H), 1.32-1.40 (m, 2H), 2.25 (d, J=6.3 Hz, 24H), 2.41-2.47 (m, 2H), 6.91 (s, 4H), 7.05 (d, J=7.6 Hz, 8H). $^{13}$C-NMR (125 MHz, CDCl$_3$, CDCl$_3$) δ15.84-15.97 (m), 21.31, 27.01-27.18 (m), 36.53-36.83 (m), 130.46, 131.20-131.46 (m), 136.28-137.30 (m), 137.52 (m). $^{31}$P-NMR (202 MHz, CDCl$_3$, H$_3$PO$_4$) δ −0.63 (s).

Example 9

Synthesis of [Rh(cod)(S,S)-ptbp-skewphos]OTf

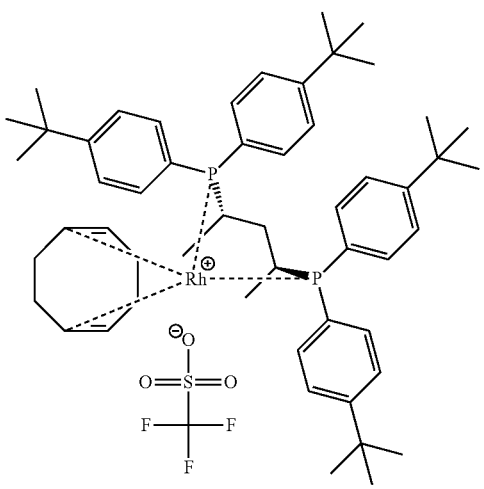

Under an argon atmosphere, into a 50 mL Schlenk flask were added [Rh(cod)$_2$]OTf (491 mg) [mw. 468.34, 1.048 mmol] and (2S,4S)-PTBP-Skewphos (767 mg) [mw. 664.92, 1.153 mmol], and the flask was substituted with argon. Dehydrated acetone for organic synthesis (10 mL) was added by argon pressure supply, and the mixture was stirred at 40-50° C. for 1 hr. The mixture was concentrated under reduced pressure, ethyl acetate (10 mL) was added, and the mixture was suspended by stirring at 50° C. for 20 min. Furthermore, after concentration under reduced pressure, ethyl acetate (5 mL) was added, and the mixture was suspended by stirring at 50° C. for 20 min for solid-liquid separation. The mixture was washed with ethyl acetate (5 mL) and, after solid-liquid separation, dried in vacuo to give the object compound. Yellow crystalline powder, 977.6 mg, yield 91%, $^{31}$P-NMR (202 MHz, CDCl$_3$, H$_3$PO$_4$) δ(ppm) 24.87 (d, J$_{Rh-P}$=141.7 Hz).

Reference Example 1

Synthesis of benzyl 2-oxopyrrolidine-1-carboxylate

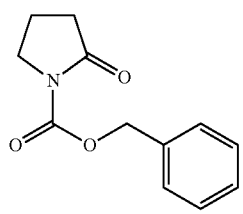 [SMILES: O=C1CCCN1C(=O)OCc1ccccc1]

Into a 3 L four-mouthed flask equipped with Dean-Stark trap were added PRD (125.00 g) [mw. 85.10, 1.47 mol] and toluene (2500 mL), and the mixture was dissolved. Granular sodium hydroxide (59.34 g) [mw. 40.00, 1.48 mol, 1.01 eq.] was added, and the mixture was heated to the reflux temperature. After refluxing for 6 hr, water in the system was evaporated. (dehydration amount about 24 mL) After cooling to 5° C., Cbz-Cl (252.37 g) [mw. 170.59, 1.48 mol, 1.01 eq.] was added dropwise within the range of 5-12° C. over 1 hr, and the mixture was stirred at around 10° C. for 1 hr. Water (625 mL) was added, and the mixture was partitioned by stirring for 10 min. To the organic layer was added 5% aqueous potassium hydrogen sulfate solution (625 mL), and the mixture was partitioned by stirring for 10 min. Furthermore, the organic layer was washed twice with water (625 mL). To the organic layer was added anhydrous magnesium sulfate (50 g), and the mixture was dried. Insoluble matter was filtered off, and the filtrate was washed with toluene (125 mL). The filtrate was concentrated under reduced pressure, to the concentrate was added tetrahydrofuran (500 mL) to dissolve the concentrate, and the solvent was replaced to give the object compound. Colorless liquid, 306.91 g, yield 95.2%. For analysis, 12.63 g was extracted and purified by silica gel column. (silica gel amount: 150 g, eluent: n-hexane/ethyl acetate=1/1, Rf=0.45) The effective fraction was concentrated under reduced pressure to give a colorless clear liquid. IR (liquid film) 3063 (υCH(Ar), 2982-2895 (υCH), 1788-1717 (υC═O), 1383 (δCH), 1240 (υC—O). $^1$H-NMR (300 MHz, CDCl$_3$, TMS) δ 1.94-2.04 (m, 2H), 2.49 (t, J=8.1 Hz, 2H), 3.78 (t, J=7.1 Hz, 2H), 5.24 (s, 2H), 7.30-7.42 (m, 5H). $^{13}$C-NMR (75 MHz, CDCl$_3$, CDCl$_3$) δ 17.05, 32.27, 45.96, 67.33, 127.68, 127.90, 128.13, 135.06, 150.98, 173.63. MS (ESI): m/z 219 M$^+$. Anal.

calcd. for $C_{12}H_{13}NO_3$ C, 65.74; H, 5.98; N, 6.39; O, 21.89 found C, 65.46; H, 5.99; N, 6.35.

Reference Example 2

Synthesis of benzyl 3-(2-methoxyacetyl)-2-oxopyrrolidine-1-carboxylate potassium salt

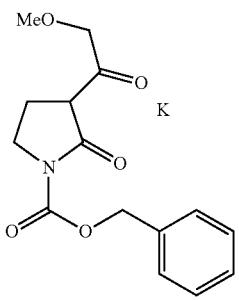

Under a nitrogen stream, into a 10 L separable flask were added 1,1,1,3,3,3-hexamethyldisilazane (388.90 g) [mw. 161.39, 2.41 mol, 1.9 eq.] and tetrahydrofuran (1167 mL), and the mixture was dissolved. After cooling to −70° C., 1.6 mol/L normal butyllithium/normal hexane solution (1500 mL) [2.40 mol, 1.9 eq.] was added within the range of −69 to −52° C. over 1 hr, and the mixture was stirred at around −80° C. for 1 hr. A solution of benzyl 2-oxopyrrolidine-1-carboxylate (278.26 g) [mw. 219.24, 1.27 mol] in tetrahydrofuran (279 mL) was added at −77 to −64° C. over 70 min. The mixture was stirred at around −80° C. for 80 min and a solution of methoxyacetic acid chloride (154.35 g) [mw. 108.52, 1.42 mol, 1.1 eq.] in tetrahydrofuran (279 mL) was added within the range of −77 to −52° C. over 25 min, and the mixture was stirred at around −80° C. for 80 min. A 6 mol/L aqueous hydrochloric acid solution (696 mL) was added within the range of −77 to −46° C. over 30 min. Water (279 mL) and toluene (1400 mL) were added at not more than 10° C., and the mixture was warmed to 20° C. and stirred at the same temperature for 30 min. After partitioning, the organic layer was washed so with water (835 mL) and concentrated under reduced pressure. The concentrate was dissolved in ethanol (1848 mL). 40% Aqueous potassium carbonate solution (1316 g) was added, and the mixture was stirred for 5 hr. To the crystallization liquid were added water (1316 mL) and ethyl acetate (2218 mL), and the mixture was stirred for 30 min. After partitioning, the organic layer was concentrated under reduced pressure, and the concentrate was dissolved in ethanol (543 mL). To the dissolved liquid was added ethyl acetate (5415 mL) to allow for crystallization and the mixture was aged for 90 min. The obtained crystals were collected by filtration under reduced pressure, washed with ethanol/ethyl acetate=1/10 (445 mL), and dried in vacuo at 50° C. to give the object compound. White crystalline powder, 198.30 g, yield 47.4%, $^1$H-NMR (500 MHz, $D_2O$, TMS) δ 2.32 (t, J=8.04 Hz, 2H), 3.21-3.31 (m, 5H), 4.38 (s, 2H), 4.70 (s, 2H), 7.06-7.20 (m, 5H). $^{13}$C-NMR (125 MHz, $D_2O$) δ20.96, 43.02, 57.96, 67.05, 72.51, 96.54, 127.71, 128.26, 128.61, 135.89, 153.56, 170.63, 181.76.

Reference Example 3

Synthesis of benzyl 3-(2-methoxy-1-(phenylamino) ethylidene-2-oxopyrrolidine-1-carboxylate

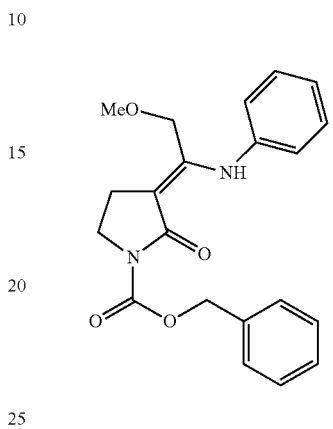

Into a 1 L four-mouthed flask equipped with Dean-Stark trap were added benzyl 3-(2-methoxyacetyl)-2-oxopyrrolidine-1-carboxylate potassium salt (50.00 g) [mw. 329.39, 151.8 mmol], 1 mol/L aqueous hydrochloric acid solution (250 mL) and toluene (500 mL), and the mixture was stirred for 1 hr. After partitioning, the organic layer was washed with water (250 mL), and the mixture was partitioned. To the organic layer were added aniline (12.72 g) [mw. 93.13, 136.6 mmol, 0.9 eq.], p-toluenesulfonic acid monohydrate (0.29 g) [mw. 190.22, 1.5 mmol, 0.01 eq.] and cyclohexane (250 mL). The mixture was heated to reflux temperature, and about 400 mL was evaporated from the system in 2 hr. In this case, to keep the amount of the solution in the system unchanged, a mixed solvent of toluene/cyclohexane (2/3) in the same amount as the evaporated amount was added at a constant rate. (refluxing temperature 83→93° C.) After cooling to 25° C., 5% aqueous acetic acid solution was added, and the mixture was stirred for 10 min and partitioned. To the organic layer was added 5% aqueous sodium bicarbonate solution (250 mL), and the mixture was partitioned. Furthermore, the organic layer was washed twice with water (250 mL). The organic layer was concentrated under reduced pressure, the concentrate was dissolved in methanol (500 mL). Activated carbon (5 g) was added, and the mixture was stirred for 15 min. The activated carbon was filtered off, and washed with methanol (50 mL). The filtrate was concentrated under reduced pressure, to the concentrate was added ethyl acetate (250 mL), and the solvent was replaced. The concentrate was dissolved in ethyl acetate (25 mL), and cooled to −5° C. Seed crystal was inoculated and normal heptane (200 mL) was added to the crystallized liquid at around 0° C. After warming to 25° C., the mixture was aged for 1 hr, and the crystals were collected by filtration under reduced pressure, washed with a mixed solvent of normal heptane/ethyl acetate (10/1), and dried in vacuo at 45° C. to give the object compound. Orange crystalline powder, 37.63 g, yield 67.6%, $^1$H-NMR (500 MHz, $CDCl_3$, TMS) δ 2.73-2.85 (m, 2H), 3.34 (s, 3H), 3.76-3.85 (m, 2H), 4.02 (s, 2H), 5.30 (s, 2H), 7.06-7.16 (m, 3H), 7.27-7.49 (m, 7H), 10.55 (s, 1H). $^{13}$C-NMR (125 MHz, $CDCl_3$, $CDCl_3$) δ20.98, 43.62, 58.47, 67.60, 68.02, 98.69, 122.80, 124.41, 128.07, 128.18, 128.55, 129.20, 135.88, 139.29, 150.55, 152.30, 169.95.

Reference Example 4

Synthesis of benzyl 3-(1-((4-fluorophenyl)amino)-2-methoxyethylidene)-2-oxopyrrolidine-1-carboxylate

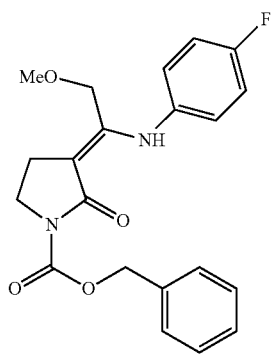 [SMILES: COC/C(Nc1ccc(F)cc1)=C1\CCN(C(=O)OCc2ccccc2)C1=O]

Into a 100 mL eggplant-shaped flask were added benzyl 3-(2-methoxyacetyl)-2-oxopyrrolidine-1-carboxylate potassium salt (2.93 g) [mw. 329.39, 8.9 mmol], 1 mol/L hydrochloric acid (16 mL) [16 mmol] and toluene (32 mL), and the mixture was stirred for 20 min. After partitioning, the organic layer was concentrated under reduced pressure, and to the concentrate were added toluene (12 mL), cyclohexane (36 mL), p-toluenesulfonic acid monohydrate (18.0 mg) [mw. 190.22, 0.09 mmol] and p-fluoroaniline (0.99 g) [mw. 111.12, 8.9 mmol]. Dean-Stark trap was set, and the mixture was subjected to dehydration reflux for 2 hr. After cooling to 25° C., 5 w/w % aqueous sodium bicarbonate solution (10 mL) was added and the mixture was partitioned. The organic layer was washed with water (10 mL), dried over magnesium sulfate and, after filtration, concentrated under reduced pressure. To the concentrate were added toluene (20 mL) and 10 w/w % aqueous citric acid solution, and the mixture was stirred and partitioned. The organic layer was dried over magnesium sulfate, filtered and concentrated under reduced pressure. Yellow candy-like product, 2.56 g, yield 74.8%. $^1$H-NMR (500 MHz, CDCl$_3$, TMS) δ 2.77 (s, 1H), 3.31 (s, 3H), 3.81 (t, J=5.0 Hz, 2H), 3.96 (s, 2H), 5.30 (s, 2H), 6.90-7.12 (m, 5H), 7.22-7.49 (m, 5H), 10.44 (s, 1H).

Reference Example 5

Synthesis of benzyl 3-(1-((4-bromophenyl)amino)-2-methoxyethylidene)-2-oxopyrrolidine-1-carboxylate

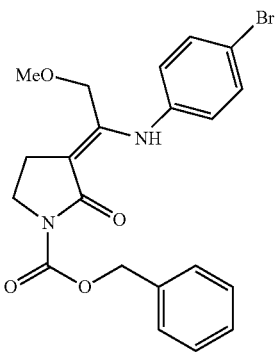 [SMILES: COC/C(Nc1ccc(Br)cc1)=C1\CCN(C(=O)OCc2ccccc2)C1=O]

Into a 100 mL eggplant-shaped flask were added benzyl 3-(2-methoxyacetyl)-2-oxopyrrolidine-1-carboxylate potassium salt (4.95 g) [mw. 329.39, 15.0 mmol], 1 mol/L hydrochloric acid (25 mL) [25 mmol] and toluene (50 mL), and the mixture was stirred for 20 min. After partitioning, the organic layer was dried over magnesium sulfate, filtered and concentrated under reduced pressure. To the concentrate were added toluene (19 mL), cyclohexane (57 mL), p-toluenesulfonic acid monohydrate (29.0 mg) [mw. 190.22, 0.15 mmol] and parabromoaniline (2.58 g) [mw. 172.02, 15.0 mmol]. Dean-Stark trap was set, and the mixture was subjected to dehydration reflux for 2 hr. After cooling to 25° C., 5 w/w % aqueous sodium bicarbonate solution (10 mL) was added to allow for partitioning. The organic layer was washed with water (10 mL), dried over magnesium sulfate, filtered and concentrated under reduced pressure. To the concentrate was added methanol (19 mL), and the mixture was dissolved. Activated carbon (0.5 g) was added, and the mixture was stirred. The activated carbon was filtered off, the mother liquor was concentrated under reduced pressure, and to the concentrate were added ethyl acetate (2 mL) and diisopropyl ether (20 mL). The mixture was left standing in a freezer at −16° C. overnight, and crystallization was confirmed. The mixture was aged at room temperature for 1 hr. After filtration under reduced pressure, the crystals were washed with ethyl acetate/diisopropyl ether (1/10), and dried under reduced pressure at 50° C. Yellow crystals, 4.12 g, yield 61.6%, $^1$H-NMR (500 MHz, CDCl$_3$, TMS) δ 2.78 (t, J=7.7 Hz, 2H), 3.35 (s, 3H), 3.76-3.89 (m, 2H), 4.00 (s, 2H), 5.30 (s, 2H), 6.99 (d, J=8.8 Hz, 5H), 7.28-7.52 (m, 7H), 10.49 (s, 1H). $^{13}$C-NMR (125 MHz, CDCl₃, CDCl₃) δ 20.95, 43.60, 58.55, 67.74, 67.97, 99.87, 117.24, 124.08, 128.13, 128.58, 132.24, 135.78, 138.56, 149.72, 152.24, 169.92.

Reference Example 6

Synthesis of benzyl 3-(1-((4-chlorophenyl)amino)-2-methoxyethylidene)-2-oxopyrrolidine-1-carboxylate

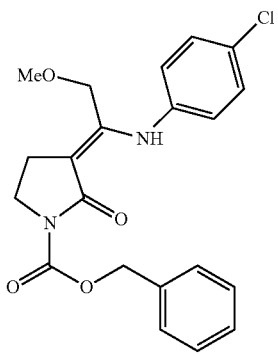

Into a 200 mL four-mouthed flask were added benzyl 3-(2-methoxyacetyl)-2-oxopyrrolidine-1-carboxylate potassium salt (6.60 g) [mw. 329.39, 20.0 mmol], 1 mol/L aqueous hydrochloric acid solution (33 mL) and toluene (60 mL), and the mixture was stirred at room temperature for 30 min. After partitioning, the organic layer was washed with water (33 mL), and dried over magnesium sulfate. After filtration, p-chloroaniline (2.56 g) [mw. 127.57, 20.0 mmol], p-toluenesulfonic acid monohydrate (0.038 g) [mw. 190.22, 0.2 mmol] and cyclohexane (33 mL) were added. Dean-Stark trap was set, and distillation by thermal dehydration was performed for 90 min. After cooling to room temperature, 5 w/w % aqueous acetic acid solution (33 mL) was added to allow for partitioning. The organic layer was washed successively with 5 w/w % aqueous sodium bicarbonate solution (33 mL) and water (33 mL), further washed with water (33 mL), dried over magnesium sulfate, filtered and concentrated under reduced pressure. To the concentrate were added methanol (q.s.) and activated carbon (1 g), and the mixture was stirred at room temperature for 30 min. After filtration, the mother liquor was concentrated under reduced pressure. The concentrate was purified by basic silica gel column (silica gel amount; 25 g, eluent:toluene, Rf=0.2), and the effective fraction was concentrated under reduced pressure. The concentrate was dissolved in ethyl acetate (3 mL) and diisopropyl ether (30 mL). The mixture was cooled in a freezer to produce crystal core. The mixture was suspended by stirring at room temperature for 1 hr. After filtration under reduced pressure, the crystals were washed with a mixed solvent of ethyl acetate/diisopropyl ether (1/10) (10 mL), and dried at 45° C. under reduced pressure to give the object compound. Pale-yellow white crystal, 2.50 g, yield 31.2%, ¹H-NMR (500 MHz, CDCl₃, TMS) δ 2.78 (t, J=7.5 Hz, 2H), 3.34 (s, 3H), 3.81 (t, J=8.0 Hz, 2H), 3.99 (s, 2H), 5.29 (s, 2H), 7.03-7.05 (m, 2H), 7.25-7.44 (m, 7H), 10.50 (s, 1H). ¹³C-NMR (125 MHz, CDCl₃, CDCl₃) δ 20.95, 43.61, 58.53, 67.71, 67.96, 99.68, 123.83, 128.11, 128.25, 128.57, 129.28, 129.67, 135.81, 138.06, 149.88, 152.23, 169.93.

Reference Example 7

Synthesis of benzyl 3-(1-((4-methoxyphenyl)amino)-2-methoxyethylidene)-2-oxopyrrolidine-1-carboxylate

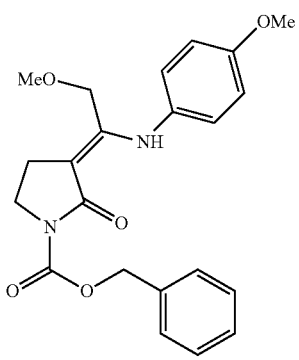 [SMILES: COC/C(Nc1ccc(OC)cc1)=C1\CCN(C(=O)OCc2ccccc2)C1=O]

Into a 100 mL eggplant-shaped flask were added benzyl 3-(2-methoxyacetyl)-2-oxopyrrolidine-1-carboxylate potassium salt (4.94 g) [mw. 329.39, 15.0 mmol], 1 mol/L hydrochloric acid (25 mL) [25 mmol] and toluene (50 mL), and the mixture was stirred for 20 min. After partitioning, the organic layer was dried over magnesium sulfate. After filtration, to the mother liquor were added cyclohexane (30 mL), p-toluenesulfonic acid monohydrate (29.0 mg) [mw. 190.22, 0.15 mmol] and p-methoxyaniline (1.85 g) [mw. 123.15, 15.0 mmol]. Dean-Stark trap was set, and the mixture was subjected to dehydration reflux for 30 min. After cooling to 25° C., 5 w/w % aqueous sodium bicarbonate solution (25 mL) was added to allow for partitioning. The organic layer was washed with 5 w/w % aqueous acetic acid solution (25 mL), further washed with 5 w/w % aqueous sodium bicarbonate solution (25 mL), dried over magnesium sulfate, filtered, concentrated under reduced pressure and purified by basic silica gel column chromatography (silica gel amount: 100 g, eluent:toluene, Rf=0.2). The effective section was concentrated under reduced pressure. Yellow candy-like product, 3.63 g, yield 61.0%, ¹H-NMR (500 MHz, CDCl₃, TMS) δ 2.74-2.77 (m, 2H), 3.29 (s, 3H), 3.75-3.80 (m, 5H), 3.95 (s, 2H), 5.28 (s, 2H), 6.83 (d, J=8.8 Hz, 2H), 7.04 (d, J=8.8 Hz, 2H), 7.25-7.38 (m, 3H), 7.43 (d, J=7.2 Hz, 2H), 10.41 (s, 1H).

256.1182 [M−H]⁻. Found: C, 47.00; H, 5.87; N, 4.53%. Calcd for C$_{12}$H$_{11}$NO$_5$K-0.1H$_2$O: C, 47.29; H, 5.84; N, 4.28%.

Reference Example 8

Synthesis of tert-butyl 3-(2-methoxyacetyl)-2-oxopyrrolidine-1-carboxylate potassium salt

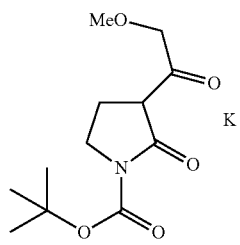

Reference Example 9

Synthesis of tert-butyl 3-(2-methoxy-1-(phenylamino)ethylidene)-2-oxopyrrolidine-1-carboxylate

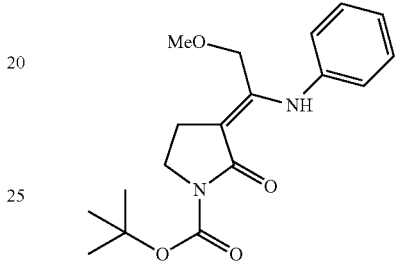

Under a nitrogen stream, into a 500 mL four-mouthed flask were added 1,1,1,3,3,3-hexamethyldisilazane (25.83 g) [mw. 161.39, 0.160 moL, 2 eq.] and tetrahydrofuran (80 mL), and the mixture was dissolved. After cooling to −70° C., 1.6 mol/L normal butyllithium/normal hexane solution (100 mL) [0.160 mol, 2 eq.] was added within the range of −70 to −55° C. After stirring at the same temperature for 20 min, a solution (15 mL) of N-Boc-2-pyrrolidone (14.82 g) [mw. 185.23, 0.080 mol] in tetrahydrofuran was added within the range of −72 to −68° C. After stirring at the same temperature for 1 hr, a solution (15 mL) of methoxyacetic acid chloride (9.55 g) [mw. 108.52, 0.088 mol] in tetrahydrofuran was added within the range of −72 to −68° C. After stirring at the same temperature for 1 hr, 6 mol/L aqueous hydrochloric acid solution (44 mL) [0.264 mol] was added at not more than −10° C. to quench the reaction. Water (15 mL) and toluene (88 mL) were added at 0-15° C. to allow for partitioning. The organic layer was washed twice with water (20 mL), dried over magnesium sulfate, filtered and concentrated under reduced pressure to give a yellow oil (20.44 g). To this concentrate were added ethanol (100 mL) and 40 w/w % aqueous potassium carbonate solution (83.0 g) [mw. 138.21, 0.240 moL, 3 eq.], and the mixture was stirred at room temperature for 16 hr. Ethyl acetate (140 mL) and water (83 mL) were added to allow for partitioning. The organic layer was concentrated under reduced pressure, and the concentrate was dissolved in ethanol (25 mL). To the dissolved liquid was added ethyl acetate (300 mL), and the mixture was stirred at room temperature for 6 hr. The crystals were collected by filtration to give the object compound. White crystals, 2.39 g, yield 10.2%, ¹H-NMR (500 MHz, D$_2$O) δ 1.50 (s, 9H), 2.52 (t, J=8.0 Hz, 2H), 3.33 (s, 3H), 3.61 (t, J=8.3 Hz, 2H), 4.44 (s, 2H). ¹³C-NMR (125 MHz, D$_2$O) δ 20.97, 27.96, 43.35, 58.16, 72.71, 82.34, 96.00, 153.32, 170.32, 181.68. MS (ESI) m/z 296.0873 [M+K]⁺, Into a 200 mL four-mouthed flask were added tert-butyl 3-(2-methoxyacetyl)-2-oxopyrrolidine-1-carboxylate potassium salt (9.00 g) [mw. 295.37, 30.47 mmol], 1 mol/L aqueous hydrochloric acid solution (50 mL) and toluene (90 mL), and the mixture was stirred at room temperature for 10 min. After partitioning, the organic layer was washed with water (50 mL), and dried over magnesium sulfate. After filtration, aniline (2.84 g) [mw. 93.13, 30.50 mmol], p-toluenesulfonic acid monohydrate (0.58 g) [mw. 190.22, 3.05 mmol] and cyclohexane (50 mL) were added. Dean-Stark trap was set, and distillation by thermal dehydration was performed for 1 hr. After cooling to room temperature, 5 w/w % aqueous acetic acid solution (50 mL) was added to allow for partitioning. The organic layer was washed successively with 5 w/w % aqueous sodium bicarbonate solution (50 mL) and water (50 mL), further washed with water (50 mL), dried over magnesium sulfate, filtered and concentrated under reduced pressure. To the concentrate were added methanol (78 mL) and activated carbon (0.78 g), and the mixture was stirred at room temperature for 1 hr. After filtration, the mother liquor was concentrated under reduced pressure, and the solvent was replaced with ethyl acetate. To the concentrate was added diisopropyl ether (22 mL) to allow for crystallization, and the crystals were aged for 1 hr. After filtration under reduced pressure, the crystals were washed with diisopropyl ether (8 mL), and dried at 40° C. under reduced pressure to give the object compound. Pale-yellow crystals, 3.47 g, yield 34.3%, ¹H-NMR (500 MHz, DMSO-d$_6$, TMS) δ 1.47 (s, 9H), 2.70 (t, J=7.7 Hz, 2H), 3.26 (s, 3H), 3.65 (t, J=8.1 Hz, 2H), 4.06 (s, 2H), 7.07-7.14 (m, 3H), 7.31-7.35 (m, 2H), 10.34 (s, 1H). ¹³C-NMR (125 MHz, DMSO-d$_6$) δ 20.29, 27.74, 43.23, 57.83, 67.40, 89.97, 100.10, 121.40, 123.48, 129.20, 139.43, 148.97, 150.33, 169.16. MS (ESI) m/z 333.1776 [M+H]⁺, 355.1629 [M+Na]⁺, 331.1672 [M−H]⁻. Found: C, 65.04; H, 7.28; N, 8.43%. Calcd for C₁₈H₂₄N₂O₄: C, 64.97; H, 7.20; N, 8.37%.

Reference Example 10

Synthesis of allyl 2-oxopyrrolidine-1-carboxylate

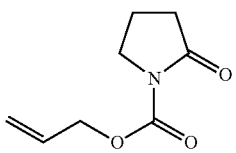

Into a 500 mL four neck flask were added 2-pyrrolidone (17.02 g) [mw. 85.10, 200 mmol] and toluene (340 mL), and the mixture was dissolved. Powder sodium hydroxide (8.00 g) [mw. 40.00, 200 mmol] was added thereto, Dean-Stark trap was set, and the mixture was subjected to dehydration reflux for 4 hr. After cooling to 0° C., allyloxycarbonyl chloride (20.10 g) [mw. 120.53, 167 mmol] was added at not more than 30° C., and the mixture was stirred at 25° C. for 30 min. Water (85 mL) and tetrahydrofuran (85 mL) were added to allow for partitioning. The organic layer was washed with 5 w/w aqueous potassium hydrogen sulfate solution (85 mL), and further washed twice with water (85 mL). The organic layer was concentrated under reduced pressure, and the solvent was replaced with tetrahydrofuran. Pale-yellow oil, 19.28 g, yield 57.0%, ¹H-NMR (500 MHz, CDCl₃, TMS) δ 2.09 (quin, J=7.7 Hz, 2H), 2.54 (t, J=8.2 Hz, 2H), 3.80-3.86 (m, 2H), 4.70-4.77 (m, 2H), 5.25-5.38 (m, 1H), 5.38-5.45 (m, 1H), 5.88-6.04 (m, 1H). ¹³C-NMR (125 MHz, CDCl₃, CDCl₃) δ 17.57, 32.78, 46.42, 66.87, 118.76, 131.57, 151.38, 173.98.

Reference Example 11

Synthesis of allyl 3-(2-methoxy-1-(phenylamino) ethylidene)-2-oxopyrrolidine-1-carboxylate

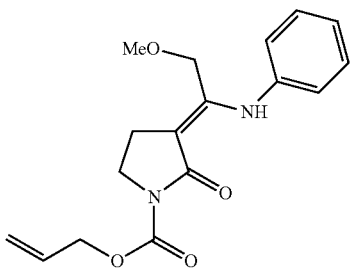 [SMILES: C=CCOC(=O)N1CC/C(=C(\COC)Nc2ccccc2)C1=O]

Under a nitrogen stream, into a 500 mL four-mouthed flask were added 1,1,1,3,3,3-hexamethyldisilasane (25.83 g) [mw. 161.39, 160 mmol, 1.8 eq.] and tetrahydrofuran (78 mL), and the mixture was dissolved. After cooling to −70° C., 1.6 mol/L normal butyllithium/normal hexane solution (100 mL) [160 mmol, 1.8 eq.] was added within the range of −70--60° C. After stirring at the same temperature for 30 min, a solution (20 mL) of allyl 2-oxopyrrolidine-1-carboxylate (15.04 g) [mw. 169.18, 90 mmol] in tetrahydrofuran was added within the range of −78 to −70° C. After stirring at the same temperature for 50 min, a solution (20 mL) of methoxyacetic acid chloride (9.64 g) [mw. 108.52, 90 mmol] in tetrahydrofuran was added within the range of −78 to −62° C. After stirring at the same temperature for 30 min, 6 mol/L aqueous hydrochloric acid solution (50 mL) [300 mmol] was added at not more than −30° C. to quench the reaction. After warming to 25° C., water (25 mL) and toluene (100 mL) were added to allow for partitioning. The organic layer was dried over magnesium sulfate, filtered and concentrated under reduced pressure to give a yellow oil. Toluene (28 mL), aniline (4.20 g) [mw. 93.13, 45 mmol], p-toluenesulfonic acid monohydrate (170.0 mg) [mw. 190.22, 0.9 mmol] and cyclohexane (84 mL) were added thereto. Dean-Stark trap was set, and the mixture was subjected to dehydration reflux for 1.5 hr. After cooling to 25° C., 10 w/w % aqueous citric acid solution (56 mL) and toluene (28 mL) were added to allow for partitioning. Furthermore, the organic layer was washed with 5 w/w % aqueous sodium bicarbonate solution (56 mL), dried over magnesium sulfate, filtered, and concentrated under reduced pressure. The concentrate was purified by basic silica gel. (silica gel amount: 100 g, eluent:toluene) The effective fraction was concentrated under reduced pressure, and normal hexane (56 mL) and ethyl acetate (21 mL) were added to allow for crystallization. The crystals were aged, filtered under reduced pressure, washed with a mixed solvent of normal hexane/ethyl acetate=8/3 (33 mL), and dried under reduced pressure at 50° C. Yellow crystals, 4.85 g, yield 17.2%, ¹H-NMR (500 MHz, CDCl₃, TMS) δ2.72-2.90 (m, 2H), 3.35 (s, 3H), 3.73-3.88 (m, 2H), 4.04 (s, 2H), 4.76 (d, J=5.7 Hz, 2H), 5.21-5.50 (m, 2H), 5.88-6.10 (m, 1H), 7.04-7.16 (m, 3H), 7.28-7.39 (m, 2H), 10.44-10.66 (s, 1H). ¹³C-NMR (125 MHz, CDCl₃, CDCl₃) δ20.99, 43.61, 58.49, 66.71, 68.04, 98.71, 118.66, 122.77, 124.41, 129.21, 131.95, 139.29, 150.57, 152.27, 169.92.

Reference Example 12

Synthesis of (9H-fluoren-9-yl)methyl 2-oxopyrrolidine-1-carboxylate

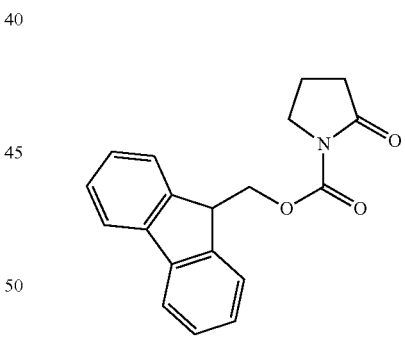

Into a 500 mL four neck flask were added 2-pyrrolidone (8.51 g) [mw. 85.10, 100 mmol] and toluene (170 mL), and the mixture was dissolved. Powder sodium hydroxide (4.00 g) [mw. 40.00, 100 mmol] was added thereto, Dean-Stark trap was set, and the mixture was subjected to dehydration reflux for 4 hr. After cooling to 0° C., Fmoc-Cl (25.70 g) [mw. 258.70, 99 mmol] was added at not more than 5° C., the mixture was stirred at 25° C. for 2 hr, and water (43 mL) was added to allow for partitioning. The organic layer was washed with 5 w/w aqueous potassium hydrogen sulfate solution (43 mL), and further washed twice with water (43 mL). The organic layer was dried over magnesium sulfate, filtered and concentrated under reduced pressure. Pale-yellow oil, 30.56 g, yield 99.4%, ¹H-NMR (500 MHz, CDCl₃, TMS) δ 1.13 (d, J=6.3 Hz, 1H), 2.04 (quin, J=7.7 Hz, 2H), 2.57 (t, J=8.2 Hz, 2H), 3.75-3.82 (m, 2H), 4.49 (d, J=7.6 Hz, 2H), 7.30-7.36 (m, 2H), 7.37-7.45 (m, 2H), 7.70-7.79 (m, 4H). $^{13}$C-NMR (125 MHz, CDCl$_3$, CDCl$_3$) δ 17.56, 32.87, 46.41, 46.72, 68.59, 119.97, 125.35, 127.22, 127.87, 141.31, 143.53, 151.75, 173.79.

Reference Example 13

Synthesis of (9H-fluoren-9-yl)methyl 3-(2-methoxy-1-(phenylamino)ethylidene)-2-oxopyrrolidine-1-carboxylate

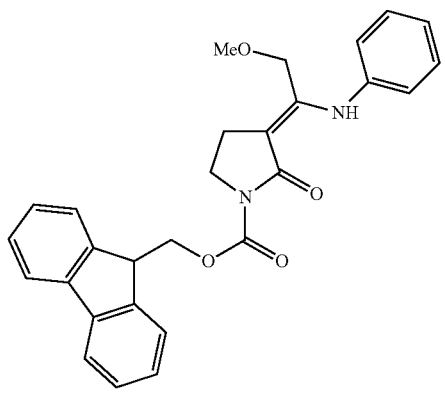 [SMILES: COC/C(Nc1ccccc1)=C1\CCN(C(=O)OCC2c3ccccc3-c3ccccc32)C1=O]

Under a nitrogen stream, into a 500 mL four-mouthed flask were added 1,1,1,3,3,3-hexamethyldisilasane (27.44 g) [mw. 161.39, 170 mmol, 1.7 eq.] and tetrahydrofuran (78 mL), and the mixture was dissolved. After cooling to −70° C., 1.6 mol/L normal butyllithium/normal hexane solution (105 mL) [168 mmol, 1.7 eq.] was added within the range of −70−−60° C. After stirring at the same temperature for 30 min, a solution (50 mL) of (9H-fluoren-9-yl)methyl 2-oxopyrrolidine-1-carboxylate (30.56 g) [mw. 307.34, 99 mmol] in tetrahydrofuran was added within the range of −78 to −70° C. After stirring at the same temperature for 90 min, methoxyacetic acid chloride (9.71 g) [mw. 108.52, 89 mmol] was added within the range of −78 to −67° C. After stirring at the same temperature for 90 min, 6 mol/L aqueous hydrochloric acid solution (55 mL) [330 mmol] was added at not more than −20° C. to quench the reaction. After warming to 25° C., water (55 mL) and toluene (110 mL) were added to allow for partitioning. The organic layer was washed with water (55 mL), dried over magnesium sulfate, filtered and concentrated under reduced pressure to give a yellow oil. Toluene (28 mL), aniline (8.40 g) [mw. 93.13, 90 mmol], p-toluenesulfonic acid monohydrate (170.0 mg) [mw. 190.22, 0.9 mmol] and cyclohexane (84 mL) were added thereto. Dean-Stark trap was set, and the mixture was subjected to dehydration reflux for 1 hr. After cooling to 25° C., 10 w/w % aqueous citric acid solution (60 mL) and toluene (28 mL) were added to allow for partitioning. Furthermore, the organic layer was washed with 5 w/w % aqueous sodium bicarbonate solution (60 mL), dried over magnesium sulfate, filtered and concentrated under reduced pressure. The concentrate was purified by basic silica gel. (silica gel amount: 250 g, eluent:toluene, Rf=0.9) The effective fraction was concentrated under reduced pressure, and preserved in a freezer to allow for crystallization. A mixed solvent of ethyl acetate/diisopropyl ether=1/5 (60 mL) was added, and the mixture was aged at room temperature. The crystals were collected by filtration under reduced pressure, acetone was added, and insoluble matter was filtered off. The mother liquor was concentrated under reduced pressure, a mixed solvent of ethyl acetate/diisopropyl ether=1/4 (25 mL) was added, and the mixture was suspended by stirring. After filtration under reduced pressure, the crystals were washed with a mixed solvent of ethyl acetate/diisopropyl ether=1/4, and dried under reduced pressure at 50° C. Yellow crystals, 2.60 g, yield 5.7%, $^1$H-NMR (500 MHz, CDCl$_3$, TMS) δ 2.83 (m, 2H), 3.36 (s, 3H), 3.81 (m, 2H), 4.05 (s, 2H), 4.35 (m, 1H), 4.50 (d, J=7.6 Hz, 2H), 7.10-7.17 (m, 3H), 7.29-7.36 (m, 4H), 10.60 (s, 1H). $^{13}$C-NMR (125 MHz, CDCl$_3$, CDCl$_3$) δ21.01, 43.63, 46.85, 58.54, 68.07, 68.25, 98.67, 119.94, 122.99, 124.52, 125.40, 127.20, 127.78, 129.24, 139.30, 141.30, 143.76, 150.63, 152.44, 169.89.

Reference Example 14

Synthesis of benzyl 8-fluoro-4-(methoxymethyl)-2,3,3a,4,5,9b-hexahydro-1H-pyrrolo[3,2-c]quinoline-1-carboxylate

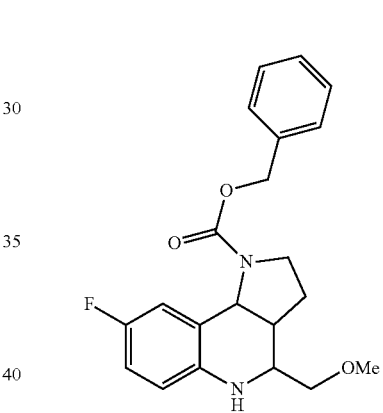

Into a 120 mL autoclave were added benzyl 3-(1-((4-fluorophenyl)amino)-2-methoxyethylidene)-2-oxopyrrolidine-1-carboxylate (262.0 mg) [mw. 384.40, 0.681 mmol] and asymmetric hydrogenation catalyst [Rh(cod)(S,S)-skewphos]OTf (10.9 mg) [mw. 800.65, 1.36*10$^{-2}$ mmol], and argon substitution was performed 7 times. Thereto was added dehydrated methanol (7 mL) by argon pressure supply, and the mixture was stirred for 10 min. Hydrogen pressure was raised to 5 MPa, and the mixture was stirred at 50° C. for 64 hr. The reaction mixture was allowed to cool to room temperature and depressurized. The reaction mixture was subjected to high performance liquid chromatography and area percentage of the resultant product, benzyl 8-fluoro-4-(methoxymethyl)-2,3,3a,4,5,9b-hexahydro-1H-pyrrolo[3,2-c]quinoline-1-carboxylate, was determined to find production at a ratio of 35%.

High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min.

Reference Example 15

Synthesis of benzyl 8-bromo-4-(methoxymethyl)-2,3,3a,4,5,9b-hexahydro-1H-pyrrolo[3,2-c]quinoline-1-carboxylate

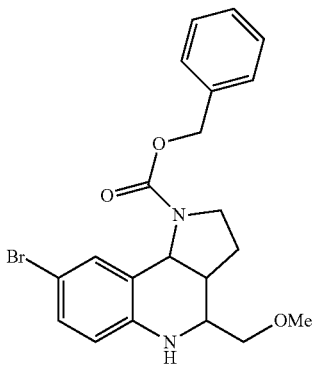

Into a 120 mL autoclave were added benzyl 3-(1-((4-bromophenyl)amino)-2-methoxyethylidene)-2-oxopyrrolidine-1-carboxylate (606.0 mg) [mw. 445.31, 1.36 mmol] and asymmetric hydrogenation catalyst [Rh(cod) (S,S)-skewphos)]OTf (10.9 mg) [mw. 800.65, 1.36*10$^{-2}$ mmol], and argon substitution was performed 7 times. Thereto was added dehydrated methanol (15 mL) by argon pressure supply, and the mixture was stirred for 10 min. Hydrogen pressure was raised to 5 MPa, and the mixture was stirred at 50° C. for 92 hr. The reaction mixture was allowed to cool to room temperature and depressurized. The reaction mixture was subjected to high performance liquid chromatography and area percentage of the resultant product, benzyl 8-bromo-4-(methoxymethyl)-2,3,3a,4,5,9b-hexahydro-1H-pyrrolo[3,2-c]quinoline-1-carboxylate, was determined to find production at a ratio of 2%.

Reference Example 16

Synthesis of benzyl 8-chloro-4-(methoxymethyl)-2,3,3a,4,5,9b-hexahydro-1H-pyrrolo[3,2-c]quinoline-1-carboxylate

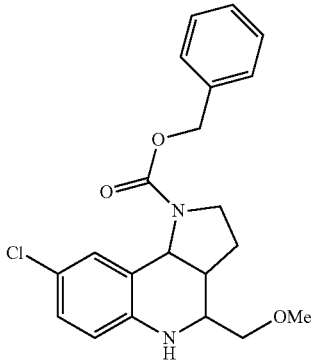 [SMILES: COCC1Nc2ccc(Cl)cc2C2C1CCN2C(=O)OCc1ccccc1]

Into a 120 mL stainless autoclave were charged benzyl 3-(1-((4-chlorophenyl)amino)-2-methoxyethylidene)-2-oxopyrrolidine-1-carboxylate (273.0 mg) [mw. 400.86, 0.681 mmol] and [Rh(cod) (S,S)-skewphos]OTf (10.9 mg) [mw. 800.65, 0.0136 mmol], and the system was substituted with argon. Deaeration-treated dehydrated methanol (10 mL) was added by argon pressure supply. Hydrogen was filled therein to 5 MPa, and the mixture was stirred at a reaction temperature of 50° C. for 14 hr. The reaction mixture was allowed to cool to room temperature and depressurized. The reaction mixture was subjected to high performance liquid chromatography and area percentage of the resultant product, benzyl 8-chloro-4-(methoxymethyl)-2,3,3a,4,5,9b-hexahydro-1H-pyrrolo[3,2-c]quinoline-1-carboxylate, was determined to find production at a ratio of 3%.

High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min.

Reference Example 17

Synthesis of benzyl 8-methoxy-4-(methoxymethyl)-2,3,3a,4,5,9b-hexahydro-1H-pyrrolo[3,2-c]quinoline-1-carboxylate

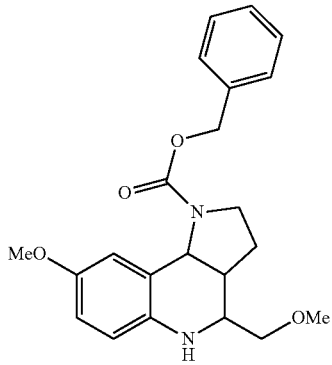 [SMILES: COCC1Nc2ccc(OC)cc2C2C1CCN2C(=O)OCc1ccccc1]

Into a 120 mL autoclave were added benzyl 3-(1-((4-methoxyphenyl)amino)-2-methoxyethylidene)-2-oxopyrrolidine-1-carboxylate (270.0 mg) [mw. 396.33, 0.681 mmol] and asymmetric hydrogenation catalyst [Rh(cod)(S,S)-skewphos)]OTf (10.9 mg) [mw. 800.65, 1.36*10$^{-2}$ mmol], and argon substitution was performed 7 times. Thereto was added dehydrated methanol (10 mL) by argon pressure supply, and the mixture was stirred for 10 min. Hydrogen pressure was raised to 5 MPa, and the mixture was stirred at 50° C. for 16 hr. The reaction mixture was allowed to cool to room temperature and depressurized. The reaction mixture was subjected to high performance liquid chromatography and area percentage of the resultant product, benzyl 8-methoxy-4-(methoxymethyl)-2,3,3a,4,5,9b-hexahydro-1H-pyrrolo[3,2-c]quinoline-1-carboxylate, was determined to find production at a ratio of 3%. High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min.

Reference Example 18

Synthesis of ethyl 4-(methoxymethyl)-2,3,3a,4,5,9b-hexahydro-1H-pyrrolo[3,2-c]quinoline-1-carboxylate

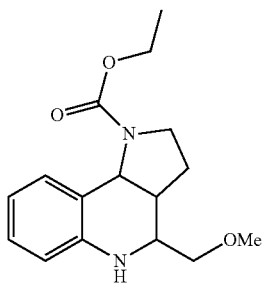 [SMILES: CCOC(=O)N1CCC2C(COC)Nc3ccccc3C21]

Into a 120 mL autoclave were added allyl 3-(2-methoxy-1-(phenylamino)ethylidene)-2-oxopyrrolidine-1-carboxylate (216.0 mg) [mw. 316.35, 0.682 mmol] and asymmetric hydrogenation catalyst [Rh(cod) (S,S)-skewphos)]OTf (10.9 mg) [mw. 800.65, 1.36*10⁻² mmol], and argon substitution was performed 7 times. Thereto was added dehydrated methanol (9 mL) by argon pressure supply, and the mixture was stirred for 10 min. Hydrogen pressure was raised to 5 MPa, and the mixture was stirred at 50° C. for 86 hr. The reaction mixture was allowed to cool to room temperature and depressurized. The reaction mixture was subjected to high performance liquid chromatography and area percentage of the resultant product, ethyl 4-(methoxymethyl)-2,3,3a,4,5,9b-hexahydro-1H-pyrrolo[3,2-c]quinoline-1-carboxylate, was determined to find production at a ratio of 49%. High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min.

Reference Example 19

Synthesis of (9H-fluoren-9-yl)methyl 4-methoxymethyl-2,3,3a,4,5,9b-hexahydro-1H-pyrrolo[3,2-c]quinoline-1-carboxylate

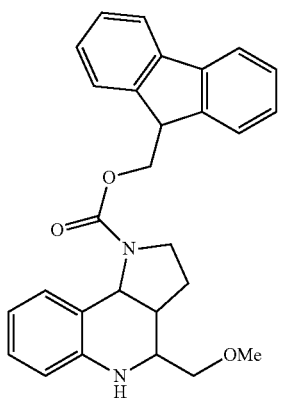 [SMILES: COCC1Nc2ccccc2C2C1CCN2C(=O)OCC1c2ccccc2-c2ccccc21]

Into a 120 mL autoclave were added (9H-fluoren-9-yl)methyl 3-(2-methoxy-1-(phenylamino)ethylidene)-2-oxopyrrolidine-1-carboxylate (310.0 mg) [mw. 454.52, 0.682 mmol] and asymmetric hydrogenation catalyst [Rh(cod) (S,S)-skewphos)]OTf (10.9 mg) [mw. 800.65, 1.36*10⁻² mmol], and argon substitution was performed 7 times. Thereto was added dehydrated methanol (13 mL) by argon pressure supply, and the mixture was stirred for 10 min. Hydrogen pressure was raised to 5 MPa, and the mixture was stirred at 50° C. for 21 hr. The reaction mixture was allowed to cool to room temperature and depressurized. The reaction mixture was subjected to high performance liquid chromatography and area percentage of the resultant product, (9H-fluoren-9-yl)methyl 4-methoxymethyl-2,3,3a,4,5,9b-hexahydro-1H-pyrrolo[3,2-c]quinoline-1-carboxylate, was determined to find production at a ratio of 10%. High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min.

Reference Example 20

Synthesis of (3aR,4R,9bR)-tert-butyl 4-(methoxymethyl)-2,3,3a,4,5,9b-hexahydro-1H-pyrrolo[3,2-c]quinoline-1-carboxylate

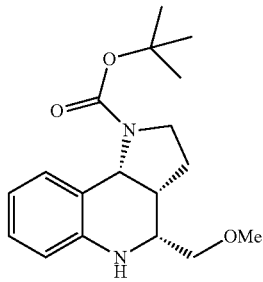 [SMILES: COC[C@@H]1Nc2ccccc2[C@H]2[C@@H]1CCN2C(=O)OC(C)(C)C]

Into a 120 mL stainless autoclave were charged tert-butyl 3-(2-methoxy-1-(phenylamino)ethylidene)-2-oxopyrrolidine-1-carboxylate (125.0 mg) [mw. 332.39, 0.376 mmol] and [Rh(cod) (S,S)-skewphos)]OTf (12.0 mg) [mw. 800.65, 0.015 mmol], and the system was substituted with argon. Deaeration-treated dehydrated methanol (5 mL) was added by argon pressure supply. Hydrogen was filled therein to 5 MPa, and the mixture was stirred at a reaction temperature of 50° C. for 16 hr. The reaction mixture was allowed to cool to room temperature and depressurized. The reaction mixture was subjected to high performance liquid chromatography and area percentage and optical purity of the resultant product, (3aR,4R,9bR)-tert-butyl 4-(methoxymethyl)-2,3,3a,4,5,9b-hexahydro-1H-pyrrolo[3,2-c]quinoline-1-carboxylate, were determined to find production at a ratio of 71%. The optical purity was 52% ee.

High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min.

Reference Example 21

Synthesis of (3aR,4R,9bR)-benzyl 4-(methoxymethyl)-2,3,3a,4,5,9b-hexahydro-1H-pyrrolo[3,2-c]quinoline-1-carboxylate

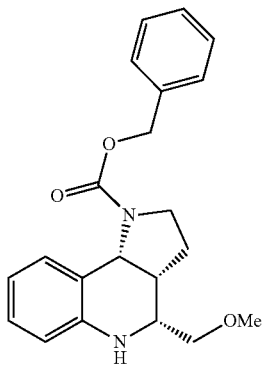 [SMILES: COC[C@@H]1Nc2ccccc2[C@H]2[C@@H]1CCN2C(=O)OCc1ccccc1]

Into a 120 mL stainless autoclave were charged benzyl 3-(2-methoxy-1-(phenylamino)ethylidene)-2-oxopyrrolidine-1-carboxylate (125.0 mg) [mw. 366.41, 0.341 mmol] and [Rh(cod) (S,S)-skewphos]OTf (10.9 mg) [mw. 800.65, 0.0136 mmol, s/c 25], and the system was substituted with argon. Deaeration-treated dehydrated acetone (5 mL) was added by argon pressure supply. Hydrogen was filled therein to 5 MPa, and the mixture was stirred at a reaction temperature of 50° C. for 16 hr. The reaction mixture was allowed to cool to room temperature and depressurized. The reaction mixture was subjected to high performance liquid chromatography and area percentage and optical purity of the resultant product, (3aR,4R,9bR)-benzyl 4-(methoxymethyl)-2,3,3a,4,5,9b-hexahydro-1H-pyrrolo[3,2-c]quinoline-1-carboxylate, were determined to find production at a ratio of 57%. The optical purity was 57% ee. High performance liquid chromatography analysis conditions: UV detector wavelength 220 nm, mobile phase 50 mmol/L aqueous potassium dihydrogen phosphate solution (adjusted to pH 7.0 with 10% aqueous sodium hydroxide solution)/acetonitrile for high-performance liquid chromatography=45/55, column YMC-Pack ODS-A A-302, measurement temperature 30° C., flow rate 1.0 mL/min. High performance liquid chromatography optical purity analysis conditions: UV detector wavelength 220 nm, mobile phase n-hexane for high performance liquid chromatography/2-propanol for high-performance liquid chromatography=9/1, column CHIRALPAK AD-H, measurement temperature 30° C., flow rate 1.0 mL/min, retention time 11.5 min ((3aS,4S,9bS)), retention time 12.6 min ((3aR,4R,9bR)).

Reference Example 22

(3aR,4R,9bR)-benzyl 4-(methoxymethyl)-2,3,3a,4,5,9b-hexahydro-1H-pyrrolo[3,2-c]quinoline-1-carboxylate

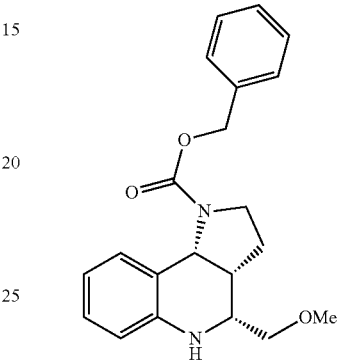

In the same manner as in Reference Example 21 except that methanol was used instead of acetone in the same manner as in Reference Example 21, benzyl 3-(2-methoxy-1-(phenylamino)ethylidene)-2-oxopyrrolidine-1-carboxylate was hydrogenated to give 57% ee. (3aR,4R,9bR)-benzyl 4-(methoxymethyl)-2,3,3a,4,5,9b-hexahydro-1H-pyrrolo[3,2-c]quinoline-1-carboxylate at a ratio of 62%.

Reference Example 23

(3aR,4R,9bR)-benzyl 4-(methoxymethyl)-2,3,3a,4,5,9b-hexahydro-1H-pyrrolo[3,2-c]quinoline-1-carboxylate

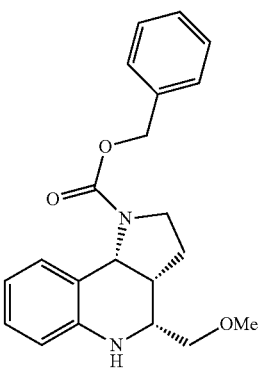 [SMILES: COC[C@@H]1Nc2ccccc2[C@H]2[C@@H]1CCN2C(=O)OCc1ccccc1]

In the same manner as in Reference Example 21 except that ethyl acetate was used instead of acetone in the same manner as in Reference Example 21, benzyl 3-(2-methoxy-1-(phenylamino)ethylidene)-2-oxopyrrolidine-1-carboxylate was hydrogenated to give 62% ee. (3aR,4R,9bR)-benzyl 4-(methoxymethyl)-2,3,3a,4,5,9b-hexahydro-1H-pyrrolo[3,2-c]quinoline-1-carboxylate at a ratio of 47%.

Reference Example 24

(3aR,4R,9bR)-benzyl 4-(methoxymethyl)-2,3,3a,4,5,9b-hexahydro-1H-pyrrolo[3,2-c]quinoline-1-carboxylate

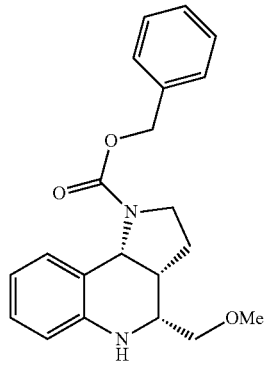 [SMILES: COC[C@@H]1Nc2ccccc2[C@H]2[C@@H]1CCN2C(=O)OCc1ccccc1]

In the same manner as in Reference Example 21 except that n-propanol was used instead of acetone in the same manner as in Reference Example 21, benzyl 3-(2-methoxy-1-(phenylamino)ethylidene)-2-oxopyrrolidine-1-carboxylate was hydrogenated to give 30% ee. (3aR,4R,9bR)-benzyl 4-(methoxymethyl)-2,3,3a,4,5,9b-hexahydro-1H-pyrrolo[3,2-c]quinoline-1-carboxylate at a ratio of 12%.

Reference Example 25

(3aR,4R,9bR)-benzyl 4-(methoxymethyl)-2,3,3a,4,5,9b-hexahydro-1H-pyrrolo[3,2-c]quinoline-1-carboxylate

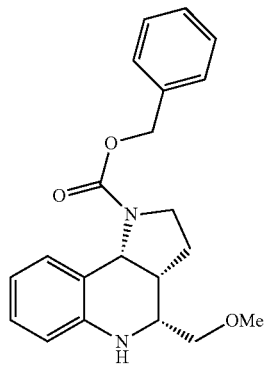 [SMILES: COC[C@@H]1Nc2ccccc2[C@H]2[C@@H]1CCN2C(=O)OCc1ccccc1]

In the same manner as in Reference Example 21 except that 2,2,2-trifluoroethanol was used instead of acetone in the same manner as in Reference Example 21, benzyl 3-(2-methoxy-1-(phenylamino)ethylidene)-2-oxopyrrolidine-1-carboxylate was hydrogenated to give 19% ee. (3aR,4R,9bR)-benzyl 4-(methoxymethyl)-2,3,3a,4,5,9b-hexahydro-1H-pyrrolo[3,2-c]quinoline-1-carboxylate at a ratio of 46%.

Reference Example 26

(3aR,4R,9bR)-benzyl 4-(methoxymethyl)-2,3,3a,4,5,9b-hexahydro-1H-pyrrolo[3,2-c]quinoline-1-carboxylate

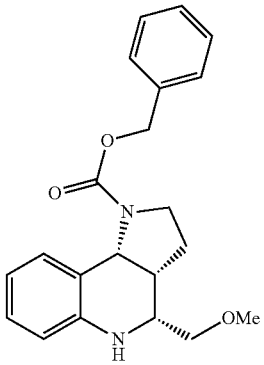 [SMILES: COC[C@@H]1Nc2ccccc2[C@H]2[C@@H]1CCN2C(=O)OCc1ccccc1]

In the same manner as in Reference Example 21 except that ethylene glycol was used instead of acetone in the same manner as in Reference Example 21, benzyl 3-(2-methoxy-1-(phenylamino)ethylidene)-2-oxopyrrolidine-1-carboxylate was hydrogenated to give 54% ee. (3aR,4R,9bR)-benzyl 4-(methoxymethyl)-2,3,3a,4,5,9b-hexahydro-1H-pyrrolo[3,2-c]quinoline-1-carboxylate at a ratio of 14%.

Reference Example 27

(3aR,4R,9bR)-benzyl 4-(methoxymethyl)-2,3,3a,4,5,9b-hexahydro-1H-pyrrolo[3,2-c]quinoline-1-carboxylate

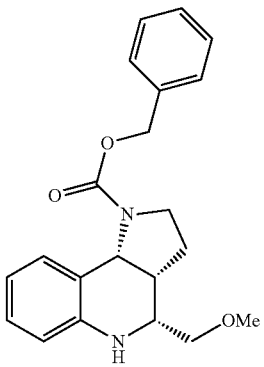 [SMILES: COC[C@@H]1Nc2ccccc2[C@H]2[C@@H]1CCN2C(=O)OCc1ccccc1]

In the same manner as in Reference Example 21 except that methylethylketone was used instead of acetone in the same manner as in Reference Example 21, benzyl 3-(2-methoxy-1-(phenylamino)ethylidene)-2-oxopyrrolidine-1-carboxylate was hydrogenated to give 50% ee. (3aR,4R,9bR)-benzyl- 4-(methoxymethyl)-2,3,3a,4,5,9b-hexahydro-1H-pyrrolo[3,2-c]quinoline-1-carboxylate at a ratio of 56%.

Reference Example 28

(3aR,4R,9bR)-benzyl 4-(methoxymethyl)-2,3,3a,4,5,9b-hexahydro-1H-pyrrolo[3,2-c]quinoline-1-carboxylate

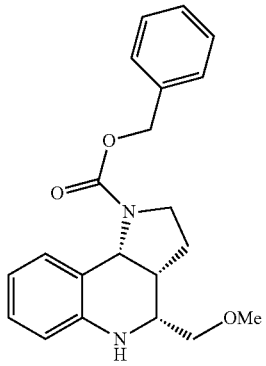 [SMILES: COC[C@@H]1Nc2ccccc2[C@H]2[C@@H]1CCN2C(=O)OCc1ccccc1]

In the same manner as in Reference Example 21 except that methylisobutylketone was used instead of acetone in the same manner as in Reference Example 21, benzyl 3-(2-methoxy-1-(phenylamino)ethylidene)-2-oxopyrrolidine-1-carboxylate was hydrogenated to give 50% ee. (3aR,4R,9bR)-benzyl 4-(methoxymethyl)-2,3,3a,4,5,9b-hexahydro-1H-pyrrolo[3,2-c]quinoline-1-carboxylate at a ratio of 48%.

Reference Example 29

(3aR,4R,9bR)-benzyl 4-(methoxymethyl)-2,3,3a,4,5,9b-hexahydro-1H-pyrrolo[3,2-c]quinoline-1-carboxylate

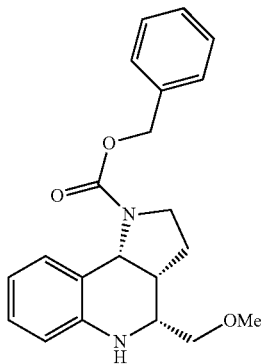 [SMILES: COC[C@@H]1Nc2ccccc2[C@H]2[C@@H]1CCN2C(=O)OCc1ccccc1]

In the same manner as in Reference Example 21 except that butyl acetate was used instead of acetone in the same manner as in Reference Example 21, benzyl 3-(2-methoxy-1-(phenylamino)ethylidene)-2-oxopyrrolidine-1-carboxylate was hydrogenated to give 52% ee. (3aR,4R,9bR)-benzyl 4-(methoxymethyl)-2,3,3a,4,5,9b-hexahydro-1H-pyrrolo[3,2-c]quinoline-1-carboxylate at a ratio of 8%.

Reference Example 30

Synthesis of (3aR,4R,9bR)-benzyl 4-(methoxymethyl)-2,3,3a,4,5,9b-hexahydro-1H-pyrrolo[3,2-c]quinoline-1-carboxylate

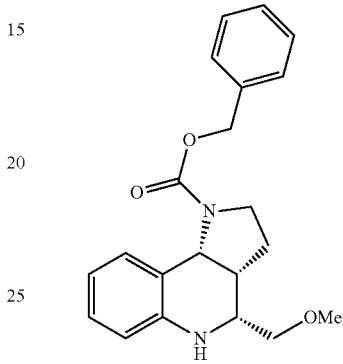

Into a 10 mL Schlenk flask were charged [Rh(cod)$_2$]OTf (2.6 mg) [mw. 468.34, 5.5 μmol, s/c 25] and (2S,4S)-skew-phos (2.9 mg) [mw. 440.50, 6.6 μmol], and the system was substituted with argon. Deaeration-treated dehydrated methanol (1 mL) was added by argon pressure supply. Under an argon atmosphere, the mixture was stirred at room temperature for 1 hr. Separately, into a 120 mL stainless autoclave was charged benzyl 3-(2-methoxy-1-(phenylamino)ethylidene)-2-oxopyrrolidine-1-carboxylate (50.0 mg) [mw. 366.41, 136 μmol], and the system was substituted with argon. The catalyst in the Schlenk flask was added into the autoclave by argon pressure supply. Furthermore, the inside of the Schlenk flask was washed with dehydrated methanol (4 mL), and the washing was added into the autoclave by argon pressure supply. Hydrogen was filled therein to 1 MPa, and the mixture was stirred at a reaction temperature of 50° C. for 16 hr. The reaction mixture was allowed to cool to room temperature and depressurized. The reaction mixture was subjected to high performance liquid chromatography and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined to find production at a ratio of 7%.

High performance liquid chromatography production rate analysis conditions: UV detector wavelength 220 nm, mobile phase 20 mmol/L aqueous dipotassium hydrogen phosphate solution/acetonitrile for high performance liquid chromatography=60/40, column CHIRALPAK AS-RH, measurement temperature 25° C., flow rate 1.0 mL/min, retention time 22.3 min. (this analysis method was used in Reference Examples 30-51) High performance liquid chromatography optical purity analysis conditions: UV detector wavelength 220 nm, mobile phase n-hexane for high performance liquid chromatography/2-propanol for high performance liquid chromatography=9/1, column CHIRALPAK AD-H, measurement temperature 25° C., flow rate 0.5 mL/min, retention time 29.9 min

Reference Example 31

Synthesis of (3aR,4R,9bR)-benzyl 4-(methoxymethyl)-2,3,3a,4,5,9b-hexahydro-1H-pyrrolo[3,2-c]quinoline-1-carboxylate

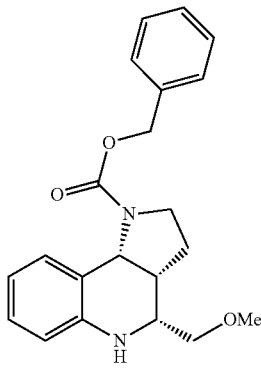 [SMILES: COC[C@@H]1Nc2ccccc2[C@H]2[C@@H]1CCN2C(=O)OCc1ccccc1]

In the same manner as in Reference Example 30 except that (R)-1-[(S)-2-(diphenylphosphino)ferrocenyl]ethyldicyclohexylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and the area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 8%.

Reference Example 32

Synthesis of (3aR,4R,9bR)-benzyl 4-(methoxymethyl)-2,3,3a,4,5,9b-hexahydro-1H-pyrrolo[3,2-c]quinoline-1-carboxylate

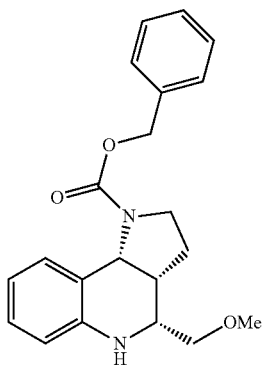 [SMILES: COC[C@@H]1Nc2ccccc2[C@H]2[C@@H]1CCN2C(=O)OCc1ccccc1]

In the same manner as in Reference Example 30 except that (R)-1-[(R)-2-(Diphenylphosphino) ferrocenyl]ethyldicyclohexylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 20%.

Reference Example 33

Synthesis of (3aR,4R,9bR)-benzyl 4-(methoxymethyl)-2,3,3a,4,5,9b-hexahydro-1H-pyrrolo[3,2-c]quinoline-1-carboxylate

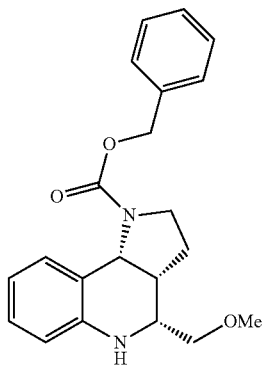 [SMILES: COC[C@@H]1Nc2ccccc2[C@H]2[C@@H]1CCN2C(=O)OCc1ccccc1]

In the same manner as in Reference Example 30 except that (R)-1-[(S)-2-diphenylphosphinoferrocenyl]ethyldi-tert-butylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography, (3aR,4R,9bR)-benzyl 4-(methoxymethyl)-2,3,3a,4,5,9b-hexahydro-1H-pyrrolo[3,2-c]quinoline-1-carboxylate, was determined to find production at an area percentage of 3%.

Reference Example 34

Synthesis of (3aR,4R,9bR)-benzyl 4-(methoxymethyl)-2,3,3a,4,5,9b-hexahydro-1H-pyrrolo[3,2-c]quinoline-1-carboxylate

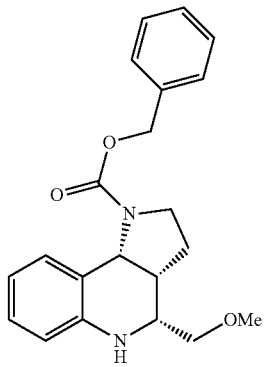 [SMILES: COC[C@@H]1Nc2ccccc2[C@H]2[C@@H]1CCN2C(=O)OCc1ccccc1]

In the same manner as in Reference Example 30 except that (R)-1-[[(S)-2-dicyclohexylphosphino]ferrocenyl]ethyldicyclohexylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 1%.

Reference Example 35

Synthesis of (3aR,4R,9bR)-benzyl 4-(methoxymethyl)-2,3,3a,4,5,9b-hexahydro-1H-pyrrolo[3,2-c]quinoline-1-carboxylate

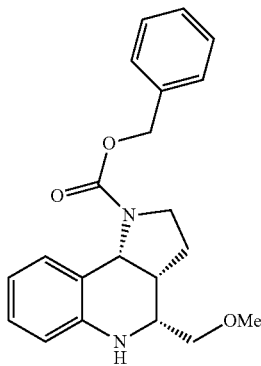 [SMILES: COC[C@@H]1Nc2ccccc2[C@H]2[C@@H]1CCN2C(=O)OCc1ccccc1]

In the same manner as in Reference Example 30 except that (R)-1-[[(S)-2-Diphenylphosphino]ferrocenyl]ethyldi-3,5-xylylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production of the resultant product at not more than 1%.

Reference Example 36

Synthesis of (3aR,4R,9bR)-benzyl 4-(methoxymethyl)-2,3,3a,4,5,9b-hexahydro-1H-pyrrolo[3,2-c]quinoline-1-carboxylate

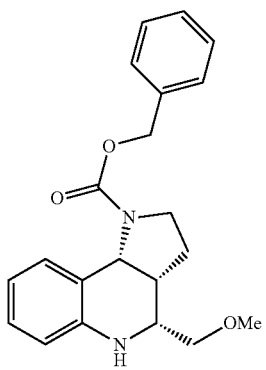 [SMILES: COC[C@@H]1Nc2ccccc2[C@H]2[C@@H]1CCN2C(=O)OCc1ccccc1]

In the same manner as in Reference Example 30 except that (R)-1-[[(S)-2-Di-(3,5-bis(trifluoromethyl)phenyl)phosphino]ferrocenyl]ethyldicyclohexylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production of the resultant product at not more than 1%.

Reference Example 37

Synthesis of (3aR,4R,9bR)-benzyl 4-(methoxymethyl)-2,3,3a,4,5,9b-hexahydro-1H-pyrrolo[3,2-c]quinoline-1-carboxylate

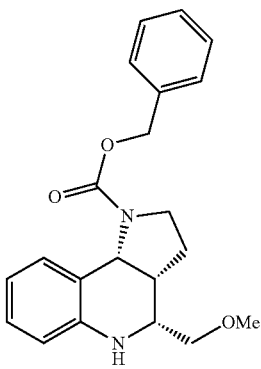 [SMILES: COC[C@@H]1Nc2ccccc2[C@H]2[C@@H]1CCN2C(=O)OCc1ccccc1]

Into a 10 mL Schlenk flask were charged [Rh(cod)$_2$]OTf (2.6 mg) [mw. 468.34, 5.5 µmol, s/c 25] and (2S,4S)-skewphos (2.9 mg) [mw. 440.50, 6.6 µmol], and the system was substituted with argon. Deaeration-treated dehydrated methanol (1 mL) was added by argon pressure supply. Under an argon atmosphere, the mixture was stirred at room temperature for 1 hr. Separately, into a 120 mL stainless autoclave was charged benzyl 3-(2-methoxy-1-(phenylamino)ethylidene)-2-oxopyrrolidine-1-carboxylate (50.0 mg) [mw. 366.41, 136 µmol], and the system was substituted with argon. The catalyst in the Schlenk flask was added into the autoclave by argon pressure supply. Furthermore, the inside of the Schlenk flask was washed with dehydrated methanol (4 mL), and the washing was added into the autoclave by argon pressure supply. Hydrogen was filled therein to 5 MPa, and the mixture was stirred at a reaction temperature of 50° C. for 16 hr. The reaction mixture was allowed to cool to room temperature and depressurized. The area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at a ratio of 49%. The optical purity was 60% ee.

Reference Example 38

Synthesis of (3aR,4R,9bR)-benzyl 4-(methoxymethyl)-2,3,3a,4,5,9b-hexahydro-1H-pyrrolo[3,2-c]quinoline-1-carboxylate

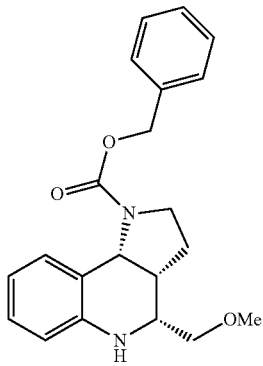 [SMILES: COC[C@@H]1Nc2ccccc2[C@H]2[C@@H]1CCN2C(=O)OCc1ccccc1]

In the same manner as in Reference Example 37 except that dehydrating acetonitrile was used as a solvent instead of dehydrated methanol, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production of the resultant product at not more than 1%.

Reference Example 39

Synthesis of (3aR,4R,9bR)-benzyl 4-(methoxymethyl)-2,3,3a,4,5,9b-hexahydro-1H-pyrrolo[3,2-c]quinoline-1-carboxylate

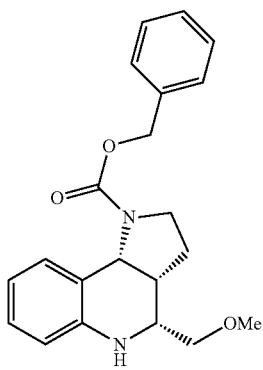 [SMILES: COC[C@@H]1Nc2ccccc2[C@H]2[C@@H]1CCN2C(=O)OCc1ccccc1]

In the same manner as in Reference Example 37 except that dehydrated 2-propanol was used as a solvent instead of dehydrated methanol, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 26%. The optical purity was 60% ee.

Reference Example 40

Synthesis of (3aR,4R,9bR)-benzyl 4-(methoxymethyl)-2,3,3a,4,5,9b-hexahydro-1H-pyrrolo[3,2-c]quinoline-1-carboxylate

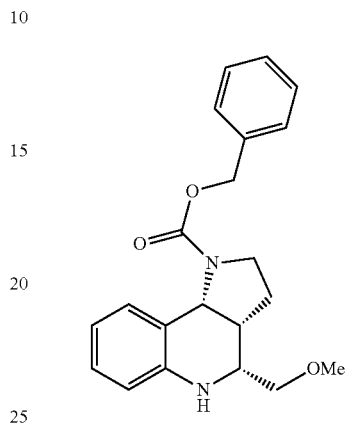

In the same manner as in Reference Example 37 except that dehydrated tetrahydrofuran was used as a solvent instead of dehydrated methanol, 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-s c]quinoline-1-carboxylate, was determined by high performance liquid chromatography to find production at an area percentage of 49%. The optical purity was 64% ee.

Reference Example 41

Synthesis of (3aR,4R,9bR)-benzyl 4-(methoxymethyl)-2,3,3a,4,5,9b-hexahydro-1H-pyrrolo[3,2-c]quinoline-1-carboxylate

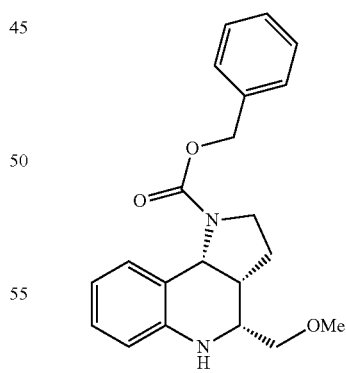

In the same manner as in Reference Example 37 except that (R)-1-[(S)-2-(Diphenylphosphino)ferrocenyl]ethyldicyclohexylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 25%.

Reference Example 42

Synthesis of (3aR,4R,9bR)-benzyl 4-(methoxymethyl)-2,3,3a,4,5,9b-hexahydro-1H-pyrrolo[3,2-c]quinoline-1-carboxylate

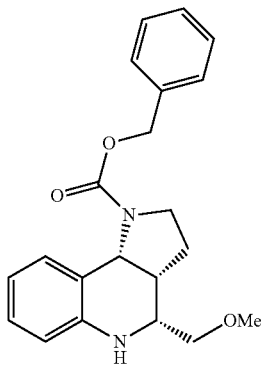 [SMILES: COC[C@@H]1Nc2ccccc2[C@H]2[C@@H]1CCN2C(=O)OCc1ccccc1]

In the same manner as in Reference Example 37 except that (R)-1-[(S)-2-diphenylphosphinoferrocenyl]ethyldi-tert-butylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 4%.

Reference Example 43

Synthesis of (3aR,4R,9bR)-benzyl 4-(methoxymethyl)-2,3,3a,4,5,9b-hexahydro-1H-pyrrolo[3,2-c]quinoline-1-carboxylate

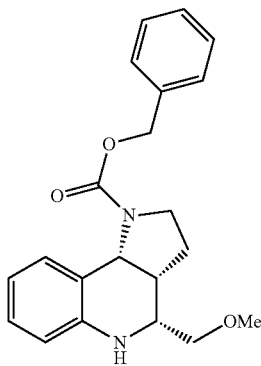 [SMILES: COC[C@@H]1Nc2ccccc2[C@H]2[C@@H]1CCN2C(=O)OCc1ccccc1]

In the same manner as in Reference Example 37 except that (S)-1-[(R)-2-Diphenylphosphinoferrocenyl]ethyldi-tert-butylphosphine was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 3%.

Reference Example 44

Synthesis of (3aR,4R,9bR)-benzyl 4-(methoxymethyl)-2,3,3a,4,5,9b-hexahydro-1H-pyrrolo[3,2-c]quinoline-1-carboxylate

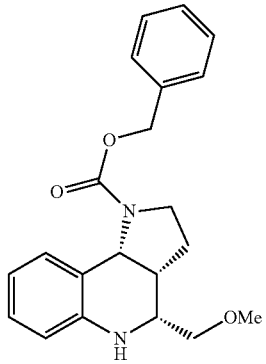 [SMILES: COC[C@@H]1Nc2ccccc2[C@H]2[C@@H]1CCN2C(=O)OCc1ccccc1]

In the same manner as in Reference Example 37 except that (2R,4R)-3,5-xylyl-skewphos was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aS,4S,9bS)-benzyl 4-(methoxymethyl)-2,3,3a,4,5,9b-hexahydro-1H-pyrrolo[3,2-c]quinoline-1-carboxylate, was determined by high performance liquid chromatography to find production at an area percentage of 48%.

Reference Example 45

Synthesis of (3aR,4R,9bR)-benzyl 4-(methoxymethyl)-2,3,3a,4,5,9b-hexahydro-1H-pyrrolo[3,2-c]quinoline-1-carboxylate

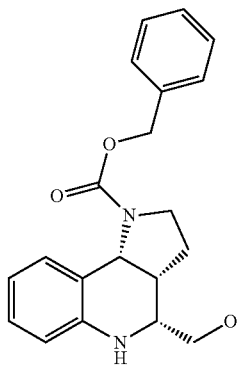

In the same manner as in Reference Example 37 except that (2R,4R)-ptbp-skewphos was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aS,4S,9bS)-benzyl 4-(methoxymethyl)-2,3,3a,4,5,9b-hexahydro-1H-pyrrolo[3,2-c]quinoline-1-carboxylate, was

Reference Example 46

Synthesis of (3aR,4R,9bR)-benzyl 4-(methoxymethyl)-2,3,3a,4,5,9b-hexahydro-1H-pyrrolo[3,2-c]quinoline-1-carboxylate

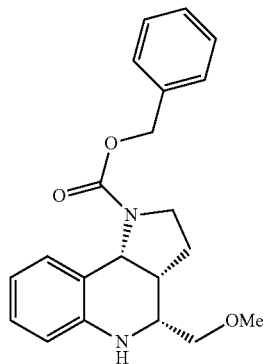 [SMILES: COC[C@@H]1Nc2ccccc2[C@H]2[C@@H]1CCN2C(=O)OCc1ccccc1]

In the same manner as in Reference Example 37 except that (S)-BINAP was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production of the resultant product at not more than 1%.

Reference Example 47

Synthesis of (3aR,4R,9bR)-benzyl 4-(methoxymethyl)-2,3,3a,4,5,9b-hexahydro-1H-pyrrolo[3,2-c]quinoline-1-carboxylate

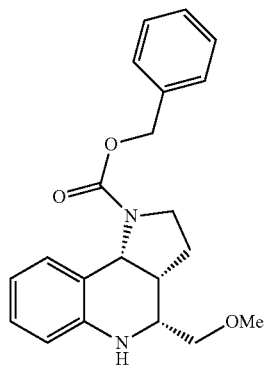 [SMILES: COC[C@@H]1Nc2ccccc2[C@H]2[C@@H]1CCN2C(=O)OCc1ccccc1]

In the same manner as in Reference Example 37 except that (S)-2,2'-bis(bis(4-chlorophenyl)phosphino)-1,1'-binaphthalene was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production of the resultant product at not more than 1%.

Reference Example 48

Synthesis of (3aR,4R,9bR)-benzyl 4-(methoxymethyl)-2,3,3a,4,5,9b-hexahydro-1H-pyrrolo[3,2-c]quinoline-1-carboxylate

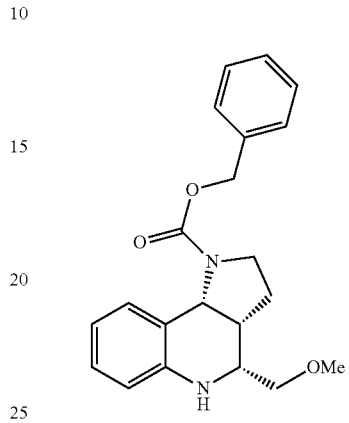

In the same manner as in Reference Example 37 except that (S)-2,2'-bis(bis(4-methoxyphenyl)phosphino)-1,1'-binaphthalene was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production of the resultant product at not more than 1%.

Reference Example 49

Synthesis of (3aR,4R,9bR)-benzyl 4-(methoxymethyl)-2,3,3a,4,5,9b-hexahydro-1H-pyrrolo[3,2-c]quinoline-1-carboxylate

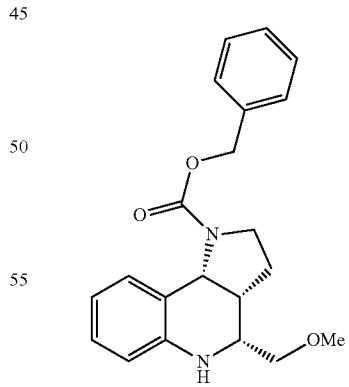

In the same manner as in Reference Example 37 except that 1,2-bis((2S,5S)-2,5-dimethylphospholan-1-yl)benzene was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product was determined by high performance liquid chromatography under optical purity analysis conditions to find a total value of the object products, (3aR,4R,9bR)-benzyl 4-(methoxymethyl)-2,3,3a,4,5,9b-hexahydro-1H-pyrrolo[3,2-c]quinoline-1-carboxylate and (3aS,4S,9bS)-benzyl 4-(methoxymethyl)-2,3,3a,4,5,9b-hexahydro-1H-pyrrolo[3,2-c]quinoline-1-carboxylate, of 16%.

Reference Example 50

Synthesis of (3aR,4R,9bR)-benzyl 4-(methoxymethyl)-2,3,3a,4,5,9b-hexahydro-1H-pyrrolo[3,2-c]quinoline-1-carboxylate

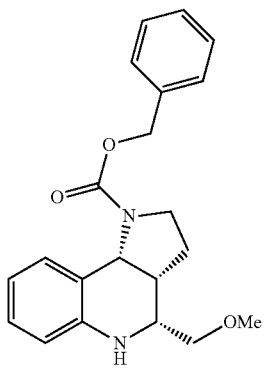 [SMILES: COC[C@@H]1Nc2ccccc2[C@H]2[C@@H]1CCN2C(=O)OCc1ccccc1]

In the same manner as in Reference Example 37 except that 1,2-bis((2S,5S)-2,5-diethylphospholan-1-yl)benzene was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product was determined by high performance liquid chromatography under optical purity analysis conditions to find a total value of the object products, (3aR,4R,9bR)-benzyl 4-(methoxymethyl)-2,3,3a,4,5,9b-hexahydro-1H-pyrrolo[3,2-c]quinoline-1-carboxylate and (3aS,4S,9bS)-benzyl 4-(methoxymethyl)-2,3,3a,4,5,9b-hexahydro-1H-pyrrolo[3,2-c]quinoline-1-carboxylate, of 26%.

Reference Example 51

Synthesis of (3aR,4R,9bR)-benzyl 4-(methoxymethyl)-2,3,3a,4,5,9b-hexahydro-1H-pyrrolo[3,2-c]quinoline-1-carboxylate

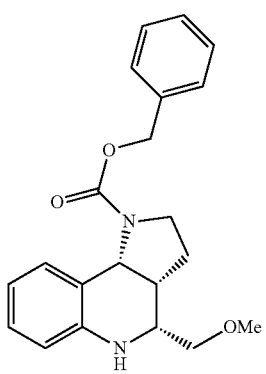 [SMILES: COC[C@@H]1Nc2ccccc2[C@H]2[C@@H]1CCN2C(=O)OCc1ccccc1]

In the same manner as in Reference Example 37 except that 1,2-bis((2R,5R)-2,5-diisopropylphospholan-1-yl)benzene was used as an asymmetric ligand instead of (2S,4S)-skewphos, benzyl 3-(2-methoxy-1-(phenylamino)ethylidene)-2-oxopyrrolidine-1-carboxylate was hydrogenated, and area percentage of the resultant product was determined by high performance liquid chromatography under optical purity analysis conditions to find a total value of the object products, (3aR,4R,9bR)-benzyl 4-(methoxymethyl)-2,3,3a,4,5,9b-hexahydro-1H-pyrrolo[3,2-c]quinoline-1-carboxylate and (3aS,4S,9bS)-benzyl 4-(methoxymethyl)-2,3,3a,4,5,9b-hexahydro-1H-pyrrolo[3,2-c]quinoline-1-carboxylate, of 13%.

Example 10

(3aR,4R,9bR)-benzyl 4-(methoxymethyl)-2,3,3a,4,5,9b-hexahydro-1H-pyrrolo[3,2-c]quinoline-1-carboxylate

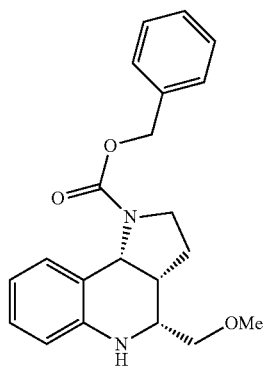 [SMILES: COC[C@@H]1Nc2ccccc2[C@H]2[C@@H]1CCN2C(=O)OCc1ccccc1]

In the same manner as in Reference Example 21 except that 0.1 equivalent of phenol was added to benzyl 3-(2-methoxy-1-(phenylamino)ethylidene)-2-oxopyrrolidine-1-carboxylate during charging, benzyl 3-(2-methoxy-1-(phenylamino)ethylidene)-2-oxopyrrolidine-1-carboxylate was hydrogenated to give 59% ee. (3aR,4R,9bR)-benzyl 4-(methoxymethyl)-2,3,3a,4,5,9b-hexahydro-1H-pyrrolo[3,2-c]quinoline-1-carboxylate at a ratio of 68%.

Example 11

(3aR,4R,9bR)-benzyl 4-(methoxymethyl)-2,3,3a,4,5,9b-hexahydro-1H-pyrrolo[3,2-c]quinoline-1-carboxylate

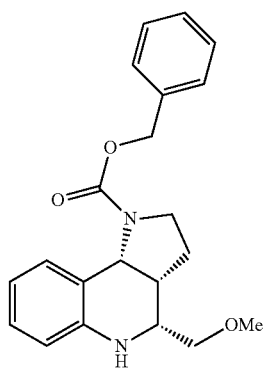 [SMILES: COC[C@@H]1Nc2ccccc2[C@H]2[C@@H]1CCN2C(=O)OCc1ccccc1]

In the same manner as in Reference Example 21 except that 0.1 equivalent of (R)-BINOL was added during charging, benzyl 3-(2-methoxy-1-(phenylamino)ethylidene)-2-oxopyrrolidine-1-carboxylate was hydrogenated to give 58% ee. (3aR,4R,9bR)-benzyl 4-(methoxymethyl)-2,3,3a,4,5,9b-hexahydro-1H-pyrrolo[3,2-c]quinoline-1-carboxylate at a ratio of 64%.

Example 12

(3aR,4R,9bR)-benzyl 4-(methoxymethyl)-2,3,3a,4,5,9b-hexahydro-1H-pyrrolo[3,2-c]quinoline-1-carboxylate

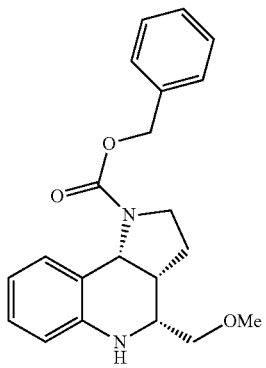 [SMILES: COC[C@@H]1Nc2ccccc2[C@H]2[C@@H]1CCN2C(=O)OCc1ccccc1]

In the same manner as in Reference Example 21 except that 0.1 equivalent of parabromophenol was added during charging, benzyl 3-(2-methoxy-1-(phenylamino)ethylidene)-2-oxopyrrolidine-1-carboxylate was hydrogenated to give 59% ee. (3aR,4R,9bR)-benzyl 4-(methoxymethyl)-2,3,3a,4,5,9b-hexahydro-1H-pyrrolo[3,2-c]quinoline-1-carboxylate at a ratio of 63%.

Example 13

(3aR,4R,9bR)-benzyl 4-(methoxymethyl)-2,3,3a,4,5,9b-hexahydro-1H-pyrrolo[3,2-c]quinoline-1-carboxylate

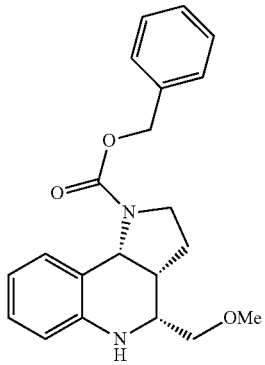 [SMILES: COC[C@@H]1Nc2ccccc2[C@H]2[C@@H]1CCN2C(=O)OCc1ccccc1]

In the same manner as in Reference Example 21 except that 0.1 equivalent of 4-benzylphenol was added during charging, benzyl 3-(2-methoxy-1-(phenylamino)ethylidene)-2-oxopyrrolidine-1-carboxylate was hydrogenated to give 58% ee. (3aR,4R,9bR)-benzyl-4-(methoxymethyl)-2,3,3a,4,5,9b-hexahydro-1H-pyrrolo[3,2-c]quinoline-1-carboxylate at a ratio of 72%.

Example 14

(3aR,4R,9bR)-benzyl 4-(methoxymethyl)-2,3,3a,4,5,9b-hexahydro-1H-pyrrolo[3,2-c]quinoline-1-carboxylate

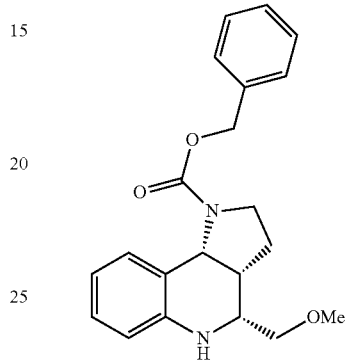

In the same manner as in Reference Example 21 except that 0.1 equivalent of parahydroxybenzophenone was added during charging, benzyl 3-(2-methoxy-1-(phenylamino)ethylidene)-2-oxopyrrolidine-1-carboxylate was hydrogenated to give 57% ee. (3aR,4R,9bR)-benzyl 4-(methoxymethyl)-2,3,3a,4,5,9b-hexahydro-1H-pyrrolo[3,2-c]quinoline-1-carboxylate at a ratio of 76%.

Example 15

(3aR,4R,9bR)-benzyl 4-(methoxymethyl)-2,3,3a,4,5,9b-hexahydro-1H-pyrrolo[3,2-c]quinoline-1-carboxylate

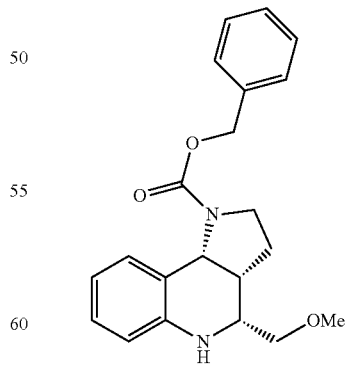

In the same manner as in Reference Example 21 except that 0.1 equivalent of p-methoxyphenol was added during charging, benzyl 3-(2-methoxy-1-(phenylamino)ethylidene)-2-oxopyrrolidine-1-carboxylate was hydrogenated to give 59% ee. (3aR,4R,9bR)-benzyl 4-(methoxymethyl)-2,3,3a,4,5,9b-hexahydro-1H-pyrrolo[3,2-c]quinoline-1-carboxylate at a ratio of 59%.

Example 16

(3aR,4R,9bR)-benzyl 4-(methoxymethyl)-2,3,3a,4,5,9b-hexahydro-1H-pyrrolo[3,2-c]quinoline-1-carboxylate

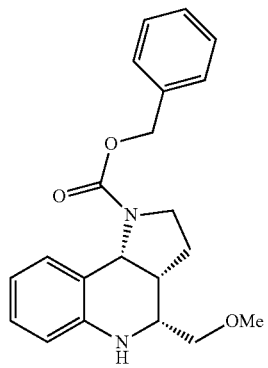 [SMILES: COC[C@@H]1Nc2ccccc2[C@H]2[C@@H]1CCN2C(=O)OCc1ccccc1]

In the same manner as in Reference Example 21 except that 0.1 equivalent of catechol was added during charging, benzyl 3-(2-methoxy-1-(phenylamino)ethylidene)-2-oxopyrrolidine-1-carboxylate was hydrogenated to give 59% ee. (3aR,4R,9bR)-benzyl 4-(methoxymethyl)-2,3,3a,4,5,9b-hexahydro-1H-pyrrolo[3,2-c]quinoline-1-carboxylate at a ratio of 66%.

Example 17

(3aR,4R,9bR)-benzyl 4-(methoxymethyl)-2,3,3a,4,5,9b-hexahydro-1H-pyrrolo[3,2-c]quinoline-1-carboxylate

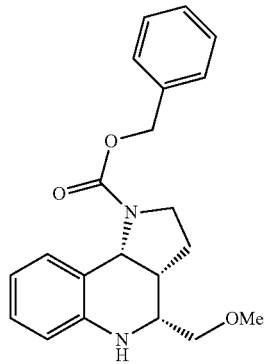 [SMILES: COC[C@@H]1Nc2ccccc2[C@H]2[C@@H]1CCN2C(=O)OCc1ccccc1]

In the same manner as in Reference Example 21 except that 0.1 equivalent of resorcinol was added during charging, benzyl 3-(2-methoxy-1-(phenylamino)ethylidene)-2-oxopyrrolidine-1-carboxylate was hydrogenated to give 59% ee. (3aR, 4R,9bR)-benzyl 4-(methoxymethyl)-2,3,3a,4,5,9b-hexahydro-1H-pyrrolo[3,2-c]quinoline-1-carboxylate at a ratio of 67%.

Example 18

(3aR,4R,9bR)-benzyl 4-(methoxymethyl)-2,3,3a,4,5,9b-hexahydro-1H-pyrrolo[3,2-c]quinoline-1-carboxylate

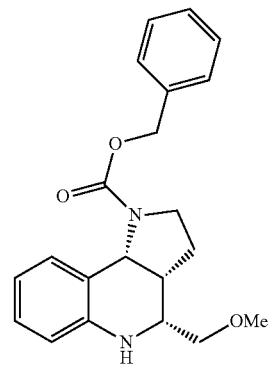 [SMILES: COC[C@@H]1Nc2ccccc2[C@H]2[C@@H]1CCN2C(=O)OCc1ccccc1]

In the same manner as in Reference Example 21 except that 0.1 equivalent of hydroquinone was added during charging, benzyl 3-(2-methoxy-1-(phenylamino)ethylidene)-2-oxopyrrolidine-1-carboxylate was hydrogenated to give 59% ee. (3aR,4R,9bR)-benzyl 4-(methoxymethyl)-2,3,3a,4,5,9b-hexahydro-1H-pyrrolo[3,2-c]quinoline-1-carboxylate at a ratio of 68%.

Example 19

(3aR,4R,9bR)-benzyl 4-(methoxymethyl)-2,3,3a,4,5,9b-hexahydro-1H-pyrrolo[3,2-c]quinoline-1-carboxylate

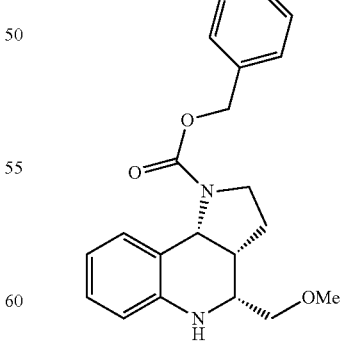

In the same manner as in Reference Example 21 except that 0.1 equivalent of phloroglucinol was added during charging, benzyl 3-(2-methoxy-1-(phenylamino)ethylidene)-2-oxopyrrolidine-1-carboxylate was hydrogenated to give 58% ee.

Example 20

(3aR,4R,9bR)-benzyl 4-(methoxymethyl)-2,3,3a,4,5, 9b-hexahydro-1H-pyrrolo[3,2-c]quinoline-1-carboxylate

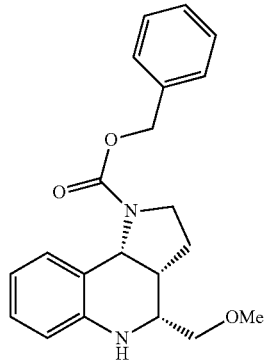 [SMILES: COC[C@@H]1Nc2ccccc2[C@H]2[C@@H]1CCN2C(=O)OCc1ccccc1]

In the same manner as in Reference Example 21 except that 0.1 equivalent of cyanuric acid was added during charging, benzyl 3-(2-methoxy-1-(phenylamino)ethylidene)-2-oxopyrrolidine-1-carboxylate was hydrogenated to give 64% ee. (3aR,4R,9bR)-benzyl 4-(methoxymethyl)-2,3,3a,4,5,9b-hexahydro-1H-pyrrolo[3,2-c]quinoline-1-carboxylate at a ratio of 77%.

Example 21

(3aR,4R,9bR)-benzyl 4-(methoxymethyl)-2,3,3a,4,5, 9b-hexahydro-1H-pyrrolo[3,2-c]quinoline-1-carboxylate

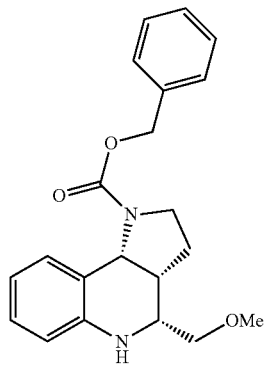 [SMILES: COC[C@@H]1Nc2ccccc2[C@H]2[C@@H]1CCN2C(=O)OCc1ccccc1]

In the same manner as in Reference Example 21 except that 0.1 equivalent of 2-methoxyphenol was added during charging, benzyl 3-(2-methoxy-1-(phenylamino)ethylidene)-2-oxopyrrolidine-1-carboxylate was hydrogenated to give 56% ee. (3aR,4R,9bR)-benzyl 4-(methoxymethyl)-2,3,3a,4,5,9b-hexahydro-1H-pyrrolo[3,2-c]quinoline-1-carboxylate at a ratio of 71%.

Example 22

(3aR,4R,9bR)-benzyl 4-(methoxymethyl)-2,3,3a,4,5, 9b-hexahydro-1H-pyrrolo[3,2-c]quinoline-1-carboxylate

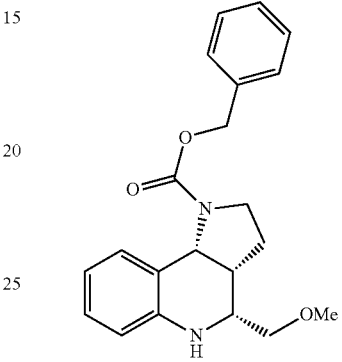

In the same manner as in Reference Example 21 except that 0.1 equivalent of 3-methoxyphenol was added during charging, benzyl 3-(2-methoxy-1-(phenylamino)ethylidene)-2-oxopyrrolidine-1-carboxylate was hydrogenated to give 57% ee. (3aR,4R,9bR)-benzyl 4-(methoxymethyl)-2,3,3a,4,5,9b-hexahydro-1H-pyrrolo[3,2-c]quinoline-1-carboxylate at a ratio of 75%.

Example 23

(3aR,4R,9bR)-benzyl 4-(methoxymethyl)-2,3,3a,4,5, 9b-hexahydro-1H-pyrrolo[3,2-c]quinoline-1-carboxylate

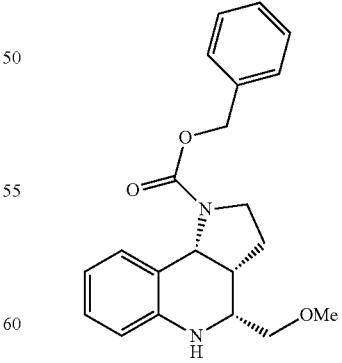

In the same manner as in Reference Example 21 except that 0.1 equivalent of 4-ethyl-2-methoxyphenol was added during charging, benzyl 3-(2-methoxy-1-(phenylamino)ethylidene)-2-oxopyrrolidine-1-carboxylate was hydrogenated to give 56% ee. (3aR,4R,9bR)-benzyl 4-(methoxymethyl)-2,3,3a,4,5,9b-hexahydro-1H-pyrrolo[3,2-c]quinoline-1-carboxylate at a ratio of 72%.

Example 24

(3aR,4R,9bR)-benzyl 4-(methoxymethyl)-2,3,3a,4,5,9b-hexahydro-1H-pyrrolo[3,2-c]quinoline-1-carboxylate

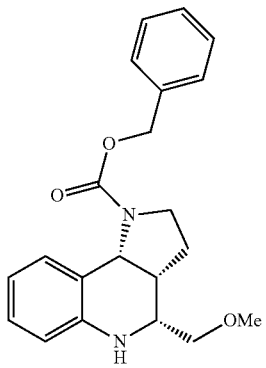 [SMILES: COC[C@@H]1Nc2ccccc2[C@H]2[C@@H]1CCN2C(=O)OCc1ccccc1]

In the same manner as in Reference Example 21 except that 0.1 equivalent of 2-benzylphenol was added during charging, benzyl 3-(2-methoxy-1-(phenylamino)ethylidene)-2-oxopyrrolidine-1-carboxylate was hydrogenated to give 57% ee. (3aR,4R,9bR)-benzyl 4-(methoxymethyl)-2,3,3a,4,5,9b-hexahydro-1H-pyrrolo[3,2-c]quinoline-1-carboxylate at a ratio of 71%.

Example 25

(3aR,4R,9bR)-benzyl 4-(methoxymethyl)-2,3,3a,4,5,9b-hexahydro-1H-pyrrolo[3,2-c]quinoline-1-carboxylate

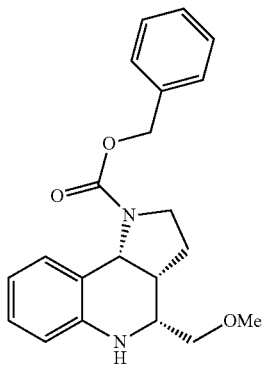 [SMILES: COC[C@@H]1Nc2ccccc2[C@H]2[C@@H]1CCN2C(=O)OCc1ccccc1]

In the same manner as in Reference Example 21 except that 0.1 equivalent of benzhydrol was added during charging, benzyl 3-(2-methoxy-(phenylamino)ethylidene)-2-oxopyrrolidine-1-carboxylate was hydrogenated to give 56% ee. (3aR,4R,9bR)-benzyl 4-(methoxymethyl)-2,3,3a,4,5,9b-hexahydro-1H-pyrrolo[3,2-c]quinoline-1-carboxylate at a ratio of 70%.

Example 26

(3aR,4R,9bR)-benzyl 4-(methoxymethyl)-2,3,3a,4,5,9b-hexahydro-1H-pyrrolo[3,2-c]quinoline-1-carboxylate

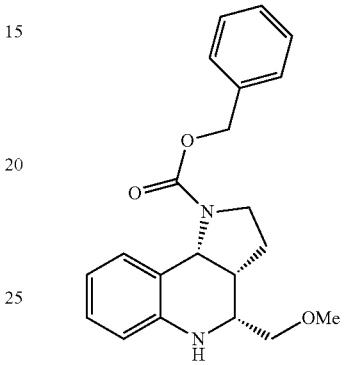

In the same manner as in Reference Example 21 except that 0.1 equivalent of salicyl alcohol was added during charging, benzyl 3-(2-methoxy-1-(phenylamino)ethylidene)-2-oxopyrrolidine-1-carboxylate was hydrogenated to give 58% ee. (3aR,4R,9bR)-benzyl 4-(methoxymethyl)-2,3,3a,4,5,9b-hexahydro-1H-pyrrolo[3,2-c]quinoline-1-carboxylate at a ratio of 74%.

Example 27

(3aR,4R,9bR)-benzyl 4-(methoxymethyl)-2,3,3a,4,5,9b-hexahydro-1H-pyrrolo[3,2-c]quinoline-1-carboxylate

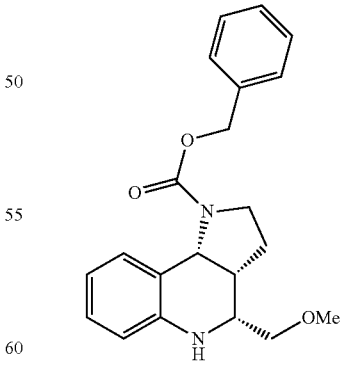

In the same manner as in Reference Example 21 except that 1 equivalent of cyanuric acid was added during charging and the catalytic amount was reduced to half (s/c 50), benzyl 3-(2-methoxy-1-(phenylamino)ethylidene)-2-oxopyrrolidine-1-carboxylate was hydrogenated to give 59% ee. (3aR, 4R,9bR)-benzyl 4-(methoxymethyl)-2,3,3a,4,5,9b-hexahydro-1H-pyrrolo[3,2-c]quinoline-1-carboxylate at a ratio of 56%.

Example 28

(3aR,4R,9bR)-benzyl 4-(methoxymethyl)-2,3,3a,4,5,9b-hexahydro-1H-pyrrolo[3,2-c]quinoline-1-carboxylate

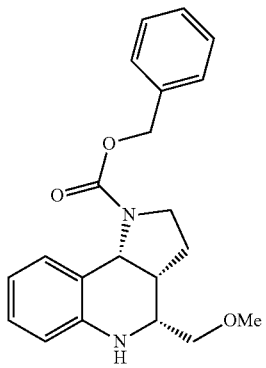 [SMILES: COC[C@@H]1Nc2ccccc2[C@H]2[C@@H]1CCN2C(=O)OCc1ccccc1]

In the same manner as in Reference Example 21 except that 1 equivalent of cyanuric acid and 3 equivalents of 2,2-dimethoxypropane were added during charging and the catalytic amount was reduced to half (s/c 50), benzyl 3-(2-methoxy-1-(phenylamino)ethylidene)-2-oxopyrrolidine-1-carboxylate was hydrogenated to give 58% ee. (3aR,4R,9bR)-benzyl 4-(methoxymethyl)-2,3,3a,4,5,9b-hexahydro-1H-pyrrolo[3,2-c]quinoline-1-carboxylate at a ratio of 74%.

Example 29

(3aR,4R,9bR)-benzyl 4-(methoxymethyl)-2,3,3a,4,5,9b-hexahydro-1H-pyrrolo[3,2-c]quinoline-1-carboxylate

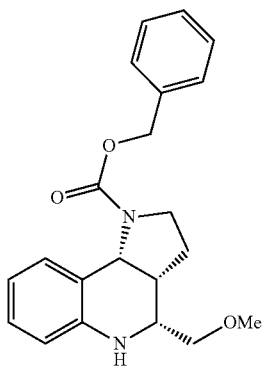 [SMILES: COC[C@@H]1Nc2ccccc2[C@H]2[C@@H]1CCN2C(=O)OCc1ccccc1]

In the same manner as in Reference Example 21 except that 1 equivalent of cyanuric acid and 3 equivalents of 2,2-diethoxypropane were added during charging and the catalytic amount was reduced to half (s/c 50), benzyl 3-(2-methoxy-1-(phenylamino)ethylidene)-2-oxopyrrolidine-1-carboxylate was hydrogenated to give 59% ee. (3aR,4R,9bR)-benzyl 4-(methoxymethyl)-2,3,3a,4,5,9b-hexahydro-1H-pyrrolo[3,2-c]quinoline-1-carboxylate at a ratio of 61%.

Example 30

(3aR,4R,9bR)-benzyl 4-(methoxymethyl)-2,3,3a,4,5,9b-hexahydro-1H-pyrrolo[3,2-c]quinoline-1-carboxylate

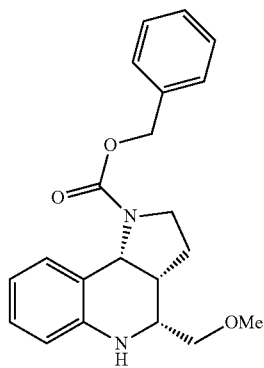 [SMILES: COC[C@@H]1Nc2ccccc2[C@H]2[C@@H]1CCN2C(=O)OCc1ccccc1]

Into a 120 mL stainless autoclave were charged benzyl 3-(2-methoxy-1-(phenylamino)ethylidene)-2-oxopyrrolidine-1-carboxylate (250.0 mg) [mw. 366.41, 0.682 mmol], [Rh(cod) (S,S)-skewphos)]OTf (10.9 mg) [mw. 800.65, 0.0136 mmol, s/c 25] and cyanuric acid (88.0 mg) [mw. 129.08, 0.682 mmol], and the system was substituted with argon. 2,2-Dimethoxypropane (244 µL) and deaeration-treated dehydrated acetone (10 mL) were added by argon pressure supply. Hydrogen was filled therein to 6 MPa, reaction temperature of 60° C. for 16 hr was stirred. The reaction mixture was allowed to cool to room temperature and depressurized. The reaction mixture was subjected to high performance liquid chromatography and area percentage and optical purity of the resultant product, (3aR,4R,9bR)-benzyl 4-(methoxymethyl)-2,3,3a,4,5,9b-hexahydro-1H-pyrrolo[3,2-c]quinoline-1-carboxylate, were determined to find production at a ratio of 74%. The optical purity was 58% ee.

Example 31

(3aR,4R,9bR)-benzyl 4-(methoxymethyl)-2,3,3a,4,5,9b-hexahydro-1H-pyrrolo[3,2-c]quinoline-1-carboxylate

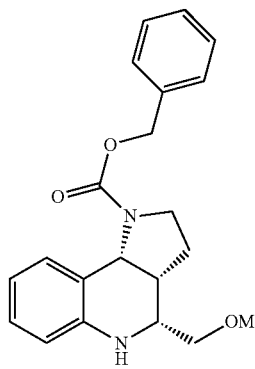

Into a 20 mL Schlenk flask were charged [Rh(cod)₂]OTf (6.4 mg) [mw. 468.34, 0.0136 mmol, s/c 50] and (2S,4S)-3,5-xylyl-skewphos (9.0 mg) [mw. 552.71, 0.0163 mmol], and the system was substituted with argon. Deaeration-treated dehydrated acetone (5 mL) was added by argon pressure supply. Under an argon atmosphere, the mixture was stirred at room temperature for 1 hr. Separately, into a 120 mL stainless autoclave were charged benzyl 3-(2-methoxy-1-(phenylamino)ethylidene)-2-oxopyrrolidine-1-carboxylate (250.0 mg) [mw. 366.41, 0.682 mmol] and cyanuric acid (88.0 mg) [mw. 129.08, 0.682 mmol], and the system was substituted with argon. The catalyst in the Schlenk flask was added into the autoclave by argon pressure supply. A mixture of 2,2-dimethoxypropane (244 μL) [mw. 104.15, 2.05 mmol] and deaeration-treated dehydrated acetone (3 mL) added by argon pressure supply in the Schlenk flask was added into the autoclave by argon pressure supply. Furthermore, the inside of the Schlenk flask was washed with dehydrated acetone (2 mL), and the washing was added into the autoclave by argon pressure supply. Hydrogen was filled therein to 6 MPa, and the mixture was stirred at a reaction temperature of 60° C. for 16 hr. The reaction mixture was allowed to cool to room temperature and depressurized. The reaction mixture was subjected to high performance liquid chromatography and area percentage and optical purity of the resultant product, (3aR,4R,9bR)-benzyl 4-(methoxymethyl)-2,3,3a,4,5,9b-hexahydro-1H-pyrrolo[3,2-c]quinoline-1-carboxylate, were determined to find production at a ratio of 95%. The optical purity was 22% ee.

Example 32

(3aR,4R,9bR)-benzyl 4-(methoxymethyl)-2,3,3a,4,5,9b-hexahydro-1H-pyrrolo[3,2-c]quinoline-1-carboxylate

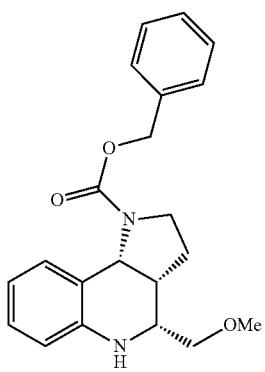 [SMILES: COC[C@@H]1Nc2ccccc2[C@H]2[C@@H]1CCN2C(=O)OCc1ccccc1]

In the same manner as in Example 31 except that (2S,4S)-4-methoxy-skewphos was used as an asymmetric ligand instead of (2S,4S)-3,5-xylyl-skewphos, benzyl 3-(2-methoxy-1-(phenylamino)ethylidene)-2-oxopyrrolidine-1-carboxylate was hydrogenated to give 47% ee. (3aR,4R,9bR)-benzyl 4-(methoxymethyl)-2,3,3a,4,5,9b-hexahydro-1H-pyrrolo[3,2-c]quinoline-1-carboxylate at a ratio of 85%.

Example 33

(3aR,4R,9bR)-benzyl 4-(methoxymethyl)-2,3,3a,4,5,9b-hexahydro-1H-pyrrolo[3,2-c]quinoline-1-carboxylate

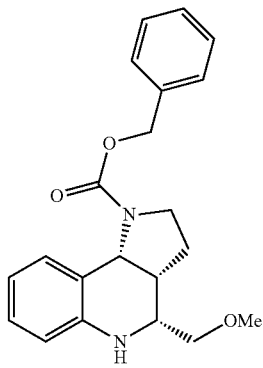 [SMILES: COC[C@@H]1Nc2ccccc2[C@H]2[C@@H]1CCN2C(=O)OCc1ccccc1]

In the same manner as in Example 31 except that (2S,4S)-4-tolyl-skewphos was used as an asymmetric ligand instead of (2S,4S)-3,5-xylyl-skewphos, benzyl 3-(2-methoxy-1-(phenylamino)ethylidene)-2-oxopyrrolidine-1-carboxylate was hydrogenated to give 54% ee. (3aR,4R,9bR)-benzyl 4-(methoxymethyl)-2,3,3a,4,5,9b-hexahydro-1H-pyrrolo[3,2-c]quinoline-1-carboxylate at a ratio of 83%.

Example 34

(3aR,4R,9bR)-benzyl 4-(methoxymethyl)-2,3,3a,4,5,9b-hexahydro-1H-pyrrolo[3,2-c]quinoline-1-carboxylate

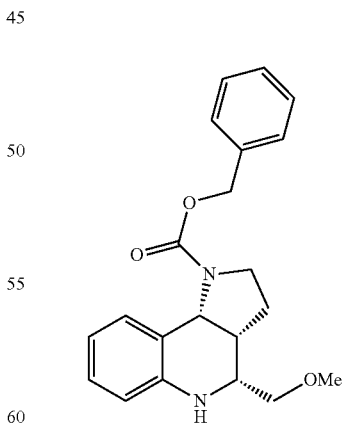

In the same manner as in Example 31 except that (2S,4S)-ptbp-skewphos was used as an asymmetric ligand instead of (2S,4S)-3,5-xylyl-skewphos, benzyl 3-(2-methoxy-1-(phenylamino)ethylidene)-2-oxopyrrolidine-1-carboxylate was hydrogenated to give 60% ee. (3aR,4R,9bR)-benzyl 4-(methoxymethyl)-2,3,3a,4,5,9b-hexahydro-1H-pyrrolo[3,2-c]quinoline-1-carboxylate at a ratio of 94%.

Example 35

Synthesis of (3aR,4R,9bR)-benzyl 4-(methoxymethyl)-2,3,3a,4,5,9b-hexahydro-1H-pyrrolo[3,2-c]quinoline-1-carboxylate 4-methylbenzenesulfonate

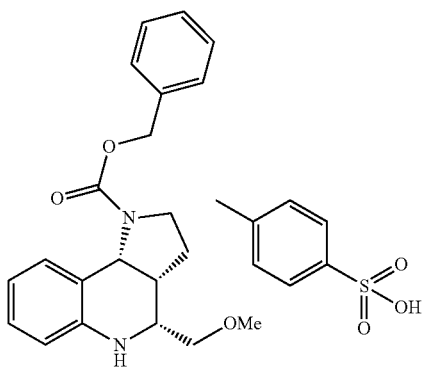

Into a 1 L high-pressure autoclave were charged benzyl 3-(2-methoxy-1-(phenylamino)ethylidene)-2-oxopyrrolidine-1-carboxylate (30.00 g) [mw. 366.41, 81.88 mmol], [Rh(cod)(S,S)-ptbp-skewphos]OTf (1.40 g) [mw. 1025.08, 1.37 mmol, s/c 60] and cyanuric acid (10.57 g) [mw. 129.07, 81.89 mmol, 1 eq.]. The system was substituted with argon 7 times. A mixed solution of dehydrated acetone for organic synthesis (300 mL) and 2,2-dimethoxypropane (15 mL) [d=0.874, mw. 104.15, 125.88 mmol, 1.5 eq.] was added by argon pressure supply. The mixture was stirred at 25° C. for 1 hr. Stirring was discontinued, and the system was substituted with hydrogen gas 10 times. Hydrogen gas pressurized to 6.50 MPa. Stirring was started at 300 rpm, and the mixture was heated to 45° C. The mixture was stirred at the same temperature for 42 hr, and pressurized to keep hydrogen pressure at 5.42-6.50. After cooling to 25° C., the system was substituted with argon, and depressurized. The reaction mixture was concentrated under reduced pressure, ethyl acetate (300 mL) was added and the solvent was substituted. To the concentrate was added ethyl acetate (300 mL), and the mixture was stirred for 1 hr. Insoluble matter was collected by filtration under reduced pressure and washed with ethyl acetate (75 mL). To the washing solution was added p-toluenesulfonic acid monohydrate (15.57 g) [mw. 190.22, 81.85 mmol, 1 eq.] to allow for crystallization of salt. After aging for 1 hr, the crystals were collected by filtration under reduced pressure, washed with ethyl acetate (180 mL), dried in vacuo at 50° C. to give the object compound. White crystalline powder, 36.92 g, yield 85.9%, 62% ee. $^1$H-NMR (500 MHz, CDCl$_3$, TMS) δ1.80-2.10 (m, 2H), 2.30 (s, 3H), 2.70-2.88 (m, 1H), 3.13-3.37 (m, 1H), 3.39 (s, 3H), 3.42-3.64 (m, 1H), 3.69-3.86 (m, 1H), 3.88-4.08 (m, 2H), 5.09-5.38 (m, 3H), 7.05 (d, J=7.88 Hz, 2H), 7.16-7.25 (m, 1H), 7.28-7.46 (m, 5H), 7.54 (d, J=8.20 Hz, 2H), 7.64-7.88 (m, 2H). $^{13}$C-NMR (125 MHz, CDCl$_3$, CDCl$_3$) δ21.27, 21.81-22.14 (m), 22.70-23.03 (m), 36.11-36.39 (m), 45.46, 53.11, 55.48, 59.27, 67.32, 70.23, 123.22-123.67 (m), 125.88, 127.81, 128.11, 128.24-128.38, 128.55, 128.80, 128.84, 129.22-129.37, 130.93-131.08, 136.57, 140.58, 141.15, 156.56.
High performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-AA-302, measurement temperature 30° C., flow rate 1.0 mL/min. high performance liquid chromatography optical purity analysis conditions: UV detector wavelength 220 nm, mobile phase n-hexane for high performance liquid chromatography/2-propanol for high performance liquid chromatography=9/1, column CHIRALPAK AD-H, measurement temperature 25° C., flow rate 1.0 mL/min, retention time 13.2 min ((3aS,4S,9bS)), retention time 14.5 min ((3aR,4R,9bR)).

Example 36

Synthesis of (3aR,4R,9bR)-benzyl 4-(methoxymethyl)-2,3,3a,4,5,9b-hexahydro-1H-pyrrolo[3,2-c]quinoline-1-carboxylate

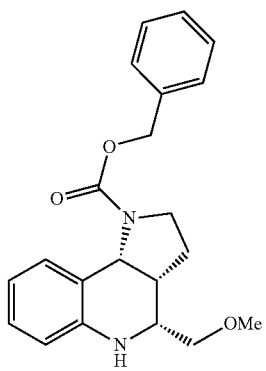 [SMILES: COC[C@@H]1Nc2ccccc2[C@H]2[C@@H]1CCN2C(=O)OCc1ccccc1]

Into a 10 mL Schlenk flask were charged [Rh(cod)$_2$]OTf (19.2 mg) [mw. 468.34, 0.041 mmol, s/c 100] and (2S,4S)-skewphos (21.7 mg) [mw. 440.50, 6.6 μmol], and the system was substituted with argon. Deaeration-treated dehydrated acetone (5 mL) was added by argon pressure supply. Under an argon atmosphere, the mixture was stirred at room temperature for 1 hr. Separately, into a 120 mL stainless autoclave were charged benzyl 3-(2-methoxy-1-(phenylamino)ethylidene)-2-oxopyrrolidine-1-carboxylate (1.50 g) [mw. 366.41, 4.1 mmol] and cyanuric acid (0.53 g) [mw. 129.07, 4.1 mmol], and the system was substituted with argon. The catalyst in the Schlenk flask was added into the autoclave by argon pressure supply. Furthermore, dehydrated acetone (55 mL) and 2,2-dimethoxypropane (1.5 mL) [mw. 104.15, d=0.85, 12.3 mmol, 3.0 eq.] in the Schlenk flask was added into the autoclave by argon pressure supply. Hydrogen was filled therein to 5 MPa, and the mixture was stirred at a reaction temperature of 60° C. for 46 hr. The reaction mixture was cooled to room temperature and depressurized. Quantification by high performance liquid chromatography confirmed that the starting material, benzyl 3-(2-methoxy-1-(phenylamino)ethylidene)-2-oxopyrrolidine-1-carboxylate, remained by 27%, the reaction intermediate, benzyl 3-(2-methoxy-1-(phenylamino)ethyl)-2-oxopyrrolidine-1-carboxylate, remained by 35%, and the resultant product, (3aR,4R,9bR)-benzyl 4-(methoxymethyl)-2,3,3a,4,5,9b-hexahydro-1H-pyrrolo[3,2-c]quinoline-1-carboxylate, was produced by 34%. The optical purity of the resultant product was 60% ee. High performance liquid chromatography production rate analysis conditions: UV detector wavelength 220 nm, mobile phase 50 mmol/L aqueous potassium dihydrogen phosphate solution (adjusted to pH7.0 with 10% aqueous potassium hydroxide solution)/acetonitrile for high performance liquid chromatography=45/55, column YMC-Pack ODS-A A-302, measurement temperature 30° C., flow rate 1.0 mL/min. retention time benzyl 3-(2-methoxy-1-(phenylamino)ethyl)-2-oxopyrrolidine-1-carboxylate 6.9 min (reaction intermediate), (3aR,4R,9bR)-benzyl 4-(methoxymethyl)-2,3,3a,4,5,9b-hexahydro-1H-pyrrolo[3,2-c]quinoline-1-carboxylate 9.7 min (resultant product), benzyl 3-(2-methoxy-1-(phenylamino)ethylidene)-2-oxopyrrolidine-1-carboxylate 10.7 min (starting material). (This analysis method was used for Examples 36-40)

High performance liquid chromatography optical purity analysis conditions: UV detector wavelength 220 nm, mobile phase n-hexane for high performance liquid chromatography/ 2-propanol for high performance liquid chromatography=9/ 1, column CHIRALPAK AD-H, measurement temperature 30° C., flow rate 1.0 mL/min, retention time 11.4 min ((3aS, 4S,9bS)), retention time 12.3 min ((3aR,4R,9bR)). (This analysis method was used for Examples 36-40)

Example 37

Synthesis of (3aR,4R,9bR)-benzyl 4-(methoxymethyl)-2,3,3a,4,5,9b-hexahydro-1H-pyrrolo[3,2-c]quinoline-1-carboxylate

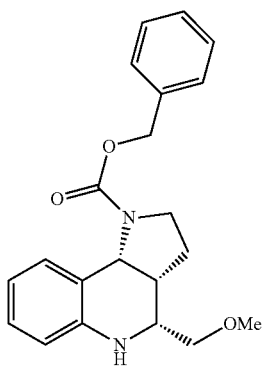 [SMILES: COC[C@@H]1Nc2ccccc2[C@H]2[C@@H]1CCN2C(=O)OCc1ccccc1]

In the same manner as in Example 36 except that (2S,4S)-tolyl-skewphos was used as an asymmetric ligand instead of (2S,4S)-skewphos, benzyl 3-(2-methoxy-1-(phenylamino) ethylidene)-2-oxopyrrolidine-1-carboxylate was hydrogenated. Quantification by high performance liquid chromatography confirmed that the starting material, benzyl 3-(2-methoxy-1-(phenylamino)ethylidene)-2-oxopyrrolidine-1-carboxylate remained by 21%, the reaction intermediate, benzyl 3-(2-methoxy-1-(phenylamino)ethyl)-2-oxopyrrolidine-1-carboxylate, remained by 32%, and the resultant product, (3aR,4R,9bR)-benzyl 4-(methoxymethyl)-2,3,3a,4,5, 9b-hexahydro-1H-pyrrolo[3,2-c]quinoline-1-carboxylate, was produced by 42%. The optical purity of the resultant product was 54% ee.

Example 38

Synthesis of (3aR,4R,9bR)-benzyl 4-(methoxymethyl)-2,3,3a,4,5,9b-hexahydro-1H-pyrrolo[3,2-c]quinoline-1-carboxylate

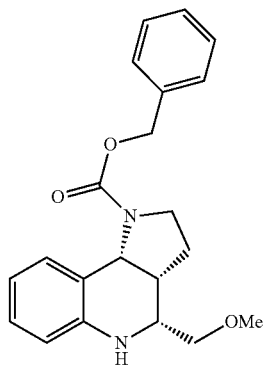 [SMILES: COC[C@@H]1Nc2ccccc2[C@H]2[C@@H]1CCN2C(=O)OCc1ccccc1]

In the same manner as in Example 36 except that (2S,4S)-xylyl-skewphos was used as an asymmetric ligand instead of (2S,4S)-skewphos, benzyl 3-(2-methoxy-1-(phenylamino) ethylidene)-2-oxopyrrolidine-1-carboxylate was hydrogenated. Quantification by high performance liquid chromatography confirmed that the starting material, benzyl 3-(2-methoxy-1-(phenylamino)ethylidene)-2-oxopyrrolidine-1-carboxylate, remained by 11%, the reaction intermediate, benzyl 3-(2-methoxy-1-(phenylamino)ethyl)-2-oxopyrrolidine-1-carboxylate, remained by 32%, and the resultant product, (3aR,4R,9bR)-benzyl 4-(methoxymethyl)-2,3,3a,4,5, 9b-hexahydro-1H-pyrrolo[3,2-c]quinoline-1-carboxylate, was produced by 53%. The optical purity of the resultant product was 20% ee.

Example 39

Synthesis of (3aR,4R,9bR)-benzyl 4-(methoxymethyl)-2,3,3a,4,5,9b-hexahydro-1H-pyrrolo[3,2-c]quinoline-1-carboxylate

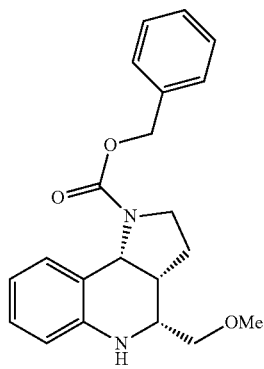 [SMILES: COC[C@@H]1Nc2ccccc2[C@H]2[C@@H]1CCN2C(=O)OCc1ccccc1]

In the same manner as in Example 36 except that (2S,4S)-ptbp-skewphos was used as an asymmetric ligand instead of (2S,4S)-skewphos, benzyl 3-(2-methoxy-1-(phenylamino) ethylidene)-2-oxopyrrolidine-1-carboxylate was hydrogenated. Quantification by high performance liquid chromatography confirmed that the starting material, benzyl 3-(2- methoxy-1-(phenylamino)ethylidene)-2-oxopyrrolidine-1-carboxylate, remained by 10%, the reaction intermediate, benzyl 3-(2-methoxy-1-(phenylamino)ethyl)-2-oxopyrrolidine-1-carboxylate, remained by 21%, and the resultant product, (3aR,4R,9bR)-benzyl 4-(methoxymethyl)-2,3,3a,4,5,9b-hexahydro-1H-pyrrolo[3,2-c]quinoline-1-carboxylate was produced by 67%. The optical purity of the resultant product was 65% ee. The results of Examples 36 to Example 39 are summarized in Table 1 below.

TABLE 1

| Example | quantitative yield (%) | | | optical purity of product |
|---|---|---|---|---|
| | 1 | 2 | 3 | (% ee) |
| 36 | 27 | 35 | 34 | 60 |
| 37 | 21 | 32 | 42 | 54 |
| 38 | 11 | 32 | 53 | 20 |
| 39 | 10 | 21 | 67 | 65 |

Reference Example 52

Synthesis of RuBr$_2$[(s,s)-ptbp-skewphos](pica)

In an argon-substituted 50 mL Schlenk flask were charged (s,s)-ptbp-skewphos (200.0 mg) [mw. 664.92, 0.3 mmol], and Ru(cycloocta-1,5-diene)(methylallyl)$_2$ (96.0 mg) [mw. 319.45, 0.3 mmol], and argon substitution was performed. Hexane (10 mL) was added, and the mixture was stirred at 70° C. for 6 hr, and the solvent was evaporated. The residue was dissolved in acetone (20 mL), 10-20% concentration of HBr ethanol solution (0.32 mL) was added and the mixture was stirred at room temperature for 30 min. The solvent was evaporated, and 2-picolylamine (31 µL) [mw. 108.14, d=1.07, 0.3 mmol] was charged. Then, dimethylformamide (8 mL) was added, and the mixture was stirred at room temperature overnight. The reaction mixture was filtered through a glass filter packed with silica gel, and the solvent was evaporated to give RuBr$_2$[(s,s)-ptbp-skewphos](pica) as a powder.

$^{31}$P-NMR spectrum (202 MHz, H$_2$PO$_4$, Tol-d$_8$): 42.6 (d, J=42 Hz), 62.9 (d, J=42 Hz)

Example 40

Synthesis of (3aR,4R,9bR)-benzyl 4-(methoxymethyl)-2,3,3a,4,5,9b-hexahydro-1H-pyrrolo[3,2-c]quinoline-1-carboxylate

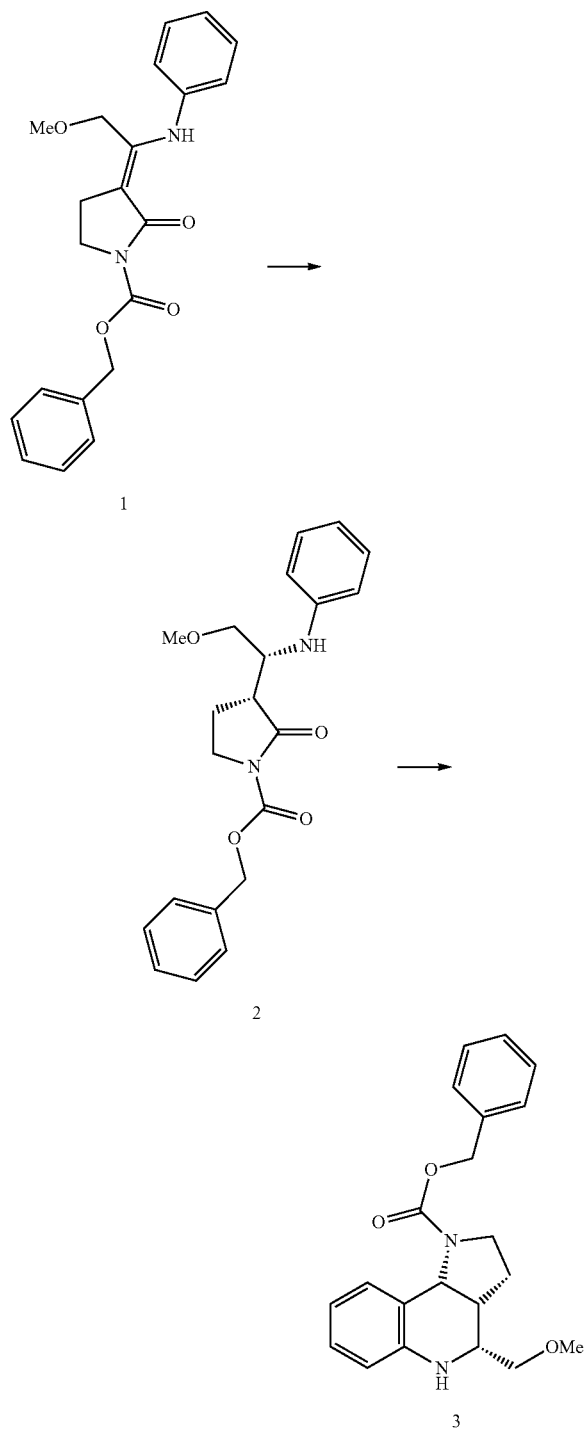

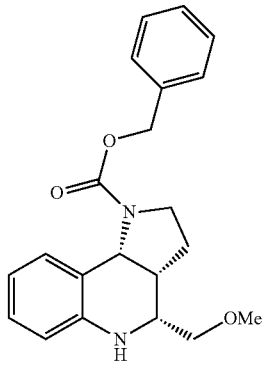 [SMILES: COC[C@@H]1Nc2ccccc2[C@H]2[C@@H]1CCN2C(=O)OCc1ccccc1]

In a 120 mL stainless autoclave were charged benzyl 3-(2-methoxy-1-(phenylamino)ethylidene)-2-oxopyrrolidine-1-carboxylate (1.50 g) [mw. 366.41, 4.1 mmol], cyanuric acid (0.53 g) [mw. 129.07, 4.1 mmol] and RuBr$_2$[(s,s)-ptbp-skewphos](pica) (42.4 mg) [mw. 1033.94, 0.041 mmol] synthesized in Reference Example 52, and the system was substituted with argon. To deaeration-treated dehydrated acetone (55 mL) was added 2,2-dimethoxypropane (1.5 mL) [mw. 104.15, d=0.85, 12.3 mmol, 3.0 eq.] and the mixture was added to the autoclave by argon pressure supply. Furthermore, 2,2-dimethoxypropane was rinsed with dehydrated acetone (5 mL), and added by argon pressure supply. Hydrogen was filled therein to 5 MPa, and the mixture was stirred at a reaction temperature of 60° C. for 46 hr. The reaction mixture was cooled to room temperature and depressurized. Quantification by high performance liquid chromatography confirmed that the starting material, benzyl 3-(2-methoxy-1-(phenylamino)ethylidene)-2-oxopyrrolidine-1-carboxylate, remained, the reaction intermediate, benzyl 3-(2-methoxy-1-(phenylamino)ethyl)-2-oxopyrrolidine-1-carboxylate, was not more than 1%, and the resultant product, (3aR,4R,9bR)-benzyl 4-(methoxymethyl)-2,3,3a,4,5,9b-hexahydro-1H-pyrrolo[3,2-c]quinoline-1-carboxylate, was also not more than 1%.

Reference Example 53

Synthesis of optically active
N'-(1-phenylethyl)benzohydrazide

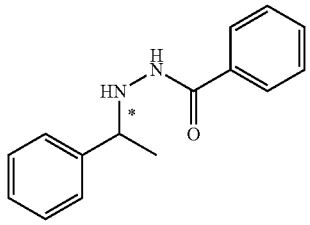 [SMILES: CC(NNC(=O)c1ccccc1)c1ccccc1]

In a hydrogenation reaction apparatus Endeavor were charged (E)-N'-(1-phenylethylidene)benzohydrazide (119 mg) [mw. 238.28, 0.5 mmol], and [Rh(cod)(S,S)-ptbp-skew-phos)]OTf (5.1 mg) [mw. 1025.08, 5.0 μmol, s/c 100]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide remained by 20%, and the resultant product, N'-(1-phenylethyl)benzohydrazide, was confirmed to show an area percentage of 79%. The optical purity of the resultant product was 7% ee.

Example 41

Synthesis of optically active
N'-(1-phenylethyl)benzohydrazide

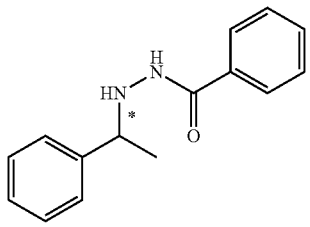 [SMILES: CC(NNC(=O)c1ccccc1)c1ccccc1]

In a hydrogenation reaction apparatus Endeavor were charged (E)-N'-(1-phenylethylidene)benzohydrazide (119 mg) [mw. 238.28, 0.5 mmol], [Rh(cod) (S,S)-ptbp-skew-phos)]OTf (5.1 mg) [mw. 1025.08, 5.0 μmol, s/c 100] and cyanuric acid (6.5 mg) [mw. 129.07, 0.05 mmol]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide remained by 20%, and the resultant product, N'-(1-phenylethyl)benzohydrazide, was confirmed to show an area percentage of 79%. The optical purity of the resultant product was 4% ee.

Example 42

Synthesis of optically active
N'-(1-phenylethyl)benzohydrazide

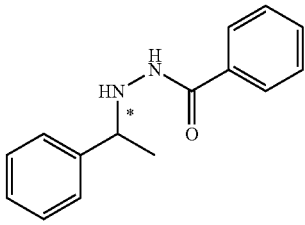 [SMILES: CC(NNC(=O)c1ccccc1)c1ccccc1]

In a hydrogenation reaction apparatus Endeavor were charged (E)-N'-(1-phenylethylidene)benzohydrazide (119 mg) [mw. 238.28, 0.5 mmol], [Rh(cod) (S,S)-ptbp-skew-phos)]OTf (5.1 mg) [mw. 1025.08, 5.0 μmol, s/c 100] and phenol (4.7 mg) [mw. 94.11, 0.05 mmol]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide remained by 17%, and the resultant product, N'-(1-phenylethyl)benzohydrazide, was confirmed to show an area percentage of 82%. The optical purity of the resultant product was 7% ee.

Example 43

Synthesis of optically active
N'-(1-phenylethyl)benzohydrazide

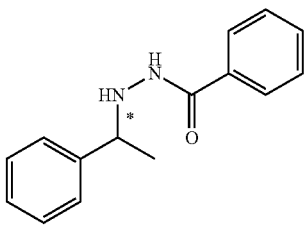 [SMILES: CC(NNC(=O)c1ccccc1)c1ccccc1]

In a hydrogenation reaction apparatus Endeavor were charged (E)-N'-(1-phenylethylidene)benzohydrazide (119 mg) [mw. 238.28, 0.5 mmol], [Rh(cod) (S,S)-ptbp-skewphos)]OTf (5.1 mg) [mw. 1025.08, 5.0 μmol, s/c 100] and (S)-BINOL (14.3 mg) [mw. 286.32, 0.05 mmol]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 15%, and the resultant product, N'-(1-phenylethyl)benzohydrazide, was confirmed to show an area percentage of 84%. The optical purity of the resultant product was 4% ee.

Example 44

Synthesis of optically active
N'-(1-phenylethyl)benzohydrazide

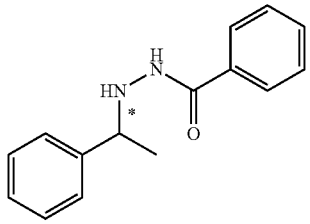 [SMILES: CC(NNC(=O)c1ccccc1)c1ccccc1]

In a hydrogenation reaction apparatus Endeavor were charged (E)-N'-(1-phenylethylidene)benzohydrazide (119 mg) [mw. 238.28, 0.5 mmol], [Rh(cod) (S,S)-ptbp-skewphos)]OTf (5.1 mg) [mw. 1025.08, 5.0 μmol, s/c 100] and resorcinol (5.5 mg) [mw. 110.11, 0.05 mmol]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 14%, and the resultant product, N'-(1-phenylethyl)benzohydrazide, was confirmed to show an area percentage of 84%. The optical purity of the resultant product was 5% ee.

Example 45

Synthesis of optically active
N'-(1-phenylethyl)benzohydrazide

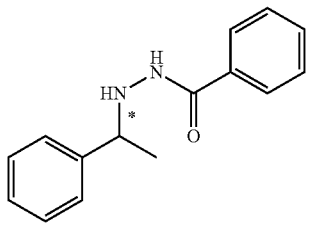 [SMILES: CC(NNC(=O)c1ccccc1)c1ccccc1]

In a hydrogenation reaction apparatus Endeavor were charged (E)-N'-(1-phenylethylidene)benzohydrazide (119 mg) [mw. 238.28, 0.5 mmol], [Rh(cod) (S,S)-ptbp-skewphos)]OTf (5.1 mg) [mw. 1025.08, 5.0 μmol, s/c 100] and menthol (7.8 mg) [mw. 156.27, 0.05 mmol]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 13%, and the resultant product, N'-(1-phenylethyl)benzohydrazide, was confirmed to show an area percentage of 85%. The optical purity of the resultant product was 6% ee.

Example 46

Synthesis of optically active
N'-(1-phenylethyl)benzohydrazide

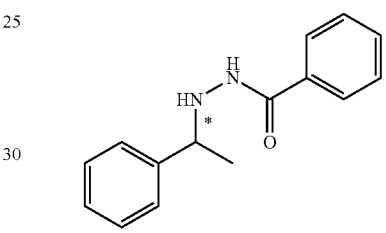

In a hydrogenation reaction apparatus Endeavor were charged (E)-N'-(1-phenylethylidene)benzohydrazide (119 mg) [mw. 238.28, 0.5 mmol], [Rh(cod)(S,S)-ptbp-skewphos)]OTf (5.1 mg) [mw. 1025.08, 5.0 mol, s/c 100] and (2R,4S)-pentane-2,4-diyl bis(4-methylbenzenesulfonate) (20.6 mg) [mw. 412.52, 0.05 mmol]. The system was substituted with argon 7 times. Dehydrated acetone for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 15%, and the resultant product, N'-(1-phenylethyl)benzohydrazide, was confirmed to show an area percentage of 83%. The optical purity of the resultant product was 1% ee.

Reference Example 54

Synthesis of optically active methyl
2-acetamide-3-phenylpropanoate

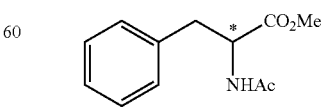

In a 120 mL high-pressure autoclave were charged (Z)-methyl 2-acetamide-3-phenylacrylate (3.20 g) [mw. 219.24, 14.6 mmol], and [Rh(cod) (S,S)-ptbp-skewphos)]OTf (3.0 mg) [mw. 1025.08, 2.9 µmol, s/c 5000]. The system was substituted with argon 7 times. Dehydrated methanol for organic synthesis (5 mL) was added by argon pressure supply. The system was substituted with hydrogen gas, and the mixture was stirred with hydrogen gas pressurization at 1.0 MPa for 3 hr. The system was depressurized, and analyzed by high performance liquid chromatography to find that the starting material, (Z)-methyl 2-acetamide-3-phenylacrylate, completely disappeared, the resultant product, methyl 2-acetamide-3-phenylpropanoate, was confirmed, and the optical purity was 87% ee.

High performance liquid chromatography production rate analysis conditions: UV detector wavelength 254 nm, mobile phase 25 mmol/L dipotassium hydrogen phosphate aqueous solution/acetonitrile for high performance liquid chromatography=7/3, column YMC-Pack ODS-A A-302, measurement temperature 25° C., flow rate 0.5 mL/min, retention time 10.4 min ((Z)-methyl 2-acetamide-3-phenylacrylate, starting material), 11.9 min (methyl 2-acetamide-3-phenylpropanoate, resultant product).

High performance liquid chromatography optical purity analysis conditions: UV detector wavelength 254 nm, mobile phase high speed liquid
n-hexane for chromatography/2-propanol for high performance liquid chromatography=9/1, column CHIRALCEL OJ-H, measurement temperature 30° C., flow rate 1.0 mL/min, retention time 10.0 min (former half peak), 14.5 min (latter half peak).

Reference Example 55

Synthesis of optically active N'-(1-phenylethyl)benzohydrazide

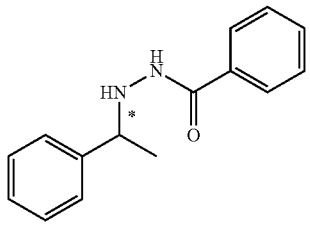

In a 120 mL high-pressure autoclave were charged (E)-N'-(1-phenylethylidene)benzohydrazide (119 mg) [mw. 238.28, 0.5 mmol], and [Rh(cod)(S,S)-ptbp-skewphos]OTf (5.1 mg) [mw. 1025.08, 5.0 µmol, s/c 100]. The system was substituted with argon 7 times. Dehydrated methanol for organic synthesis (5 mL) was added by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 27%, and the resultant product, N'-(1-phenylethyl)benzohydrazide, was confirmed to show an area percentage of 72%. The optical purity of the resultant product was 18% ee.

High performance liquid chromatography production rate analysis conditions: UV detector wavelength 254 nm, mobile phase 25 mmol/L dipotassium hydrogen phosphate aqueous solution/acetonitrile for high performance liquid chromatography=7/3, column YMC-Pack ODS-A A-302, measurement temperature 25° C., flow rate 0.5 mL/min, retention time 17.4 min (N'-(1-phenylethyl)benzohydrazide, resultant product), 19.4 min ((E)-N'-(1-phenylethylidene)benzohydrazide, starting material). (This analysis method was used for Examples IMI-IMI-3) high performance liquid chromatography optical purity analysis conditions: UV detector wavelength 254 nm, mobile phase n-hexane for high performance liquid chromatography/2-propanol for high performance liquid chromatography=9/1, column CHIRALCEL OJ-H, measurement temperature 40° C., flow rate 1.0 mL/min, retention time 7.7 min (former half peak), 9.9 min (latter half peak). (This analysis method was used for Reference Examples 55-57)

Reference Example 56

Synthesis of optically active N'-(1-phenylethyl)benzohydrazide

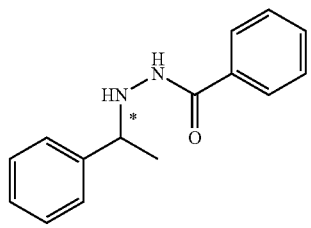 [SMILES: CC(NNC(=O)c1ccccc1)c1ccccc1]

In the same manner as in Example IMI except that dehydrated acetone was used as a solvent instead of dehydrated methanol, (E)-N'-(1-phenylethylidene)benzohydrazide was hydrogenated. High performance liquid chromatography revealed that the starting material, (E)-N'-(1-phenylethylidene)benzohydrazide, remained by 25%, and the resultant product, N'-(1-phenylethyl)benzohydrazide, was confirmed to show an area percentage of 74%. The optical purity of the resultant product was 9% ee.

Reference Example 57

Synthesis of optically active N'-(1-phenylethyl)benzohydrazide

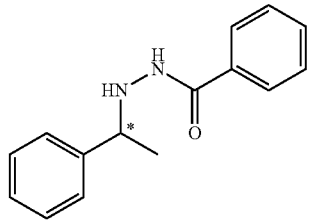 [SMILES: CC(NNC(=O)c1ccccc1)c1ccccc1]

In a 120 mL high-pressure autoclave were charged (E)-N'-(1-phenylethylidene)benzohydrazide (119 mg) [mw. 238.28, 0.5 mmol], [Rh(cod) (S,S)-ptbp-skewphos]OTf (5.1 mg) [mw. 1025.08, 5.0 µmol, s/c 100], and methanesulfonic acid (0.5 mg) [mw. 96.11, 5.0 µmol, 0.01 eq.]. The system was substituted with argon 7 times. 10 mL Schlenk flask was substituted with argon, pure water (9 mg) [mw. 18.02, 0.5 mmol, 1.0 eq.] and dehydrated acetone for organic synthesis (5 mL) were added, and the solution was fed into an autoclave by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 43%, and the resultant product, N'-(1-phenylethyl)benzohydrazide was produced by 45%, and the decomposed product, acetophenone, was produced by 7%.

Example 47

Synthesis of optically active N'-(1-phenylethyl)benzohydrazide

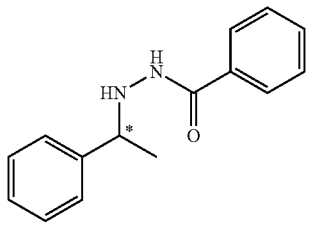 [SMILES: CC(NNC(=O)c1ccccc1)c1ccccc1]

In a 120 mL high-pressure autoclave were charged (E)-N'-(1-phenylethylidene)benzohydrazide (119 mg) [mw. 238.28, 0.5 mmol], [Rh(cod) (S,S)-ptbp-skewphos)]OTf (5.1 mg) [mw. 1025.08, 5.0 μmol, s/c 100], and methanesulfonic acid (0.5 mg) [mw. 96.11, 5.0 μmol, 0.01 eq.]. The system was argon-substituted 7 times. 10 mL Schlenk flask was substituted with argon, and pure water (9 mg) [mw. 18.02, 0.5 mmol, 1.0 eq.], 2,2-dimethoxypropane (0.18 mL) [mw. 104.15, d=0.85, 1.5 mmol, 3.0 eq.] and dehydrated acetone for organic synthesis (5 mL) were added. The solution was fed into an autoclave by argon pressure supply. The system was substituted with hydrogen gas, and the mixture was stirred with hydrogen gas pressurization at 1.0 MPa for 2 hr. The system was depressurized, and analyzed by high performance liquid chromatography to find that the starting material, (E)-N'-(1-phenylethylidene)benzohydrazide, remained by 38%, and the resultant product, N'-(1-phenylethyl)benzohydrazide was produced by 59%, and the decomposed product, acetophenone, was produced by 1%.

Reference Example 58

Synthesis of (3aS,4R,9bR)-4-(methoxymethyl)-2,3,3a,4,5,9b-hexahydro-1H-pyrrolo[3,2-c]quinoline

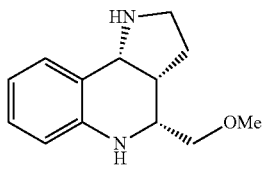 [SMILES: COC[C@@H]1Nc2ccccc2[C@@H]2NCC[C@H]12]

In a 500 mL four-mouthed flask were added (3aR,4R,9bR)-benzyl 4-(methoxymethyl)-2,3,3a,4,5,9b-hexahydro-1H-pyrrolo[3,2-c]quinoline-1-carboxylate 4-methylbenzenesulfonate (47.37 g) [mw. 524.63, 90.29 mmol] and 6 mol/L aqueous hydrochloric acid solution (237 mL). The mixture was heated to 80° C., and stirred at the same temperature for 2 hr. After cooling to 25° C., toluene (237 mL) was added, and the mixture was stirred for 15 min. After partitioning, activated carbon Shirasagi A (3.2 g) was added to the aqueous layer, and the mixture was stirred for 30 min. Activated carbon was collected by filtration, washed with water (119 mL), and 8 mol/L aqueous sodium hydroxide solution (288 mL) was added to the washing solution at 20-30° C. The obtained crystallization liquid was aged for 1 hr, and the crystals were collected by filtration under reduced pressure, washed with water (95 mL), and dried in vacuo at 60° C. to give the object compound. White crystalline powder, 16.88 g, yield 85.6%, 71% ee., $^1$H-NMR (500 MHz, CDCl$_3$, TMS) δ1.61-1.72 (m, 1H), 1.73-1.84 (m, 1H), 1.85-2.08 (m, 1H), 2.33-2.48 (m, 1H), 2.77-2.87 (m, 1H), 2.87-2.97 (m, 1H), 3.35-3.43 (m, 4H), 3.44-3.51 (m, 1H), 4.08 (br. s, 1H), 4.40 (d, J=8.20 Hz, 1H), 6.55 (d, J=7.25 Hz, 1H), 6.69-6.80 (m, 1H), 6.97-7.05 (m, 1H), 7.21 (d, J=7.57 Hz, 1H). $^{13}$C-NMR (125 MHz, CDCl$_3$, CDCl$_3$) δ24.88, 40.97, 45.62, 52.48, 57.74, 58.96, 75.47, 114.89, 118.94, 125.42, 127.48, 129.03, 144.82.

High performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-AA-302, measurement temperature 30° C., flow rate 1.0 mL/min.

High performance liquid chromatography optical purity analysis conditions: UV detector wavelength 254 nm, mobile phase 0.1 mol/L aqueous potassium fluoride solution/acetonitrile for high performance liquid chromatography=85/15, column CHIRALCEL OD-RH, measurement temperature 25° C., flow rate 1.0 mL/min, retention time 15.0 min ((3aR, 4S,9bS)), retention time 16.4 min ((3aS,4R,9bR)).

Reference Example 59

Synthesis of (3aS,4R,9bR)-4-(methoxymethyl)-2,3,3a,4,5,9b-hexahydro-1H-pyrrolo[3,2-c]quinoline(2R,3R)-2,3-dihydroxysuccinate

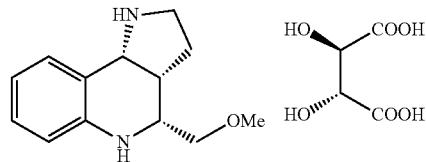 [SMILES: COC[C@@H]1Nc2ccccc2[C@@H]2NCC[C@H]12 ; O=C(O)[C@H](O)[C@@H](O)C(=O)O]

In a 500 mL four-mouthed flask were added L-tartaric acid (6.19 g) [mw. 150.09, 41.24 mmol, 1 eq.] and ethanol (248 mL). The mixture was dissolved by heating to 50° C. (3aS,4R,9bR)-4-(methoxymethyl)-2,3,3a,4,5,9b-hexahydro-1H-pyrrolo[3,2-c]quinoline (9.00 g) [mw. 218.29, 41.22 mmol] was added. The crystallization liquid was stirred at 50° C. for 30 min. After cooling to 25° C., the mixture was aged for 1 hr, and the crystals were collected by filtration under reduced pressure, washed with ethanol (54 mL), and dried in vacuo at 50° C. to give the object compound. White crystalline powder, 11.75 g, yield 77.4%, 98% de., $^1$H-NMR (500 MHz, D$_2$O, TMS) δ1.85-2.11 (m, 2H), 2.73-2.88 (m, 1H), 3.12-3.28 (m, 2H), 3.34 (s, 3H), 3.42-3.59 (m, 3H), 4.42 (s, 2H), 5.02 (d, J=9.14 Hz, 1H), 6.76 (d, J=8.20 Hz, 1H), 6.84-6.86 (m, 1H), 7.11-7.23 (m, 2H). $^{13}$C-NMR (125 MHz, D$_2$O) δ22.69, 38.68, 44.72, 51.20, 57.79, 58.51, 72.87, 73.51, 116.54, 116.84, 120.23, 129.58, 130.16, 145.83, 176.38.

High performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-A A-302, measurement temperature 30° C., flow rate 1.0 mL/min.

High performance liquid chromatography optical purity analysis conditions: UV detector wavelength 254 nm, mobile phase 0.1 mol/L aqueous potassium fluoride solution/acetonitrile for high performance liquid chromatography=85/15, column CHIRALCEL OD-RH, measurement temperature 25° C., flow rate 1.0 mL/min, retention time 15.0 min ((3aR,4S,9bS)), retention time 16.4 min ((3aS,4R,9bR)).

Reference Example 60

(3aR,4R,9bR)-benzyl 4-(methoxymethyl)-2,3,3a,4,5,9b-hexahydro-1H-pyrrolo[3,2-c]quinoline-1-carboxylate

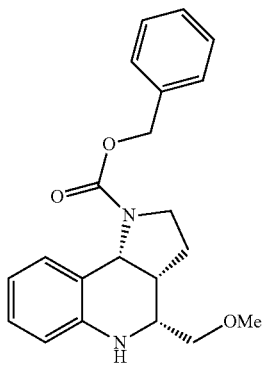 [SMILES: COC[C@@H]1Nc2ccccc2[C@H]2[C@@H]1CCN2C(=O)OCc1ccccc1]

Under an argon atmosphere, in a 50 mL Schlenk flask were added [Ru(MeCN)$_3$Cp](2.3 mg) [mw. 434.30, 0.0053 mmol, s/c 25] and (2S,4S)-Skewphos (2.8 mg) [mw. 440.49, 0.0064 mmol], and argon-substitution was performed. Dehydrated methanol (1 mL) was added, and the mixture was stirred at room temperature for 1 hr. Separately, in a 120 mL stainless steel autoclave was added benzyl 3-(2-methoxy-1-(phenylamino)ethylidene)-2-oxopyrrolidine-1-carboxylate (50.0 mg) [mw. 366.41, 0.1365 mmol] and the mixture was substituted with argon. The above ruthenium catalyst solution was added by argon pressure supply, then dehydrated methanol (4 mL) was added. Hydrogen was filled therein to 5 MPa, and the mixture was stirred at a reaction temperature of 50° C. for 16 hr. The reaction mixture was allowed to cool to room temperature and depressurized. The reaction mixture was subjected to high performance liquid chromatography and the area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined to find production at a ratio of not more than 1%.

High performance liquid chromatography analysis conditions: UV detector wavelength 220 nm, mobile phase 50 mmol/L potassium dihydrogen phosphate Aqueous solution (adjusted to pH7.0 with 10% aqueous sodium hydroxide solution)/acetonitrile for high performance liquid chromatography=45/55, column YMC-Pack ODS-A A-302, measurement temperature 30° C., flow rate 1.0 mL/min.

Reference Example 61

(3aR,4R,9bR)-benzyl 4-(methoxymethyl)-2,3,3a,4,5,9b-hexahydro-1H-pyrrolo[3,2-c]quinoline-1-carboxylate

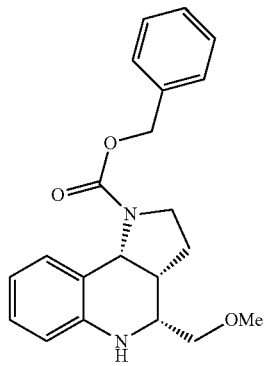 [SMILES: COC[C@@H]1Nc2ccccc2[C@H]2[C@@H]1CCN2C(=O)OCc1ccccc1]

In the same manner as in Reference Example 60 except that [Cu(MeCN)$_4$]PF6 2.0 mg) [mw. 372.72, 0.0054 mmol] was used instead of [Ru(MeCN)$_3$Cp], benzyl 3-(2-methoxy-1-(phenylamino)ethylidene)-2-oxopyrrolidine-1-carboxylate was hydrogenated. The area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find not more than 1%.

Reference Example 62

(3aR,4R,9bR)-benzyl 4-(methoxymethyl)-2,3,3a,4,5,9b-hexahydro-1H-pyrrolo[3,2-c]quinoline-1-carboxylate

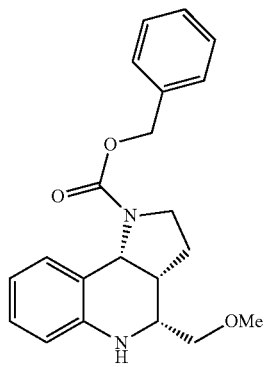 [SMILES: COC[C@@H]1Nc2ccccc2[C@H]2[C@@H]1CCN2C(=O)OCc1ccccc1]

In the same manner as in Reference Example 60 except that [Pd$_2$Cl$_2$(C$_3$H$_5$)$_2$]PF$_6$ (2.0 mg) [mw. 365.89, 0.0055 mmol] was used instead of [Ru(MeCN)$_3$Cp], benzyl 3-(2-methoxy-1-(phenylamino)ethylidene)-2-oxopyrrolidine-1-carboxylate was hydrogenated. The area percentage of the resultant product, (3aR,4R,9bR)-benzyl 4-(methoxymethyl)-2,3,3a,4, 5,9b-hexahydro-1H-pyrrolo[3,2-c]quinoline-1-carboxylate, was determined by high performance liquid chromatography to find not more than 1%.

Reference Example 63

(3aR,4R,9bR)-benzyl 4-(methoxymethyl)-2,3,3a,4,5,9b-hexahydro-1H-pyrrolo[3,2-c]quinoline-1-carboxylate

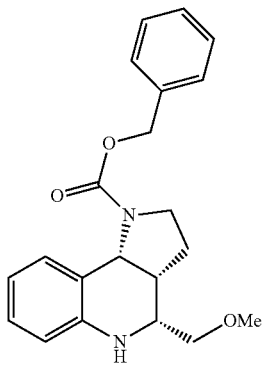 [SMILES: COC[C@@H]1Nc2ccccc2[C@H]2[C@@H]1CCN2C(=O)OCc1ccccc1]

In the same manner as in Reference Example 60 except that Zn(OTf)₂ (2.0 mg) [mw. 363.85, 0.0055 mmol] was used instead of [Ru(MeCN)₃Cp], benzyl 3-(2-methoxy-1-(phenylamino)ethylidene)-2-oxopyrrolidine-1-carboxylate was hydrogenated. The area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find not more than 1%.

Reference Example 64

(3aR,4R,9bR)-benzyl 4-(methoxymethyl)-2,3,3a,4,5,9b-hexahydro-1H-pyrrolo[3,2-c]quinoline-1-carboxylate

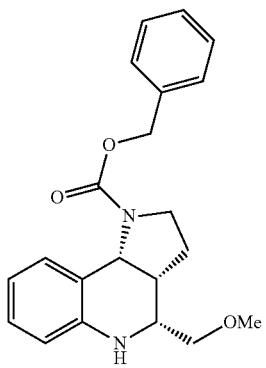 [SMILES: COC[C@@H]1Nc2ccccc2[C@H]2[C@@H]1CCN2C(=O)OCc1ccccc1]

Under an argon atmosphere, in a 10 mL Schlenk flask were added [Ir(cod)₂]BF₄ (10.0 mg) [mw. 495.40, 0.020 mmol, s/c 25] and (2S,4S)-Skewphos (11.0 mg) [mw. 440.49, 0.025 mmol], and argon-substitution was performed. Dehydrated methanol (2 mL) was added, and the mixture was stirred at room temperature for 0.5 hr. Separately, in a 120 mL stainless steel autoclave was added benzyl 3-(2-methoxy-1-(phenylamino)ethylidene)-2-oxopyrrolidine-1-carboxylate (185.0 mg) [mw. 366.41, 0.505 mmol] and the mixture was substituted with argon. The above iridium catalyst solution was added by argon pressure supply, then dehydrated methanol (2 mL) was added. Hydrogen was filled therein to 5 MPa, and the mixture was stirred at a reaction temperature of 40° C. for 16 hr. The reaction mixture was allowed to cool to room temperature and depressurized. The reaction mixture was subjected to high performance liquid chromatography and the area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined to find production at a ratio of not more than 1%. However, the intermediate, the following benzyl 3-(2-methoxy-1-(phenylamino)ethyl)-2-oxopyrrolidine-1-carboxylate

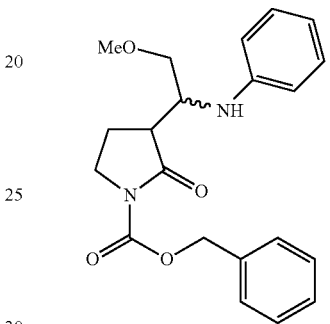

was produced by 33%.

High performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-AA-302, measurement temperature 30° C., flow rate 1.0 mL/min.

Reference Example 65

(3aR,4R,9bR)-benzyl 4-(methoxymethyl)-2,3,3a,4,5,9b-hexahydro-1H-pyrrolo[3,2-c]quinoline-1-carboxylate

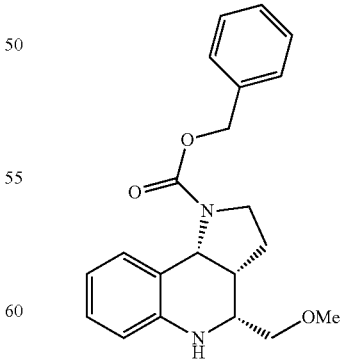

Under an argon atmosphere, in a 10 mL Schlenk flask were added [Rh(cod)₂]OTf (2.4 mg) [mw. 468.34, 0.0051 mmol, s/c 25] and (R)—(S)-JOSIPHOS (3.4 mg) [mw. 594.59, 0.0057 mmol], and argon-substitution was performed. Dehydrated methanol (1 mL) was added, and the mixture was stirred at room temperature for 1 hr. Separately, in a 120 mL stainless steel autoclave was added benzyl 3-(2-methoxy-1-(phenylamino)ethylidene)-2-oxopyrrolidine-1-carboxylate (50.0 mg) [mw. 366.41, 0.1365 mmol] and the mixture was substituted with argon. The above rhodium catalyst solution was added by argon pressure supply, then dehydrated methanol (4 mL) was added. Hydrogen was filled therein to 1 MPa, and the mixture was stirred at a reaction temperature of 50° C. for 16 hr. The reaction mixture was allowed to cool to room temperature and depressurized. The reaction mixture was subjected to high performance liquid chromatography and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined to find production at a ratio of 25%. In addition, the intermediate, the following benzyl 3-(2-methoxy-1-(phenylamino)ethyl)-2-oxopyrrolidine-1-carboxylate

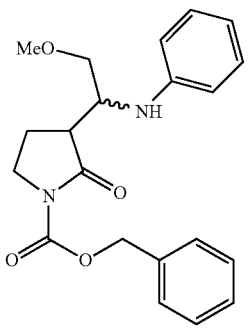 [SMILES: COCC(Nc1ccccc1)C1CCN(C(=O)OCc2ccccc2)C1=O]

was produced by 8%.

high performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-A A-302, measurement temperature 30° C., flow rate 1.0 mL/min.

Reference Example 66

(3aR,4R,9bR)-benzyl 4-(methoxymethyl)-2,3,3a,4,5,9b-hexahydro-1H-pyrrolo[3,2-c]quinoline-1-carboxylate

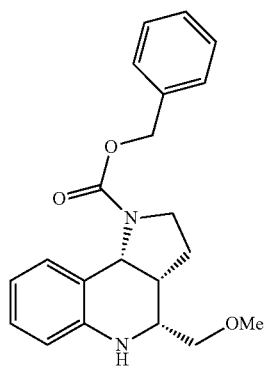 [SMILES: COC[C@@H]1Nc2ccccc2[C@H]2[C@@H]1CCN2C(=O)OCc1ccccc1]

Under an argon atmosphere, in a 10 mL Schlenk flask were added [Rh(cod)₂]OTf (2.4 mg) [mw. 468.34, 0.0051 mmol, s/c 25] and (S)-BINAP (3.8 mg) [mw. 622.67, 0.0061 mmol], and argon-substitution was performed. Dehydrated methanol (1 mL) was added, and the mixture was stirred at room temperature for 1 hr. Separately, in a 120 mL stainless steel autoclave was added benzyl 3-(2-methoxy-1-(phenylamino)ethylidene)-2-oxopyrrolidine-1-carboxylate (50.0 mg) [mw. 366.41, 0.1365 mmol] and the mixture was substituted with argon. The above rhodium catalyst solution was added by argon pressure supply, then dehydrated methanol (4 mL) was added. Hydrogen was filled therein to 1 MPa, and the mixture was stirred at a reaction temperature of 50° C. for 16 hr. The reaction mixture was allowed to cool to room temperature and depressurized. The reaction mixture was subjected to high performance liquid chromatography and area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined to find production at a ratio of not more than 1%. In addition, the intermediate, the following benzyl 3-(2-methoxy-1-(phenylamino)ethyl)-2-oxopyrrolidine-1-carboxylate

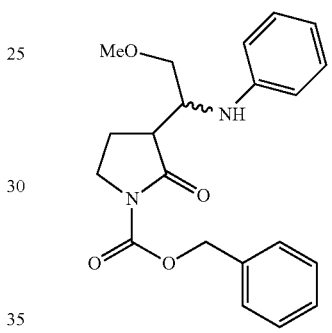

was produced by 2%.

High performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-A A-302, measurement temperature 30° C., flow rate 1.0 mL/min.

Reference Example 67

(3aR,4R,9bR)-benzyl 4-(methoxymethyl)-2,3,3a,4,5,9b-hexahydro-1H-pyrrolo[3,2-c]quinoline-1-carboxylate

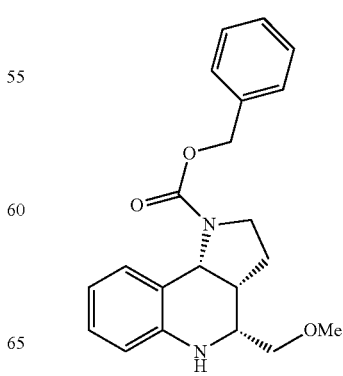

Under an argon atmosphere, in a 10 mL Schlenk flask were added [Rh(cod)$_2$]OTf (2.4 mg) [mw. 468.34, 0.0051 mmol, s/c 25] and (2S,5S)-Me-Duphos (1.9 mg) [mw. 306.37, 0.0062 mmol], and argon-substitution was performed. Dehydrated methanol (1 mL) was added, and the mixture was stirred at room temperature for 1 hr. Separately, in a 120 mL stainless steel autoclave was added benzyl 3-(2-methoxy-1-(phenylamino)ethylidene)-2-oxopyrrolidine-1-carboxylate (50.0 mg) [mw. 366.41, 0.1365 mmol] and the mixture was substituted with argon. The above rhodium catalyst solution was added by argon pressure supply, then dehydrated methanol (4 mL) was added. Hydrogen was filled therein to 1 MPa, and the mixture was stirred at a reaction temperature of 50° C. for 16 hr. The reaction mixture was allowed to cool to room temperature and depressurized. The reaction mixture was subjected to high performance liquid chromatography and area percentage of the resultant product, 71% ee. (3aR,4R, 9bR)-benzyl 4-(methoxymethyl)-2,3,3a,4,5,9b-hexahydro-1H-pyrrolo[3,2-c]quinoline-1-carboxylate, was determined to find production at a ratio of 16%. In addition, the intermediate, the following benzyl 3-(2-methoxy-1-(phenylamino)ethyl)-2-oxopyrrolidine-1-carboxylate

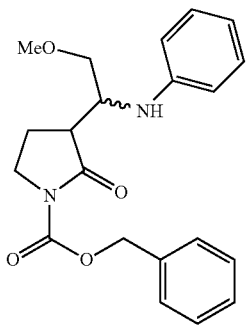 [SMILES: COCC(Nc1ccccc1)C1CCN(C(=O)OCc2ccccc2)C1=O]

was produced by 32%.

High performance liquid chromatography analysis conditions: UV detector wavelength 220 nm, mobile phase 50 mmol/L aqueous potassium dihydrogen phosphate solution (adjusted to pH7.0 with 10% aqueous sodium hydroxide solution)/acetonitrile for high performance liquid chromatography=45/55, column YMC-Pack ODS-A A-302, measurement temperature 30° C., flow rate 1.0 mL/min.

Reference Example 68

(3aR,4R,9bR)-benzyl 4-(methoxymethyl)-2,3,3a,4,5,9b-hexahydro-1H-pyrrolo[3,2-c]quinoline-1-carboxylate

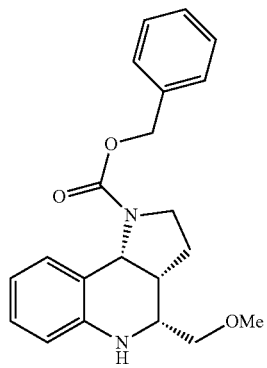 [SMILES: COC[C@@H]1Nc2ccccc2[C@H]2[C@@H]1CCN2C(=O)OCc1ccccc1]

In the same manner as in Reference Example 67 except that (2S,5S)-Et-Duphos (2.3 mg) [mw. 362.48, 0.0063 mmol] was used instead of (2S,5S)-Me-Duphos, benzyl 3-(2-methoxy-1-(phenylamino)ethylidene)-2-oxopyrrolidine-1-carboxylate was hydrogenated. The area percentage of the resultant product, 69% ee. (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at a ratio of 26%. In addition, the intermediate, the following benzyl 3-(2-methoxy-1-(phenylamino)ethyl)-2-oxopyrrolidine-1-carboxylate

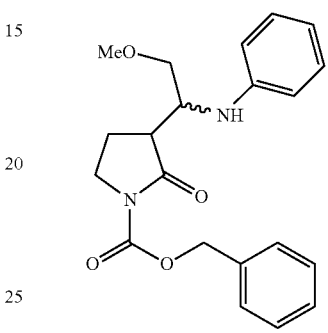

was produced by 36%.

Reference Example 69

(3aR,4R,9bR)-benzyl 4-(methoxymethyl)-2,3,3a,4,5,9b-hexahydro-1H-pyrrolo[3,2-c]quinoline-1-carboxylate

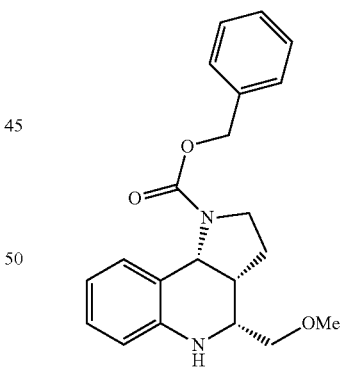

In the same manner as in Reference Example 67 except that (2S,5S)-$^i$Pr-Duphos (2.6 mg) [mw. 418.58, 0.0062 mmol] was used instead of (2S,5S)-Me-Duphos, benzyl 3-(2-methoxy-1-(phenylamino)ethylidene)-2-oxopyrrolidine-1-carboxylate was hydrogenated. The area percentage of the resultant product, (3aR,4R,9bR)-benzyl 4-(methoxymethyl)-2,3,3a,4,5,9b-hexahydro-1H-pyrrolo[3,2-c]quinoline-1-carboxylate, was determined by high performance liquid chromatography to find production at a ratio of 13%. In addition, the intermediate, the following benzyl 3-(2-methoxy-1-(phenylamino)ethyl)-2-oxopyrrolidine-1-carboxylate

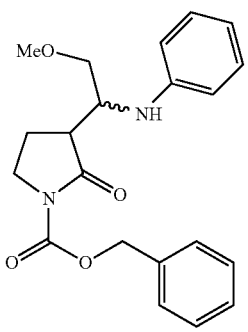 [SMILES: COCC(Nc1ccccc1)C1CCN(C(=O)OCc2ccccc2)C1=O]

was produced by 8%.

Reference Example 70

Synthesis of diacetato{(S)-2,2'-bis[bis(3,5-di-tert-butyl-4-methoxyphenyl)phosphino]-1,1'-binaphthyl}ruthenium (II)

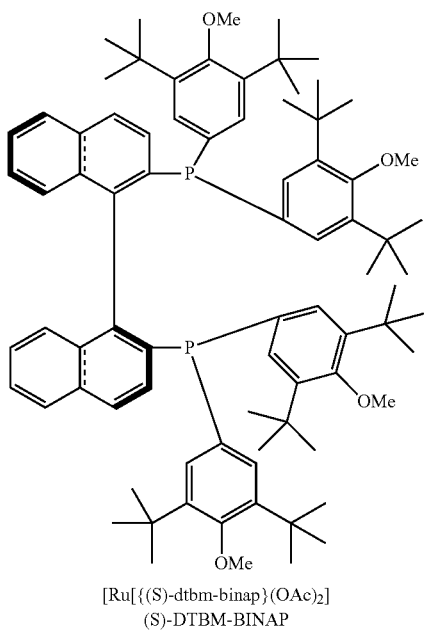

[Ru[{(S)-dtbm-binap}(OAc)₂]
(S)-DTBM-BINAP

In a 1 L Schlenk flask were charged dichloro(p-cymene) ruthenium dimer (7.65 g, 12.5 mmol), and (S)-2,2'-bis[bis(3,5-di-tert-butyl-4-methoxyphenyl)phosphino]-1,1'-binaphthyl (29.78 g, 25.0 mmol), and argon substitution was performed. Deaerated methanol (250 ml) was added by cannulation, and the mixture was stirred at 60° C. for 3 hr. At the same temperature, (sodium acetate (25.0 g, 304.8 mmol)/deaerated methanol (230 ml) solution) was added by cannulation, and the mixture was washed with deaerated methanol (20 mL) and stirred while keeping 60° C.±3° C. for 7 hr. The reaction mixture was allowed to cool, stirred at 25±5° C. for 1 hr and filtered under argon pressurization (cake volume about 100 cm³) in a pressure filter. The filtrate was washed successively with 50% aqueous methanol solution (200 mL) and water (100 mL), argon-through-flow drying was performed for 6 hr, then transferred into a Schlenk flask, and dried under reduced pressure at 30±5° C. to give the title compound as orange crystals. yield 27.21 g, 77.1%.

Reference Example 71

Synthesis of ethyl 2-{4-(difluoromethoxy)benzoyl}aminocyclohexene-1-carboxylate

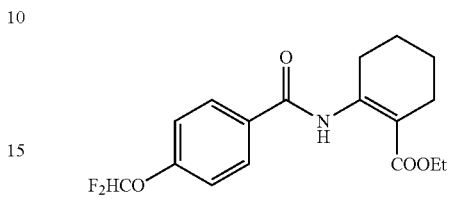

In a 100 ml flask were added (4-difluoromethoxy)benzoic acid (5.0 g, 26.6 mmol), toluene (25 ml) and N,N-dimethylformamide (0.025 ml) at room temperature. Thereafter, thionyl chloride (3.48 g, 29.2 mmol) was added, and the mixture was stirred at 60° C. for 2 hr 30 min. The mixture was concentrated, acetonitrile (10 ml) was added to give an acid chloride solution. In a separate 200 ml flask were charged ethyl 2-aminocyclohexene-1-carboxylate (4.94 g, 29.2 mmol), pyridine (2.3 g, 29.2 mmol) and acetonitrile (15 ml), and the mixture was heated to 40° C. The acid chloride solution prepared above was added over 10 min, and the obtained mixture was stirred at 60° C. for 1 hr 30 min. After cooling to room temperature, water (50 ml) was slowly added dropwise at 25-30° C. and, after dropwise addition, the mixture was stirred for 30 min. The resulting crystals were collected by filtration, washed with water (50 ml), and dried under reduced pressure to give the title compound as white crystals. yield 7.98 g, 88.4%. $^1$H NMR (CDCl$_3$, 500 MHz) δ 1.34 (3H, t, J=7.3 Hz), 1.60-1.72 (4H, m), 2.38-2.41 (2H, m), 3.12-3.16 (2H, m), 4.24 (2H, q, J=6.9 Hz), 6.60 (1H, t, J=73.5 Hz), 7.21 (2H, d, J=8.9 Hz), 8.00 (2H, d, 8.9 Hz), 12.60 (1H, brs)

Anal. Calcd. for C$_{17}$H$_{19}$NO$_4$F$_2$: C, 60.17; H, 5.64; N, 4.13; F, 11.20. Found: C, 60.14; H, 5.79; N, 4.01; F, 11.08 HR-MS: Calcd. for C$_{17}$H$_{19}$NO$_4$F$_2$: 340.1355 [M+H]$^+$. Found 340.1345 [M+H]$^+$.

Reference Example 72

Synthesis of (1S,2R)-ethyl 2-{4-(difluoromethoxy)benzoyl}aminocyclohexane-1-carboxylate

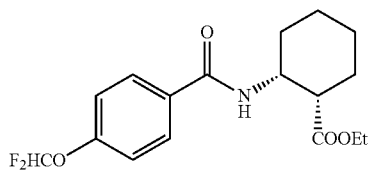 [SMILES: CCOC(=O)[C@H]1CCCC[C@H]1NC(=O)c1ccc(OC(F)F)cc1]

In a 120 ml pressure resistant vessel were charged ethyl 2-{4-(difluoromethoxy)benzoyl}aminocyclohexene-1-carboxylate <5.0 g, 14.7 mmol>, diacetato{(S)-2,2'-bis[bis(3,5-di-tert-butyl-4-methoxyphenyl)phosphino]-1,1'-binaphthyl}ruthenium (II) (0.125 g, 0.0886 mmol), 42% tetrafluoroboric acid (14.3 ml, 0.1772 mmol) and methanol (25 ml) and the mixture was stirred. Thereafter, hydrogen (1 MPa) was filled therein, and the mixture was stirred at 45° C.

for 40 hr. After confirmation of the completion of hydrogen absorption, the ordinary pressure was restored, and the mixture was concentrated into a diastereomer/enantiomer mixture to give the title compound as white crystals. yield 5.0 g. NMR data of (1S,2R) form $^1$H NMR (CDCl$_3$) δ1.27 (3H, t, J=7.1 Hz), 1.4-1.9 (7H, m), 2.1-2.3 (1H, m), 2.8-2.9 (1H, m), 4.1-4.4 (3H, m), 6.56 (1H, t, J=76.6 Hz), 7.15 (2H, d, J=8.7 Hz)

Reference Example 73

Synthesis of (1S,2R)-2-{4-(difluoromethoxy) benzoyl}aminocyclohexane-1-carboxylic acid

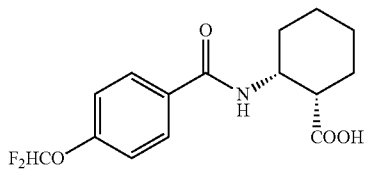 [SMILES: O=C(N[C@@H]1CCCC[C@@H]1C(=O)O)c1ccc(OC(F)F)cc1]

In a 100 ml three-mouthed flask were charged crude (1S, 2R)-ethyl 2-{4-(difluoromethoxy) benzoyl}aminocyclohexane-1-carboxylate (14 g, 41.0 mmol), and ethanol (42 ml), and the mixture was heated to 40° C. 5N Aqueous sodium hydroxide solution (9 ml, 45 mmol) was added, and the mixture was stirred at 40° C. for 2 hr 30 min. After cooling to 25° C., water (89 ml), toluene (28 ml) and heptane (28 ml) were added. The mixture was stirred and the aqueous layer was obtained. The aqueous layer was washed with a mixture of toluene (28 ml) and heptane (28 ml). To the aqueous layer was added acetonitrile (14 ml), and 6N hydrochloric acid and water (47 ml) were added to give crystals. The resulting crystals were collected by filtration, washed with water (70 ml) and then dried to give the title compound as a crude product. Recrystallization from an acetonitrile (80 ml)-water (120 ml) system gave the title compound as pale-gray crystals. yield 8.3 g. (diastereomeric excess>99.9% de) (enantiomeric excess>99.9% ee)

Anal. Calcd. for C$_{15}$H$_{17}$NO$_4$F$_2$: C, 57.50; H, 5.47; N, 4.47; F, 12.13. Found: C, 57.52; H, 5.56; N, 4.41; F, 12.13 HR-MS: Calcd. for C$_{15}$H$_{17}$NO$_4$F$_2$: 314.1198 [M+H]$^+$. Found 314.1214 [M+H]$^+$.

Reference Example 74

Synthesis of ethyl 2-benzoylaminocyclohexene-1-carboxylate

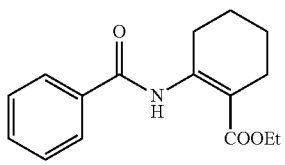 [SMILES: CCOC(=O)C1=C(NC(=O)c2ccccc2)CCCC1]

In a 2000 ml flask were charged ethyl 2-aminocyclohexene-1-carboxylate (80.0 g, 472.8 mmol), pyridine (37.4 g, 472.8 mmol), and acetonitrile (190 ml), and the mixture was dissolved by heating to 40° C. While keeping the mixture at 40-50° C., a solution (126 ml) of benzyl chloride (63.14 g, 449.2 mmol) in acetonitrile was added dropwise. The mixture was stirred at 50-60° C. for 1.5 hr, cooled, and water (631 ml) was added dropwise at 20-30° C. over 30 min. After stirring at the same temperature for 30 min, the precipitate was collected by filtration and washed with water (631 ml). The obtained powder was dried under reduced pressure at 60° C. yield 119.62 g, 97%.

Anal. calcd. for C$_{16}$H$_{19}$NO$_3$, C, 70.31; H, 7.01; N, 5.12. found C, 70.29; H, 7.15; N, 5.08. HR-Ms calcd. for C$_{16}$H$_{19}$NO$_3$, 274.1438 ([M+H]$^+$). found, 274.1428 ([M+H]$^+$).

Reference Example 75

Synthesis of (1S,2R)-ethyl 2-benzoylaminocyclohexane-1-carboxylate

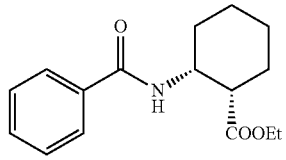 [SMILES: CCOC(=O)[C@H]1CCCC[C@H]1NC(=O)c1ccccc1]

In a 10 mL test tube were charged diacetato{(S)-2,2'-bis[bis(3,5-di-tert-butyl-4-methoxyphenyl)phosphino]-1,1'-binaphthyl}ruthenium (II) (12.9 mg), and ethyl 2-aminocyclohexene-1-carboxylate (50 mg), and the mixture was set on a pressurization apparatus. Argon substitution was performed, and dehydrated methanol for organic synthesis (2.5 ml) was injected with pressure. Thereafter, hydrogen (1 MPa) was charged in and the mixture was stirred at 25° C. for 18 hr. After completion of the reaction, the reaction mixture was analyzed by HPLC.

conversion rate 5.1%, enantiomeric excess rate 46.6% ee.

INDUSTRIAL APPLICABILITY

Using the aforementioned rhodium complex catalyst of the present invention in asymmetric synthesis reactions (particularly, asymmetric reduction), the object compound having an absolute configuration can be obtained efficiently.

The invention claimed is:
1. A rhodium complex coordinated with a compound represented by the formula

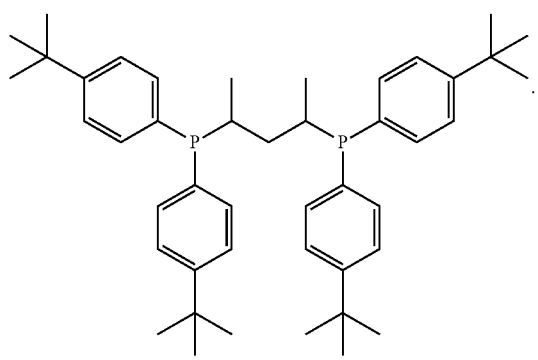 [SMILES: CC(CC(C)P(c1ccc(C(C)(C)C)cc1)c1ccc(C(C)(C)C)cc1)P(c1ccc(C(C)(C)C)cc1)c1ccc(C(C)(C)C)cc1]

2. The complex according to claim 1, which is a rhodium complex coordinated with a compound represented by the formula

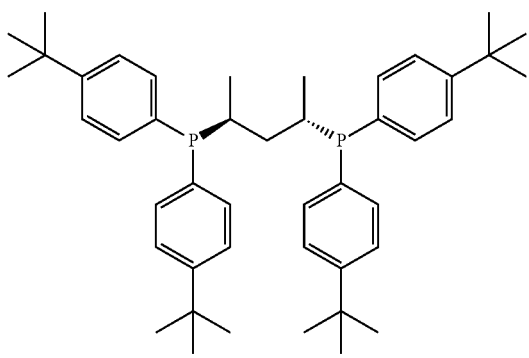 [SMILES: C[C@@H](C[C@H](C)P(c1ccc(C(C)(C)C)cc1)c1ccc(C(C)(C)C)cc1)P(c1ccc(C(C)(C)C)cc1)c1ccc(C(C)(C)C)cc1]

or the formula

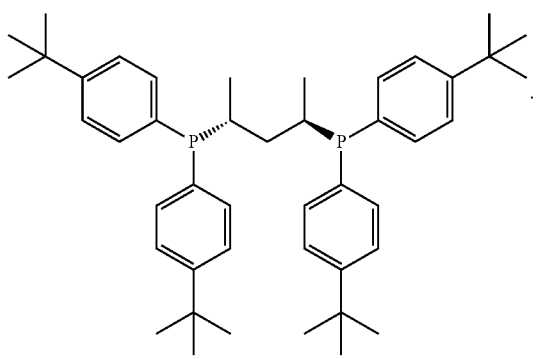 [SMILES: C[C@H](C[C@@H](C)P(c1ccc(C(C)(C)C)cc1)c1ccc(C(C)(C)C)cc1)P(c1ccc(C(C)(C)C)cc1)c1ccc(C(C)(C)C)cc1]

3. A method of producing a compound represented by the formula

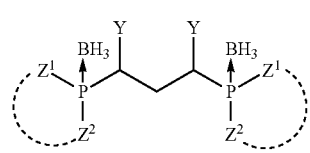

wherein $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), and Y is a hydrocarbon group optionally having substituent(s) or a heterocyclic group optionally having substituent(s), or a salt thereof, comprising reacting a compound represented by the formula

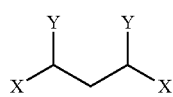

wherein X is a leaving group, and Y is as defined above, or a salt thereof, with a compound represented by the formula

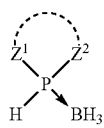

wherein each symbol is as defined above, or a salt thereof, in the presence of potassium tert-butoxide or sodium tert-butoxide.

4. A method of producing a compound represented by the formula

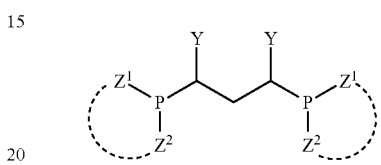

wherein Y is a hydrocarbon group optionally having substituent(s) or a heterocyclic group optionally having substituent(s), $Z^1$ and $Z^2$ are the same or different and each is a hydrogen atom, a halogen atom, a hydrocarbon group optionally having substituent(s) or a heterocyclic group optionally having substituent(s), and $Z^1$ and $Z^2$ are joined to form, together with the adjacent phosphorus atom, a 4- to 8-membered ring optionally having substituent(s), or a salt thereof, comprising reacting a compound represented by the formula

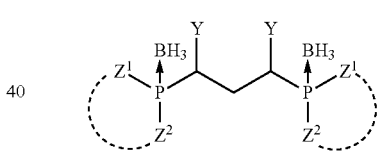

wherein each symbol is as defined above, or a salt thereof, in the presence of a base.

5. A compound represented by the formula

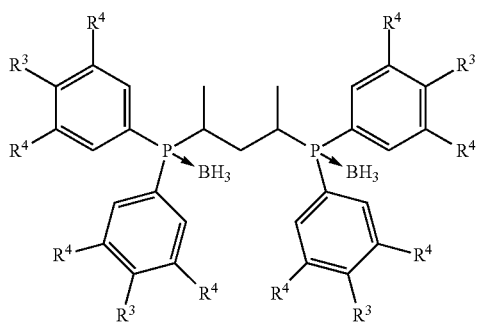

wherein $R^3$ is a hydrogen atom, a $C_{1-6}$ alkyl group, a $C_{1-6}$ alkoxy group or a di-$C_{1-6}$ alkylamino group, and $R^4$ is a hydrogen atom or a $C_{1-6}$ alkyl group, or a salt thereof.

6. A method of producing a compound represented by the formula

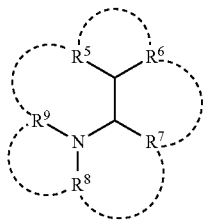

wherein $R^5$, $R^6$ and $R^7$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, an alkoxycarbonyl group optionally having substituent(s), a carboxyl group, a carbamoyl group optionally having substituent(s), a sulfonyl group optionally having substituent(s), a sulfinyl group optionally having substituent(s) or a thiol group optionally having substituent(s), $R^8$ and $R^9$ are the same or different and each is a hydrogen atom, a hydrocarbon group optionally having substituent(s), a heterocyclic group optionally having substituent(s), an acyl group, a sulfonyl group optionally having substituent(s) or a silyl group optionally having substituent(s), and $R^5$ and $R^6$, $R^6$ and $R^7$, $R^7$ and $R^8$, $R^8$ and $R^9$, and $R^9$ and $R^5$ are each optionally joined to form, together with the adjacent atom, a 4- to 8-membered ring optionally having substituent(s), or a salt thereof, comprising reacting a compound represented by the formula

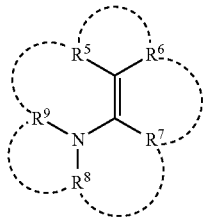

wherein each symbol is as defined above, or a salt thereof, with hydrogen in the presence of a transition metal complex as a catalyst and an aromatic compound having a hydroxy group.

7. A method of producing a compound represented by the formula

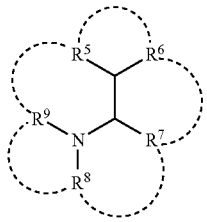

wherein $R^5$, $R^6$ and $R^7$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, an alkoxycarbonyl group optionally having substituent(s), a carboxyl group, a carbamoyl group optionally having substituent(s), a sulfonyl group optionally having substituent(s), a sulfinyl group optionally having substituent(s) or a thiol group optionally having substituent(s), $R^8$ and $R^9$ are the same or different and each is a hydrogen atom, a hydrocarbon group optionally having substituent(s), a heterocyclic group optionally having substituent(s), an acyl group, a sulfonyl group optionally having substituent(s) or a silyl group optionally having substituent(s), and $R^5$ and $R^6$, $R^6$ and $R^7$, $R^7$ and $R^8$, $R^8$ and $R^9$, and $R^9$ and $R^5$ are each optionally joined to form, together with the adjacent atom, a 4- to 8-membered ring optionally having substituent(s), or a salt thereof, comprising reacting a compound represented by the formula

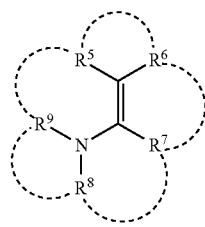

wherein each symbol is as defined above, or a salt thereof, with hydrogen in the presence of a transition metal complex as a catalyst and a compound represented by the formula

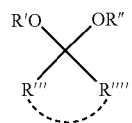

wherein R' and R" are the same or different and each is an alkyl group optionally having substituent(s), R'" and R"" are the same or different and each is an alkyl group optionally having substituent(s), or R'" and R"" are joined to form, together with the adjacent carbon atom, a 4- to 9-membered ring optionally having substituent(s).

8. A method of producing a compound represented by the formula

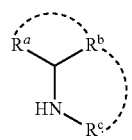

wherein $R^a$ and $R^b$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, a sulfonyl group optionally having substituent(s), a sulfinyl group optionally having substituent(s) or a thiol group optionally having substituent(s), $R^c$ is a hydrogen atom, a hydrocarbon group optionally having substituent(s), a heterocyclic group optionally having substituent(s), an acyl group, an amino group optionally having substituent(s), a sulfonyl group optionally having substituent(s) or a silyl group optionally having substituent(s), and $R^a$ and $R^b$, and $R^b$ and $R^c$ are each optionally joined to form, together with the adjacent atom, a 4- to 8-membered ring optionally having substituent(s), or a salt thereof, comprising reacting a compound represented by the formula

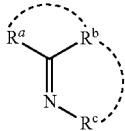

wherein each symbol is as defined above, or a salt thereof, with hydrogen in the presence of a transition metal complex as a catalyst and a compound represented by the formula

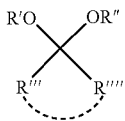

wherein R' and R" are the same or different and each is an alkyl group optionally having substituent(s), R'" and R"" are the same or different and each is an alkyl group optionally having substituent(s), or R' and R"" are joined to form, together with the adjacent carbon atom, a 4- to 9-membered ring optionally having substituent(s).

9. The method according to claim 6, wherein the aromatic compound having a hydroxy group is a cyanuric acid.

10. The method according to claim 7, wherein the compound represented by the formula

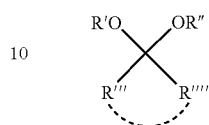

is 2,2-dimethoxypropane.

11. The method according to claim 8, wherein the compound represented by the formula

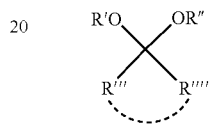

is 2,2-dimethoxypropane.

* * * * *

UNITED STATES PATENT AND TRADEMARK OFFICE
CERTIFICATE OF CORRECTION

PATENT NO. : 9,238,667 B2
APPLICATION NO. : 14/388383
DATED : January 19, 2016
INVENTOR(S) : Mitsuhisa Yamano It is certified that error appears in the above-identified patent and that said Letters Patent is hereby corrected as shown below:

Claims

In columns 134-136, replace Claim 8 with the following corrected claim.

8. A method of producing a compound represented by the formula

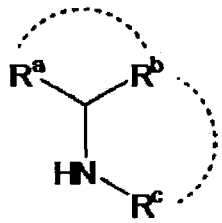

wherein $R^a$ and $R^b$ are the same or different and each is a hydrogen atom, a halogen atom, a nitro group, a cyano group, a hydrocarbon group optionally having substituent(s), a heterocyclic group optionally having substituent(s), a hydroxy group optionally having substituent(s), an acyl group, a sulfonyl group optionally having substituent(s), a sulfinyl group optionally having substituent(s) or a thiol group optionally having substituent(s), $R^c$ is a hydrogen atom, a hydrocarbon group optionally having substituent(s), a heterocyclic group optionally having substituent(s), an acyl group, an amino group optionally having substituent(s), a sulfonyl group optionally having substituent(s) or a silyl group optionally having substituent(s), and $R^a$ and $R^b$, and $R^b$ and $R^c$ are each optionally joined to form, together with the adjacent atom, a 4- to 8-membered ring optionally having substituent(s), or a salt thereof, comprising reacting a compound represented by the formula

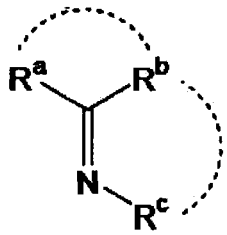

Signed and Sealed this
Twenty-first Day of June, 2016

Michelle K. Lee
*Director of the United States Patent and Trademark Office* wherein each symbol is as defined above, or a salt thereof, with hydrogen in the presence of a transition metal complex as a catalyst and a compound represented by the formula

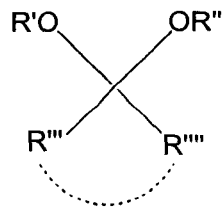

wherein R' and R" are the same or different and each is an alkyl group optionally having substituent(s), R'" and R"" are the same or different and each is an alkyl group optionally having substituent(s), or R'" and R"" are joined to form, together with the adjacent carbon atom, a 4- to 9-membered ring optionally having substituent(s).